(12) United States Patent
Huh et al.

(10) Patent No.: US 11,911,284 B2
(45) Date of Patent: Feb. 27, 2024

(54) CURVED EXPANDABLE INTERBODY DEVICES AND DEPLOYMENT TOOLS

(71) Applicant: Spinal Elements, Inc., Carlsbad, CA (US)

(72) Inventors: Edwin Huh, Irvine, CA (US); Jason Blain, Encinitas, CA (US); Taylor Semingson, San Diego, CA (US); Nicholas Chen, Carlsbad, CA (US); Ketchen Smith, Escondido, CA (US); David Ortiz, Carlsbad, CA (US); Geoffrey Toon, Vista, CA (US); Morton Albert, Carlsbad, CA (US)

(73) Assignee: Spinal Elements, Inc., Carlsbad, CA (US)

( * ) Notice: Subject to any disclaimer, the term of this patent is extended or adjusted under 35 U.S.C. 154(b) by 0 days.

(21) Appl. No.: 17/523,620

(22) Filed: Nov. 10, 2021

(65) Prior Publication Data
US 2022/0151800 A1    May 19, 2022

Related U.S. Application Data

(60) Provisional application No. 63/179,420, filed on Apr. 25, 2021, provisional application No. 63/116,060, filed on Nov. 19, 2020.

(51) Int. Cl.
*A61F 2/44* (2006.01)
*A61F 2/46* (2006.01)
*A61F 2/30* (2006.01)

(52) U.S. Cl.
CPC ........ *A61F 2/4425* (2013.01); *A61F 2/30771* (2013.01); *A61F 2/4465* (2013.01);
(Continued)

(58) Field of Classification Search
CPC .............................................. A61F 2/442–447
See application file for complete search history.

(56) References Cited

U.S. PATENT DOCUMENTS 1,845,428 A    2/1932    Llewellyn
2,440,123 A    4/1948    Smith
(Continued)

FOREIGN PATENT DOCUMENTS

CA    1 329 525    5/1994
CA    2 521 526    11/2004
(Continued)

OTHER PUBLICATIONS

Official Communication in Australian Application No. 2006227755, dated Dec. 8, 2010.
(Continued)

*Primary Examiner* — Eduardo C Robert
*Assistant Examiner* — Steven J Cotroneo
(74) *Attorney, Agent, or Firm* — Knobbe, Martens, Olson & Bear, LLP

(57) ABSTRACT

A curved expandable interbody device for placement between vertebrae having an upper structure, a lower structure, and a screw mechanism, wherein actuation of the screw mechanism moves the upper and lower structures between a collapsed configuration and an expanded configuration. A deployment tool couples to the curved expandable interbody device for positioning the device between adjacent vertebrae and actuating the screw mechanism, wherein the deployment tool can lock to the curved expandable interbody device and pivot relative to the curved expandable interbody device.

20 Claims, 33 Drawing Sheets

(52) U.S. Cl.
CPC ... *A61F 2/4611* (2013.01); *A61F 2002/30011* (2013.01); *A61F 2002/3021* (2013.01); *A61F 2002/30321* (2013.01); *A61F 2002/30433* (2013.01); *A61F 2002/30841* (2013.01); *A61F 2002/30891* (2013.01); *A61F 2002/443* (2013.01); *A61F 2002/4629* (2013.01); *A61F 2310/00023* (2013.01)

(56) References Cited

U.S. PATENT DOCUMENTS

| | | |
|---|---|---|
| 2,500,993 A | 3/1950 | Christopher |
| 2,677,369 A | 5/1954 | Knowles |
| 3,426,364 A | 2/1969 | Lumb |
| 3,574,381 A | 4/1971 | Ocheltree et al. |
| 3,848,601 A | 11/1974 | Ma et al. |
| 3,867,728 A | 2/1975 | Stubstad et al. |
| 3,893,196 A | 7/1975 | Hochman |
| 3,953,140 A | 4/1976 | Carlstrom |
| 3,987,499 A | 10/1976 | Scharbach et al. |
| 4,013,071 A | 3/1977 | Rosenberg |
| 4,309,777 A | 1/1982 | Patil |
| 4,349,921 A | 9/1982 | Kuntz |
| 4,388,921 A | 6/1983 | Sutter et al. |
| 4,401,112 A | 8/1983 | Rezaian |
| 4,464,090 A | 8/1984 | Duran |
| 4,484,570 A | 11/1984 | Sutter et al. |
| 4,554,914 A | 11/1985 | Kapp et al. |
| 4,599,086 A | 7/1986 | Doty |
| 4,834,757 A | 5/1989 | Brantigan |
| 4,892,545 A | 1/1990 | Day et al. |
| 4,904,261 A | 2/1990 | Dove et al. |
| 4,917,704 A | 4/1990 | Frey et al. |
| 4,955,908 A | 9/1990 | Frey et al. |
| 4,961,740 A | 10/1990 | Ray et al. |
| 5,002,576 A | 3/1991 | Fuhrmann et al. |
| 5,053,036 A | 10/1991 | Perren et al. |
| 5,057,111 A | 10/1991 | Park |
| 5,085,660 A | 2/1992 | Lin |
| 5,147,361 A | 9/1992 | Ojima et al. |
| 5,147,402 A | 9/1992 | Bohler et al. |
| 5,176,709 A | 1/1993 | Branemark |
| 5,192,327 A | 3/1993 | Brantigan |
| 5,269,784 A | 12/1993 | Mast |
| 5,275,601 A | 1/1994 | Gogolewski et al. |
| 5,304,179 A | 4/1994 | Wagner |
| 5,306,307 A | 4/1994 | Senter et al. |
| 5,364,399 A | 11/1994 | Lowery et al. |
| 5,397,364 A | 3/1995 | Kozak et al. |
| 5,458,641 A | 10/1995 | Ramirez Jimenez |
| 5,474,555 A | 12/1995 | Puno et al. |
| 5,501,684 A | 3/1996 | Schlapfer et al. |
| 5,520,690 A | 5/1996 | Errico et al. |
| 5,522,899 A | 6/1996 | Michelson |
| 5,534,027 A | 7/1996 | Hodorek |
| 5,558,674 A | 9/1996 | Heggeness et al. |
| 5,578,034 A | 11/1996 | Estes |
| 5,607,426 A | 3/1997 | Ralph et al. |
| 5,607,428 A | 3/1997 | Lin |
| 5,609,635 A | 3/1997 | Michelson |
| 5,616,144 A | 4/1997 | Yapp et al. |
| 5,643,265 A | 7/1997 | Errico et al. |
| 5,665,089 A | 9/1997 | Dall et al. |
| 5,676,666 A | 10/1997 | Oxland et al. |
| 5,676,702 A | 10/1997 | Ratron |
| 5,681,311 A | 10/1997 | Foley et al. |
| 5,713,900 A | 2/1998 | Benzel et al. |
| 5,735,853 A | 4/1998 | Olerud |
| 5,743,914 A | 4/1998 | Skiba |
| 5,749,916 A | 5/1998 | Richelsoph |
| 5,755,796 A | 5/1998 | Ibo et al. |
| 5,766,252 A | 6/1998 | Henry et al. |
| 5,776,199 A | 7/1998 | Michelson |
| 5,807,396 A | 9/1998 | Raveh |
| 5,810,823 A | 9/1998 | Klaue et al. |
| 5,849,004 A | 12/1998 | Bramlet |
| 5,851,207 A | 12/1998 | Cesarone |
| 5,876,402 A | 3/1999 | Errico et al. |
| 5,888,223 A | 3/1999 | Bray |
| 5,888,227 A | 3/1999 | Cottle |
| 5,902,303 A | 5/1999 | Eckhof et al. |
| 5,904,683 A | 5/1999 | Pohndorf et al. |
| 5,925,048 A | 7/1999 | Ahmad et al. |
| 5,931,838 A | 8/1999 | Vito |
| 5,951,558 A | 9/1999 | Fiz |
| 5,954,722 A | 9/1999 | Bono |
| 6,001,130 A | 12/1999 | Bryan et al. |
| 6,030,389 A | 2/2000 | Wagner et al. |
| 6,066,175 A | 5/2000 | Henderson et al. |
| 6,082,568 A | 7/2000 | Flanagan |
| 6,086,613 A | 7/2000 | Camino et al. |
| 6,117,173 A | 9/2000 | Taddia et al. |
| 6,136,031 A | 10/2000 | Middleton |
| 6,139,550 A | 10/2000 | Michelson |
| 6,152,927 A | 11/2000 | Farris et al. |
| 6,156,037 A | 12/2000 | Huec et al. |
| 6,176,882 B1 * | 1/2001 | Biedermann ........... A61F 2/447 623/17.11 |
| 6,193,721 B1 | 2/2001 | Michelson |
| 6,206,881 B1 | 3/2001 | Frigg et al. |
| 6,206,924 B1 | 3/2001 | Timm |
| 6,215,093 B1 | 4/2001 | Meiners et al. |
| 6,231,610 B1 | 5/2001 | Geisler |
| 6,235,033 B1 | 5/2001 | Brace et al. |
| 6,235,034 B1 | 5/2001 | Bray |
| 6,235,059 B1 | 5/2001 | Benezech et al. |
| 6,241,731 B1 | 6/2001 | Fiz |
| 6,245,108 B1 | 6/2001 | Biscup |
| 6,261,291 B1 | 7/2001 | Talaber et al. |
| 6,273,889 B1 | 8/2001 | Richelsoph |
| 6,287,309 B1 | 9/2001 | Baccelli et al. |
| 6,302,883 B1 | 10/2001 | Bono |
| 6,306,136 B1 | 10/2001 | Baccelli |
| 6,306,139 B1 | 10/2001 | Fuentes |
| 6,306,170 B2 | 10/2001 | Rau |
| 6,331,179 B1 | 12/2001 | Freid et al. |
| 6,342,055 B1 | 1/2002 | Eisermann et al. |
| 6,383,186 B1 | 5/2002 | Michelson |
| 6,395,035 B2 | 5/2002 | Bresina et al. |
| 6,402,755 B1 | 6/2002 | Pisharodi |
| 6,413,259 B1 | 7/2002 | Lyons et al. |
| 6,428,542 B1 | 8/2002 | Michelson |
| 6,432,106 B1 | 8/2002 | Fraser |
| 6,447,544 B1 | 9/2002 | Michelson |
| 6,447,547 B1 | 9/2002 | Michelson |
| 6,454,769 B2 | 9/2002 | Wagner et al. |
| 6,461,359 B1 | 10/2002 | Tribus et al. |
| 6,478,823 B1 | 11/2002 | Michelson |
| 6,491,724 B1 | 12/2002 | Ferree |
| 6,503,250 B2 | 1/2003 | Paul |
| 6,508,818 B2 | 1/2003 | Steiner et al. |
| 6,537,320 B1 | 3/2003 | Michelson |
| 6,565,570 B2 | 5/2003 | Sterett et al. |
| 6,569,168 B2 | 5/2003 | Lin |
| 6,575,975 B2 | 6/2003 | Brace et al. |
| 6,579,290 B1 | 6/2003 | Hardcastle et al. |
| 6,582,432 B1 | 6/2003 | Michelson |
| 6,599,290 B2 | 7/2003 | Bailey et al. |
| 6,602,255 B1 | 8/2003 | Campbell et al. |
| 6,602,256 B1 | 8/2003 | Hayes |
| 6,613,053 B1 | 9/2003 | Collins et al. |
| 6,623,486 B1 | 9/2003 | Weaver et al. |
| 6,626,907 B2 | 9/2003 | Campbell et al. |
| 6,626,911 B1 | 9/2003 | Engman et al. |
| 6,645,208 B2 | 11/2003 | Apfelbaum et al. |
| 6,645,209 B2 | 11/2003 | Hall, IV et al. |
| 6,652,525 B1 | 11/2003 | Assaker et al. |
| 6,656,181 B2 | 12/2003 | Dixon et al. |
| 6,656,224 B2 | 12/2003 | Middleton |
| 6,660,038 B2 | 12/2003 | Boyer, II et al. |
| 6,669,700 B1 | 12/2003 | Farris et al. |
| 6,676,892 B2 | 1/2004 | Das et al. |
| 6,682,561 B2 | 1/2004 | Songer et al. |
| 6,682,563 B2 | 1/2004 | Scharf |

(56) References Cited

U.S. PATENT DOCUMENTS

| | | |
|---|---|---|
| 6,695,845 B2 | 2/2004 | Dixon et al. |
| 6,695,846 B2 | 2/2004 | Richelsoph et al. |
| 6,702,817 B2 | 3/2004 | Beger et al. |
| 6,719,794 B2 | 4/2004 | Gerber et al. |
| 6,730,127 B2 | 5/2004 | Michelson |
| 6,740,087 B2 | 5/2004 | Knox |
| 6,743,255 B2 | 6/2004 | Ferree |
| 6,746,450 B1 | 6/2004 | Wall et al. |
| 6,755,833 B1 | 6/2004 | Paul et al. |
| 6,758,849 B1 | 7/2004 | Michelson |
| 6,767,369 B2 | 7/2004 | Boyer, II et al. |
| 6,776,798 B2 | 8/2004 | Camino et al. |
| 6,780,186 B2 | 8/2004 | Errico et al. |
| 6,808,537 B2 | 10/2004 | Michelson |
| 6,830,570 B1 | 12/2004 | Frey et al. |
| 6,833,006 B2 | 12/2004 | Foley et al. |
| 6,835,208 B2 | 12/2004 | Marchosky |
| 6,884,242 B2 | 4/2005 | LeHuec et al. |
| 6,890,334 B2 | 5/2005 | Brace et al. |
| 6,890,335 B2 | 5/2005 | Grabowski et al. |
| 6,890,355 B2 | 5/2005 | Michelson |
| 6,932,610 B2 | 8/2005 | Ono et al. |
| 6,962,606 B2 | 11/2005 | Michelson |
| 6,964,664 B2 | 11/2005 | Freid et al. |
| 6,974,480 B2 | 12/2005 | Messerli et al. |
| 6,984,234 B2 | 1/2006 | Bray |
| 7,001,389 B1 | 2/2006 | Navarro et al. |
| 7,001,672 B2 | 2/2006 | Justin et al. |
| 7,025,769 B1 | 4/2006 | Ferree |
| 7,048,739 B2 | 5/2006 | Konieczynski et al. |
| 7,063,701 B2 | 6/2006 | Michelson |
| 7,077,844 B2 | 7/2006 | Michelson |
| 7,112,222 B2 | 9/2006 | Fraser et al. |
| 7,135,024 B2 | 11/2006 | Cook et al. |
| 7,141,068 B2 | 11/2006 | Ross et al. |
| 7,172,627 B2 | 2/2007 | Fiere et al. |
| 7,182,782 B2 | 2/2007 | Kirschman |
| 7,186,254 B2 | 3/2007 | Dinh et al. |
| 7,217,291 B2 | 5/2007 | Zucherman et al. |
| 7,220,263 B2 | 5/2007 | Cordaro |
| 7,232,463 B2 | 6/2007 | Falahee |
| 7,232,464 B2 | 6/2007 | Mathieu et al. |
| 7,235,082 B2 | 6/2007 | Bartish et al. |
| 7,273,481 B2 | 9/2007 | Lombardo et al. |
| 7,306,605 B2 | 12/2007 | Ross |
| 7,309,340 B2 | 12/2007 | Fallin et al. |
| 7,473,277 B2 | 1/2009 | Boyer, II et al. |
| 7,481,829 B2 | 1/2009 | Baynham et al. |
| 7,481,830 B2 | 1/2009 | Wall et al. |
| 7,503,933 B2 | 3/2009 | Michelson |
| 7,521,017 B2 | 4/2009 | Kunze et al. |
| 7,524,325 B2 | 4/2009 | Khalili |
| 7,537,664 B2 | 5/2009 | O'Neill et al. |
| 7,540,882 B2 | 6/2009 | Michelson |
| 7,547,324 B2 | 6/2009 | Cragg et al. |
| 7,621,943 B2 | 11/2009 | Michelson |
| 7,628,816 B2 | 12/2009 | Magerl et al. |
| 7,641,665 B2 | 1/2010 | Zubok et al. |
| 7,641,690 B2 | 1/2010 | Abdou |
| 7,651,517 B2 | 1/2010 | Konieczynski et al. |
| 7,658,766 B2 | 2/2010 | Melkent et al. |
| 7,674,294 B2 | 3/2010 | Karahalios et al. |
| 7,674,297 B2 | 3/2010 | Falahee |
| 7,693,981 B2 | 4/2010 | Clubb et al. |
| 7,708,778 B2 | 5/2010 | Gordon et al. |
| 7,708,779 B2 | 5/2010 | Edie et al. |
| 7,718,109 B2 | 5/2010 | Robb et al. |
| 7,806,932 B2 | 10/2010 | Webb et al. |
| 7,819,903 B2 | 10/2010 | Fraser et al. |
| 7,837,734 B2 | 11/2010 | Zucherman et al. |
| 7,857,839 B2 | 12/2010 | Duong et al. |
| 7,892,239 B2 | 2/2011 | Warnick et al. |
| 7,914,561 B2 | 3/2011 | Konieczynski et al. |
| 7,931,840 B2 | 4/2011 | Michelson |
| 7,935,137 B2 | 5/2011 | Gorhan et al. |
| 7,959,675 B2 | 6/2011 | Gately |
| 7,963,981 B2 | 6/2011 | Binder et al. |
| 7,972,366 B2 | 7/2011 | Richelsoph et al. |
| 7,985,255 B2 | 7/2011 | Bray et al. |
| 7,998,212 B2 | 8/2011 | Schwab et al. |
| 8,025,697 B2 | 9/2011 | McClellan, III et al. |
| 8,043,293 B2 | 10/2011 | Warnick |
| 8,062,375 B2 | 11/2011 | Glerum et al. |
| 8,088,163 B1 | 1/2012 | Kleiner |
| 8,100,955 B2 | 1/2012 | Blain et al. |
| 8,142,886 B2 | 3/2012 | Noble et al. |
| 8,147,554 B2 | 4/2012 | Hansell et al. |
| 8,157,845 B2 | 4/2012 | Warnick et al. |
| 8,231,661 B2 | 7/2012 | Carls |
| 8,252,060 B2 | 8/2012 | Hansell et al. |
| 8,267,966 B2 | 9/2012 | McCormack et al. |
| 8,268,001 B2 | 9/2012 | Butler et al. |
| 8,277,510 B2 | 10/2012 | Kleiner |
| 8,282,675 B2 | 10/2012 | Maguire et al. |
| 8,282,682 B2 | 10/2012 | Kirschman |
| 8,292,960 B2 | 10/2012 | Kleiner |
| 8,343,224 B2 | 1/2013 | Lynn et al. |
| 8,366,777 B2 | 2/2013 | Matthis et al. |
| 8,382,842 B2 | 2/2013 | Greenhalgh et al. |
| 8,394,125 B2 | 3/2013 | Assell |
| 8,409,290 B2 | 4/2013 | Zamani et al. |
| 8,414,590 B2 | 4/2013 | Oh et al. |
| 8,425,529 B2 | 4/2013 | Milz et al. |
| 8,430,930 B2 | 4/2013 | Hunt |
| 8,435,298 B2 * | 5/2013 | Weiman ............... A61F 2/44 623/17.11 |
| 8,444,650 B2 | 5/2013 | Warnick et al. |
| 8,470,039 B2 | 6/2013 | Blain |
| 8,480,745 B2 | 7/2013 | Liu et al. |
| 8,491,658 B1 | 7/2013 | Etminan |
| 8,496,691 B2 | 7/2013 | Blain |
| 8,496,708 B2 | 7/2013 | Blain |
| 8,506,636 B2 | 8/2013 | Dye |
| 8,518,120 B2 | 8/2013 | Glerum et al. |
| 8,545,566 B2 | 10/2013 | Niemiec et al. |
| 8,556,979 B2 | 10/2013 | Glerum et al. |
| 8,579,904 B2 | 11/2013 | Siccardi et al. |
| 8,603,175 B2 | 12/2013 | Thibodeau |
| 8,617,246 B2 | 12/2013 | Malone |
| 8,628,578 B2 | 1/2014 | Miller et al. |
| 8,632,595 B2 | 1/2014 | Weiman |
| 8,652,137 B2 | 2/2014 | Blain et al. |
| 8,652,143 B2 | 2/2014 | Mcclellan, III et al. |
| 8,679,183 B2 | 3/2014 | Glerum et al. |
| 8,685,095 B2 | 4/2014 | Miller et al. |
| 8,685,098 B2 | 4/2014 | Glerum et al. |
| 8,690,949 B2 | 4/2014 | Messerli et al. |
| 8,696,721 B2 | 4/2014 | Blain |
| 8,702,798 B2 | 4/2014 | Matthis et al. |
| 8,709,086 B2 | 4/2014 | Glerum |
| 8,715,355 B2 | 5/2014 | Kleiner |
| 8,728,387 B2 | 5/2014 | Jones et al. |
| 8,740,942 B2 | 6/2014 | Blain |
| 8,758,443 B2 | 6/2014 | Ullrich, Jr. et al. |
| 8,795,366 B2 | 8/2014 | Varela |
| 8,795,370 B2 | 8/2014 | Kirschman |
| 8,801,785 B2 | 8/2014 | Brittan et al. |
| 8,801,791 B2 | 8/2014 | Soo et al. |
| 8,801,793 B2 | 8/2014 | McKay |
| 8,801,794 B2 | 8/2014 | Blain |
| 8,843,229 B2 | 9/2014 | Vanasse et al. |
| 8,845,731 B2 | 9/2014 | Weiman |
| 8,852,279 B2 | 10/2014 | Weiman |
| 8,888,853 B2 | 11/2014 | Glerum et al. |
| 8,888,854 B2 | 11/2014 | Glerum et al. |
| 8,926,704 B2 | 1/2015 | Glerum et al. |
| 8,986,307 B2 | 3/2015 | Kirschman |
| 8,986,383 B2 | 3/2015 | Castro |
| 8,992,703 B2 | 3/2015 | O'Neill et al. |
| 8,998,924 B2 | 4/2015 | Simpson et al. |
| 9,060,873 B2 | 6/2015 | Abdou |
| 9,078,706 B2 | 7/2015 | Kirschman |
| 9,095,385 B2 | 8/2015 | Wallenstein et al. |
| 9,101,410 B1 | 8/2015 | Urrea |

(56) References Cited

U.S. PATENT DOCUMENTS

| | | |
|---|---|---|
| 9,138,327 B1 | 9/2015 | Mcclellan, III |
| 9,138,330 B2 | 9/2015 | Hansell et al. |
| 9,198,772 B2 | 12/2015 | Weiman |
| 9,204,974 B2 | 12/2015 | Glerum et al. |
| 9,220,542 B2 | 12/2015 | Kerboul et al. |
| 9,220,547 B2 | 12/2015 | Blain et al. |
| 9,226,836 B2 | 1/2016 | Glerum |
| 9,259,327 B2 | 2/2016 | Niemiec et al. |
| 9,265,546 B2 | 2/2016 | Blain |
| 9,271,765 B2 | 3/2016 | Blain |
| 9,271,845 B2 | 3/2016 | Hunt et al. |
| 9,320,610 B2* | 4/2016 | Alheidt ............... A61F 2/4611 |
| 9,358,126 B2 | 6/2016 | Glerum et al. |
| 9,399,086 B2 | 7/2016 | Melkent et al. |
| 9,402,736 B2 | 8/2016 | Etminan |
| 9,415,137 B2 | 8/2016 | Meridew et al. |
| 9,421,108 B2 | 8/2016 | Hunt |
| 9,427,328 B2 | 8/2016 | Drochner et al. |
| 9,433,707 B2 | 9/2016 | Swords et al. |
| 9,439,778 B2 | 9/2016 | Biedermann et al. |
| 9,456,901 B2 | 10/2016 | Jones et al. |
| 9,463,099 B2 | 10/2016 | Levy et al. |
| 9,545,317 B2 | 1/2017 | Hunt |
| 9,549,823 B2 | 1/2017 | Hunt et al. |
| 9,554,918 B2 | 1/2017 | Weiman |
| 9,572,669 B2 | 2/2017 | Hunt et al. |
| 9,585,707 B2 | 3/2017 | Blain |
| 9,615,934 B2 | 4/2017 | Khurana |
| 9,636,226 B2 | 5/2017 | Hunt |
| 9,662,223 B2 | 5/2017 | Matthis et al. |
| 9,662,226 B2 | 5/2017 | Wickham |
| 9,668,876 B2 | 6/2017 | Blain et al. |
| 9,700,428 B2 | 7/2017 | Niemiec et al. |
| 9,707,317 B2 | 7/2017 | Hunter et al. |
| 9,757,235 B2 | 9/2017 | Hunt et al. |
| 9,757,247 B2 | 9/2017 | Mantri |
| 9,770,343 B2 | 9/2017 | Weiman |
| 9,782,269 B2 | 10/2017 | Hansell et al. |
| RE46,647 E* | 12/2017 | Messerli ............ A61B 17/1659 |
| 9,867,713 B2 | 1/2018 | Milz et al. |
| 9,889,020 B2 | 2/2018 | Baynham |
| 9,936,984 B2 | 4/2018 | Blain |
| 9,949,841 B2 | 4/2018 | Glerum et al. |
| 9,962,271 B2 | 5/2018 | Glerum |
| 9,968,462 B2 | 5/2018 | Weiman |
| 9,980,823 B2 | 5/2018 | Matthis et al. |
| 9,980,825 B2 | 5/2018 | Nichols et al. |
| 9,987,051 B2 | 6/2018 | Nunley et al. |
| 9,987,149 B2 | 6/2018 | Simpson et al. |
| 10,004,607 B2 | 6/2018 | Weiman et al. |
| 10,022,245 B2* | 7/2018 | Frasier ................. A61F 2/442 |
| 10,028,841 B2 | 7/2018 | Moore et al. |
| 10,034,770 B2 | 7/2018 | Etminan |
| 10,064,737 B2 | 9/2018 | Tsai et al. |
| 10,092,412 B2 | 10/2018 | Drochner et al. |
| 10,130,490 B2 | 11/2018 | Hansell et al. |
| 10,154,912 B2 | 12/2018 | Glerum |
| 10,245,152 B2 | 4/2019 | Kloss |
| 10,271,957 B2 | 4/2019 | Niemiec et al. |
| 10,299,938 B1 | 5/2019 | Ehteshami |
| 10,369,009 B2 | 8/2019 | Joly et al. |
| 10,470,892 B2 | 11/2019 | Abdou |
| 10,478,313 B1* | 11/2019 | Sweeney, III ......... A61F 2/4611 |
| 10,512,545 B2 | 12/2019 | Arnone |
| 10,555,819 B2 | 2/2020 | Miccio |
| 10,568,664 B2 | 2/2020 | Blain et al. |
| 10,610,373 B2 | 4/2020 | Jang et al. |
| 10,660,763 B2 | 5/2020 | Wilson et al. |
| 10,667,927 B2 | 6/2020 | Lamborne et al. |
| 10,687,876 B2 | 6/2020 | Vrionis et al. |
| 10,702,397 B2 | 7/2020 | Simpson et al. |
| 10,709,575 B2 | 7/2020 | Robinson |
| 10,758,361 B2 | 9/2020 | Blain |
| 10,765,525 B2 | 9/2020 | Sansur et al. |
| 10,905,567 B2 | 2/2021 | Kuyler et al. |
| 10,993,810 B2 | 5/2021 | Magagnoli |
| 11,026,801 B2 | 6/2021 | Suh et al. |
| 11,147,682 B2 | 10/2021 | Trudeau et al. |
| 11,147,687 B2 | 10/2021 | Hyeon et al. |
| 11,173,047 B2* | 11/2021 | Milz ..................... A61F 2/4465 |
| 11,179,247 B2 | 11/2021 | Jebsen et al. |
| 11,213,404 B2 | 1/2022 | Foley et al. |
| 11,285,014 B1* | 3/2022 | Josse ..................... A61F 2/4455 |
| 11,364,057 B2 | 6/2022 | Blain et al. |
| 11,382,769 B2 | 7/2022 | Blain et al. |
| 2001/0007941 A1 | 7/2001 | Steiner et al. |
| 2001/0014807 A1 | 8/2001 | Wagner et al. |
| 2001/0047207 A1 | 11/2001 | Michelson |
| 2002/0004683 A1 | 1/2002 | Michelson |
| 2002/0016595 A1 | 2/2002 | Michelson |
| 2002/0022843 A1 | 2/2002 | Michelson |
| 2002/0045898 A1 | 4/2002 | Freid et al. |
| 2002/0116064 A1 | 8/2002 | Middleton |
| 2002/0147450 A1 | 10/2002 | LeHuec et al. |
| 2002/0151895 A1 | 10/2002 | Soboleski et al. |
| 2002/0169507 A1 | 11/2002 | Malone |
| 2002/0169508 A1 | 11/2002 | Songer et al. |
| 2003/0060828 A1 | 3/2003 | Michelson |
| 2003/0093082 A1 | 5/2003 | Campbell et al. |
| 2003/0135279 A1 | 7/2003 | Michelson |
| 2003/0139812 A1 | 7/2003 | Garcia et al. |
| 2003/0167091 A1 | 9/2003 | Scharf |
| 2003/0171753 A1 | 9/2003 | Collins et al. |
| 2003/0187442 A1 | 10/2003 | Richelsoph et al. |
| 2003/0212399 A1 | 11/2003 | Dinh et al. |
| 2004/0010254 A1 | 1/2004 | Cook et al. |
| 2004/0068319 A1 | 4/2004 | Cordaro |
| 2004/0087951 A1 | 5/2004 | Khalili |
| 2004/0097935 A1 | 5/2004 | Richelsoph et al. |
| 2004/0127900 A1 | 7/2004 | Konieczynski et al. |
| 2004/0127904 A1 | 7/2004 | Konieczynski et al. |
| 2004/0176778 A1 | 9/2004 | Zubok et al. |
| 2004/0181227 A1 | 9/2004 | Khalili |
| 2004/0210219 A1 | 10/2004 | Bray |
| 2004/0220570 A1 | 11/2004 | Frigg et al. |
| 2004/0230192 A1 | 11/2004 | Graf |
| 2004/0260306 A1 | 12/2004 | Fallin et al. |
| 2005/0027296 A1 | 2/2005 | Thramann et al. |
| 2005/0027360 A1* | 2/2005 | Webb ................ A61B 17/1671 623/17.11 |
| 2005/0033433 A1 | 2/2005 | Michelson |
| 2005/0049593 A1 | 3/2005 | Duong et al. |
| 2005/0085913 A1 | 4/2005 | Fraser et al. |
| 2005/0101960 A1 | 5/2005 | Fiere et al. |
| 2005/0149191 A1 | 7/2005 | Cragg et al. |
| 2005/0159746 A1 | 7/2005 | Grab et al. |
| 2005/0177237 A1 | 8/2005 | Shappley et al. |
| 2005/0177245 A1 | 8/2005 | Leatherbury et al. |
| 2005/0192576 A1 | 9/2005 | Michelson |
| 2005/0277933 A1 | 12/2005 | Wall et al. |
| 2006/0074488 A1 | 4/2006 | Abdou |
| 2006/0122604 A1 | 6/2006 | Gorhan et al. |
| 2006/0200147 A1 | 9/2006 | Ensign et al. |
| 2006/0224241 A1 | 10/2006 | Butler et al. |
| 2006/0235403 A1 | 10/2006 | Blain |
| 2006/0235409 A1 | 10/2006 | Blain |
| 2006/0235418 A1 | 10/2006 | Gil et al. |
| 2006/0241597 A1 | 10/2006 | Mitchell et al. |
| 2006/0241616 A1 | 10/2006 | Konieczynski et al. |
| 2006/0247650 A1 | 11/2006 | Yerby et al. |
| 2007/0055252 A1 | 3/2007 | Blain et al. |
| 2007/0055373 A1 | 3/2007 | Hudgins et al. |
| 2007/0093897 A1* | 4/2007 | Gerbec ................. A61F 2/4611 600/431 |
| 2007/0123863 A1 | 5/2007 | Winslow et al. |
| 2007/0135814 A1 | 6/2007 | Farris |
| 2007/0213820 A1 | 9/2007 | Magerl et al. |
| 2007/0250166 A1 | 10/2007 | McKay |
| 2007/0255414 A1 | 11/2007 | Melkent et al. |
| 2007/0282446 A1 | 12/2007 | Li |
| 2008/0103598 A1 | 5/2008 | Trudeau et al. |
| 2008/0161925 A1 | 7/2008 | Brittan et al. |
| 2008/0167686 A1 | 7/2008 | Trieu et al. |
| 2008/0177390 A1 | 7/2008 | Mitchell et al. |

(56) References Cited

U.S. PATENT DOCUMENTS

| | | |
|---|---|---|
| 2009/0072006 A1 | 3/2009 | Clauson et al. |
| 2009/0082819 A1 | 3/2009 | Blain et al. |
| 2009/0182430 A1 | 7/2009 | Tyber et al. |
| 2009/0198339 A1 | 8/2009 | Kleiner et al. |
| 2009/0270929 A1 | 10/2009 | Suddaby |
| 2010/0069960 A1 | 3/2010 | Chaput |
| 2010/0070037 A1 | 3/2010 | Parry et al. |
| 2011/0015744 A1 | 1/2011 | Squires et al. |
| 2011/0015745 A1 | 1/2011 | Bucci |
| 2011/0040384 A1 | 2/2011 | Junn et al. |
| 2011/0106259 A1 | 5/2011 | Lindenmann et al. |
| 2011/0153020 A1 | 6/2011 | Abdelgany et al. |
| 2011/0172775 A1 | 7/2011 | Flickinger et al. |
| 2011/0224796 A1 | 9/2011 | Weiland et al. |
| 2011/0282453 A1 | 11/2011 | Greenhalgh et al. |
| 2012/0016480 A1 | 1/2012 | Gerber et al. |
| 2012/0029636 A1 | 2/2012 | Ragab et al. |
| 2012/0046749 A1 | 2/2012 | Tatsumi |
| 2012/0197402 A1 | 8/2012 | Blackwell et al. |
| 2012/0277801 A1 | 11/2012 | Marik et al. |
| 2013/0030529 A1 | 1/2013 | Hunt |
| 2013/0110238 A1 | 5/2013 | Lindemann et al. |
| 2013/0110248 A1 | 5/2013 | Zipnick |
| 2013/0123923 A1 | 5/2013 | Pavlov et al. |
| 2013/0158669 A1* | 6/2013 | Sungarian ............... A61F 2/447 623/17.16 |
| 2013/0173003 A1* | 7/2013 | Matthis ................. A61F 2/4465 623/17.16 |
| 2013/0181015 A1 | 7/2013 | Cason |
| 2013/0197643 A1 | 8/2013 | Greenberg et al. |
| 2013/0268078 A1 | 10/2013 | Richelsoph |
| 2013/0297024 A1 | 11/2013 | Khurana |
| 2013/0325129 A1 | 12/2013 | Huang |
| 2014/0012318 A1 | 1/2014 | Goel |
| 2014/0066758 A1 | 3/2014 | Marik et al. |
| 2014/0094922 A1 | 4/2014 | Abdou |
| 2014/0309741 A1 | 10/2014 | Ganter et al. |
| 2014/0324173 A1 | 10/2014 | Kirschman |
| 2015/0173917 A1 | 6/2015 | Radcliffe et al. |
| 2015/0190242 A1* | 7/2015 | Blain ..................... A61F 2/447 623/17.12 |
| 2015/0342648 A1 | 12/2015 | McCormack et al. |
| 2016/0000576 A1 | 1/2016 | Kirschman |
| 2016/0022438 A1 | 1/2016 | Lamborne et al. |
| 2016/0120660 A1 | 5/2016 | Melkent et al. |
| 2016/0213485 A1 | 7/2016 | Schaufler et al. |
| 2016/0296338 A1 | 10/2016 | Kim et al. |
| 2017/0056201 A1 | 3/2017 | Liang et al. |
| 2017/0231782 A1 | 8/2017 | Perez-Cruet et al. |
| 2017/0333205 A1 | 11/2017 | Joly et al. |
| 2018/0014947 A1 | 1/2018 | Baynham |
| 2018/0104063 A1 | 4/2018 | Asaad |
| 2018/0214279 A1 | 8/2018 | Etminan et al. |
| 2018/0235769 A1 | 8/2018 | Levy et al. |
| 2018/0250051 A1 | 9/2018 | Vrionis et al. |
| 2018/0289508 A1 | 10/2018 | Glerum |
| 2018/0325693 A1* | 11/2018 | Weiman ............... A61F 2/4465 |
| 2019/0046333 A1* | 2/2019 | Hansell .................. A61B 90/39 |
| 2019/0091036 A1 | 3/2019 | Levy et al. |
| 2019/0133785 A1 | 5/2019 | Georges |
| 2019/0175357 A1 | 6/2019 | Sharabani |
| 2019/0254840 A1 | 8/2019 | Gray et al. |
| 2020/0000608 A1 | 1/2020 | Bullard et al. |
| 2020/0085586 A1 | 3/2020 | Ludwig et al. |
| 2020/0093612 A1 | 3/2020 | Blain et al. |
| 2020/0146729 A1 | 5/2020 | Blain et al. |
| 2020/0197149 A1 | 6/2020 | Folger et al. |
| 2020/0229943 A1 | 7/2020 | Abdou |
| 2020/0315679 A1 | 10/2020 | Vrionis et al. |
| 2020/0345503 A1 | 11/2020 | Sansur et al. |
| 2020/0345505 A1 | 11/2020 | Etminan et al. |
| 2021/0000608 A1 | 1/2021 | Blain et al. |
| 2021/0137702 A1 | 5/2021 | Neubardt |
| 2021/0145600 A1 | 5/2021 | Sharifi-Mehr et al. |
| 2021/0145607 A1 | 5/2021 | Kuyler et al. |
| 2021/0154021 A1 | 5/2021 | Bae et al. |
| 2022/0192841 A1 | 6/2022 | Blain et al. |
| 2022/0241089 A1 | 8/2022 | Clauss et al. |
| 2022/0346843 A1 | 11/2022 | Blain et al. |
| 2022/0387189 A1 | 12/2022 | Blain et al. |
| 2023/0165690 A1 | 6/2023 | Blain et al. |

FOREIGN PATENT DOCUMENTS

| | | |
|---|---|---|
| DE | 30 27 138 | 12/1981 |
| DE | 30 27 148 | 12/1981 |
| DE | 297 01 099 | 4/1997 |
| DE | 197 02 201 | 8/1998 |
| DE | 20 2004 015 912 | 12/2004 |
| EP | 0 242 842 | 10/1987 |
| EP | 0 974 319 | 1/2000 |
| EP | 1 029 510 | 8/2000 |
| EP | 1 346 697 | 9/2003 |
| EP | 1 470 803 | 10/2004 |
| FR | 2 766 353 | 1/1999 |
| FR | 2 813 519 | 3/2002 |
| FR | 2 859 904 | 3/2005 |
| JP | 2002-515287 | 5/2002 |
| JP | 2003-518977 | 6/2003 |
| JP | 2004-500156 | 1/2004 |
| JP | 2008-522787 | 7/2008 |
| JP | 2008-537498 | 9/2008 |
| JP | 2010-510852 | 4/2010 |
| JP | 2014-523751 | 9/2014 |
| JP | 2015-500701 | 1/2015 |
| WO | WO 88/003781 | 6/1988 |
| WO | WO 89/004150 | 5/1989 |
| WO | WO 93/010725 | 6/1993 |
| WO | WO 94/000066 | 1/1994 |
| WO | WO 95/035067 | 12/1995 |
| WO | WO 00/024343 | 5/2000 |
| WO | WO 01/003570 | 1/2001 |
| WO | WO 01/049191 | 7/2001 |
| WO | WO 01/078615 | 10/2001 |
| WO | WO 01/089428 | 11/2001 |
| WO | WO 03/017856 | 3/2003 |
| WO | WO 03/071966 | 9/2003 |
| WO | WO 2004/006792 | 1/2004 |
| WO | WO 2005/027760 | 3/2005 |
| WO | WO 2006/020464 | 2/2006 |
| WO | WO 2017/075079 | 5/2017 |
| WO | WO 2020/219789 | 10/2020 |
| WO | WO 2021/055363 | 3/2021 |

OTHER PUBLICATIONS

Official Communication in Australian Application No. 2012211502, dated Jul. 17, 2013.
Notice of Acceptance in Australian Application No. 2012211502, dated Sep. 10, 2014.
Official Communication in Australian Application No. 2014274519, dated Sep. 17, 2015.
Official Communication in Australian Application No. 2014274519, dated Jun. 17, 2016.
Official Communication in Australian Application No. 2014274519, dated Aug. 26, 2016.
Notice of Acceptance in Australian Application No. 2014274519, dated Sep. 22, 2016.
Official Communication in Australian Application No. 2016277588, dated Sep. 7, 2017.
Official Communication in Australian Application No. 2018271345, dated Jul. 31, 2019.
Official Communication in European Application No. 06738204.4, dated Mar. 26, 2009.
Official Communication in European Application No. 06738204.4, dated Apr. 6, 2010.
Official Communication in European Application No. 06738204.4, dated Apr. 5, 2011.
Official Communication in European Application No. 06738204.4, dated Oct. 28, 2011.

(56) References Cited

OTHER PUBLICATIONS

Official Communication in European Application No. 06738204.4, dated Jul. 18, 2012.
Official Communication in European Application No. 06738204.4, dated Oct. 14, 2013.
Extended European Search Report for European Application No. 11160061.5, dated Nov. 2, 2011.
Official Communication in European Application No. 11160061.5, dated Jul. 9, 2012.
Extended European Search Report for European Application No. 11160063.1, dated Nov. 2, 2011.
Official Communication in European Application No. 11160063.1, dated Jul. 12, 2012.
Official Communication in European Application No. 11160063.1, dated Nov. 27, 2012.
Official Communication in European Application No. 11160063.1, dated Oct. 14, 2013.
Official Communication in European Application No. 14190344.3, dated Feb. 10, 2015.
Official Communication in European Application No. 14190344.3, dated Jan. 4, 2016.
Official Communication in European Application No. 14190344.3, dated Sep. 8, 2016.
Official Communication in European Application No. 18150661.9, dated May 25, 2018.
Official Communication in European Application No. 18150661.9, dated Aug. 23, 2019.
Official Communication in Japanese Application No. 2008-501962, dated May 10, 2011.
Official Communication in Japanese Application No. 2008-501962, dated Nov. 13, 2012.
Official Communication in Japanese Application No. 2011-210533, dated Mar. 5, 2013.
Official Communication in Japanese Application No. 2011-210533, dated Dec. 3, 2013.
Notice of Allowance in Japanese Application No. 2011-210533, dated May 7, 2014.
Notice of Allowance in Japanese Application No. 2013-117602, dated May 7, 2014.
Notice of Allowance in Japanese Application No. 2013-117602, dated Feb. 2, 2015.
International Search Report and Written Opinion in International Application No. PCT/US2006/009120, dated Oct. 20, 2006.
International Preliminary Report on Patentability and Written Opinion in International Application No. PCT/US2006/009120, dated Sep. 18, 2007.
Official Communication in Australian Application No. 2016212009, dated Sep. 6, 2019.
Official Communication in Australian Application No. 2016212009, dated May 26, 2020.
Official Communication in Australian Application No. 2016212009, dated Jul. 14, 2020.
Official Communication in Austra2020281016lian Application No. 2016212009, dated Nov. 24, 2021.
Official Communication in European Application No. 16743832.4, dated Jul. 24, 2018.
Official Communication in Japanese Application No. 2017-557269, dated Oct. 21, 2019.
Official Communication in Japanese Application No. 2017-557269, dated Jul. 13, 2020.
Official Communication in Japanese Application No. 2017-557269, dated Nov. 1, 2021.
Official Communication in Japanese Application No. 2020-181320, dated Sep. 21, 2021.
International Search Report and Written Opinion in International Application No. PCT/US2016/013062, dated Mar. 16, 2016.
International Preliminary Report on Patentability and Written Opinion in International Application No. PCT/US2016/013062, dated Aug. 10, 2017.
Invitation to Pay Additional Search Fees in International Application No. PCT/US2019/052211, dated Nov. 14, 2019.
International Search Report and Written Opinion in International Application No. PCT/US2019/052211, dated Feb. 3, 2020.
International Preliminary Report on Patentability and Written Opinion in International Application No. PCT/US2019/052211, dated Apr. 1, 2021.
International Search Report and Written Opinion in International Application No. PCT/US2021/072334, dated Mar. 18, 2022.
International Search Report and Written Opinion in International Application No. PCT/US2021/072934, dated Feb. 24, 2022.
Invitation to Pay Additional Search Fees in International Application No. PCT/US2021/072334, dated Jan. 13, 2022.
Official Communication in Canadian Application No. 2,972,788, dated Jan. 31, 2022.
Official Communication in European Application No. 18150661.9, dated Jan. 18, 2023.
Official Communication in Australian Application No. 2020281016, dated Aug. 26, 2022.
Official Communication in Australian Application No. 2020281016, dated Oct. 7, 2022.
Official Communication in Australian Application No. 2020281016, dated Nov. 16, 2022.
Official Communication in Australian Application No. 2020281016, dated Nov. 23, 2022.
Official Communication in Canadian Application No. 2,972,788, dated Oct. 31, 2022.
Official Communication in European Application No. 16743832.4, dated Jan. 26, 2023.
Official Communication in Japanese Application No. 2020-181320, dated Feb. 13, 2023.
Official Communication in European Application No. 19862906.5, dated Sep. 23, 2022.
International Search Report and Written Opinion in International Application No. PCT/US2022/050050, dated Feb. 22, 2023.

\* cited by examiner

CURVED EXPANDABLE INTERBODY DEVICES AND DEPLOYMENT TOOLS

CROSS-REFERENCE TO RELATED APPLICATIONS

This application claims priority benefit to U.S. Provisional Patent Application No. 63/116,060, filed Nov. 19, 2020, and U.S. Provisional Patent Application No. 63/179,420, filed Apr. 25, 2021, each of which is incorporated herein by reference in its entirety for all purposes.

BACKGROUND

Field

The present disclosure generally relates to the field of spinal orthopedics, and more particularly to curved expandable spinal implants for placement in intervertebral spaces between adjacent vertebrae and deployment tools for the placement of curved expandable spinal implants.

Description of the Related Art

The spine is a flexible structure that extends from the base of the skull to the tailbone. The weight of the upper body is transferred through the spine to the hips and the legs. The spine contains a plurality of bones called vertebrae. The vertebrae are hollow and stacked one upon the other, forming a strong hollow column for support. The hollow core of the spine houses and protects the nerves of the spinal cord. The spine is held upright through the work of the back muscles, which are attached to the vertebrae. While the normal spine has no side-to-side curve, it does have a series of front-to-back curves, giving it a gentle "S" shape.

Each vertebra is separated from the vertebra above or below by a cushion-like, fibrocartilage called an intervertebral disc. The discs act as shock absorbers, cushioning the spine, and preventing individual bones from contacting each other. In addition, intervertebral discs act as a ligament that holds vertebrae together. Intervertebral discs also work with the facet joint to allow for slight movement of the spine. Together, these structures allow the spine to bend, rotate and/or twist.

The spinal structure can become damaged as a result of degeneration, dysfunction, disease and/or trauma. More specifically, the spine may exhibit disc collapse, abnormal curvature, asymmetrical disc space collapse, abnormal alignment of the vertebrae and/or general deformity, which may lead to imbalance and tilt in the vertebrae. This may result in nerve compression, disability and overall instability and pain. If the proper shaping and/or curvature are not present due to scoliosis, neuromuscular disease, cerebral palsy, or other disorder, it may be necessary to straighten or adjust the spine into a proper curvature with surgery to correct these spinal disorders.

Surgical treatments may involve manipulation of the spinal column by attaching a corrective device, such as rods, wires, hooks or screws, to straighten abnormal curvatures, appropriately align vertebrae of the spinal column and/or reduce further rotation of the spinal column. The correct curvature is obtained by manipulating the vertebrae into their proper position and securing that position with a rigid system of screws and rods. The screws may be inserted into the pedicles of the vertebrae to act as bone anchors, and the rods may be inserted into heads of the screws. Two rods may run substantially parallel to the spine and secure the spine in the desired shape and curvature. The rods, which are shaped to mimic the correct spinal curvature, force the spine into proper alignment. Bone grafts are then placed between the vertebrae and aid in fusion of the individual vertebrae together to form a correctly aligned spine.

Other ailments of the spine result in degeneration of the spinal disc in the intervertebral space between adjacent vertebrae. Disc degeneration can cause pain and other complications. Conservative treatment can include non-operative treatment requiring patients to adjust their lifestyles and submit to pain relievers and a level of underlying pain. Operative treatment options include disc removal. This can relieve pain in the short term, but also often increases the risk of long-term problems and can result in motor and sensory deficiencies resulting from the surgery. Disc removal and more generally disc degeneration disease are likely to lead to a need for surgical treatment in subsequent years. The fusion or fixation will minimize or substantially eliminate relative motion between the fixed or fused vertebrae. In surgical treatments, interbody implants may be used to correct disc space collapse between adjacent vertebra, resulting in spinal fusion of the adjacent vertebra.

A fusion is a surgical method wherein two or more vertebrae are joined together (fused) by way of interbody implants, sometimes with bone grafting, to form a single bone. The current standard of care for interbody fusion requires surgical removal of all or a portion of the intervertebral disc. After removal of the intervertebral disc, the interbody implant is implanted in the interspace. In many cases, the fusion is augmented by a process called fixation. Fixation refers to the placement of screws, rods, plates, or cages to stabilize the vertebrae so that fusion can be achieved.

Interbody implants must be inserted into the intervertebral space in the same dimensions as desired to occupy the intervertebral space after the disc is removed. This requires that an opening sufficient to allow the interbody implant must be created through surrounding tissue to permit the interbody implant to be inserted into the intervertebral space. In some cases, the intervertebral space may collapse prior to insertion of the interbody implant. In these cases, additional hardware may be required to increase the intervertebral space prior to insertion of the implant.

In addition, minimally invasive surgical techniques have been used on the spine. Under minimally invasive techniques, access to the intervertebral space is taken to reach the spine through small incisions. Through these incisions, discs are removed and an interbody implant is placed in the intervertebral disc space to restore normal disc height. Minimally invasive spine surgery offers multiple advantages as compared to open surgery. Advantages include: minimal tissue damage, minimal blood loss, smaller incisions and scars, minimal post-operative discomfort, and relative quick recovery time and return to normal function.

SUMMARY

It would be desirable to insert a curved interbody device with a first smaller dimension into an intervertebral space and once in place, deploy to a second, relatively larger dimension to occupy the intervertebral space. This first smaller dimension can permit the use of minimally invasive surgical techniques for easy access to the intervertebral space, which can cause less disruption of soft and boney tissue in order to get to the intervertebral space. The curved expandable interbody device may be implanted with or without the need of additional hardware.

Disclosed are curved expandable interbody devices that are configured to have an initial collapsed configuration having a first height suitable for being inserted into an intervertebral space between a pair of adjacent vertebrae, and an expanded configuration having a second height that is greater than the first height. The curved expandable interbody devices can be expanded from the initial collapsed configuration to the expanded configuration in-situ. The expanded configuration can provide support to the adjacent vertebrae while bone fusion occurs and can also provide rigid support between the adjacent vertebrae that withstands compressive forces. In some configurations, the curved expandable interbody device can help increase the distance or height between the adjacent vertebrae. By inserting the curved expandable interbody device in the initial collapsed configuration into the intervertebral space, it is possible to perform the surgery percutaneously with minimal disruption to tissues surrounding the surgical site and intervening soft tissue structures. The curved expandable interbody device can be implanted through a minimally invasive or an open wound procedure.

In some embodiments, a curved expandable interbody device for placement between vertebrae is provided. The curved expandable interbody device can include an upper structure configured to abut a superior vertebra. The curved expandable interbody device can include a lower structure configured to abut an inferior vertebra. The curved expandable interbody device can include a screw mechanism between the upper structure and the lower structure. In some embodiments, the screw mechanism comprises a proximal portion, a distal portion, and a coupler. In some embodiments, the coupler comprises a central portion at least partially between the proximal portion and the distal portion. In some embodiments, the coupler further comprises a proximal interface comprising an upper connector and a lower connector. In some embodiments, the proximal portion and the distal portion are configured to rotate as a unit to change a distance between the proximal portion and the distal portion from a first length to a second length. In some embodiments, the upper structure and the upper connector form an upper curved slot therebetween and the lower structure and the lower connector form a lower curved slot therebetween.

In some embodiments, the proximal portion comprises a frustoconical surface configured to wedge between the upper structure and the lower structure, and wherein the distal portion comprises a frustoconical surface configured to wedge between the upper structure and the lower structure to change a distance between the upper structure and the lower structure from a first height to a second height. In some embodiments, the proximal portion comprises first threads wound in a first direction configured to engage a proximal threaded hole in the coupler, and wherein the distal portion comprises second threads wound in a second direction, opposite the first direction, configured to engage a distal threaded hole in the coupler. In some embodiments, the first threads and the second threads have an equal pitch, such that when the screw mechanism is actuated, a proximal end of the curved expandable interbody device changes height at a same rate as a distal end of the interbody device. In some embodiments, the curved expandable interbody device is configured to expand 3 mm from an initial collapsed height. In some embodiments, one or more of the upper structure and the lower structure further comprise a plurality of protrusions. In some embodiments, one or more of the upper structure and the lower structure comprise vertebrae engagement surfaces with a porous or roughened surface. In some embodiments, the vertebrae engagement surfaces comprise a titanium coating. In some embodiments, the proximal portion comprises a drive interface configured to be engaged by a deployment tool to rotate the proximal portion and the distal portion. In some embodiments, the distal portion comprises a keyed shaft configured to slideably engage with a matching keyed bore on the proximal portion. In some embodiments, the upper structure and the lower structure comprise a right side and a left side when viewed from the top, wherein the left side is concave. In some embodiments, the upper structure and the lower structure comprise a right side and a left side when viewed from the top, wherein the right side is convex. In some embodiments, the coupler further comprises at least one anti-rotational feature configured to engage the upper structure or the lower structure to prevent the coupler from rotating when the proximal portion and the distal portion are rotated.

In some embodiments, a system is provided comprising a curved expandable interbody device and a deployment tool.

In some embodiments, the upper curved slot and the lower curved slot are configured to be engaged by the deployment tool to lock the deployment tool to the curved expandable interbody device. In some embodiments, the upper and lower curved slot are configured to allow pivoting of the deployment tool relative to the curved expandable interbody device. In some embodiments, the upper and lower curved slot are configured to allow pivoting of the deployment tool in the direction of the concave surface of the curved expandable interbody device.

In some embodiments, a method is provided. The method can include coupling a deployment tool to a curved expandable interbody device. The method can include positioning the curved expandable interbody device between the superior vertebra and the inferior vertebra. The method can include pivoting the deployment tool and the curved expandable interbody device relative to each other to further position the curved expandable interbody device between the superior vertebra and the inferior vertebra. The method can include rotating the screw mechanism to expand the curved expandable interbody device.

In some embodiments, coupling the deployment tool to the curved expandable interbody device comprises coupling the deployment tool in a locked, straight position relative to the curved expandable interbody device. In some embodiments pivoting the deployment tool relative to the curved expandable interbody device comprises pivoting the deployment tool to a pivoted position of a plurality of pivoted positions.

DETAILED DESCRIPTION

Figure 1:
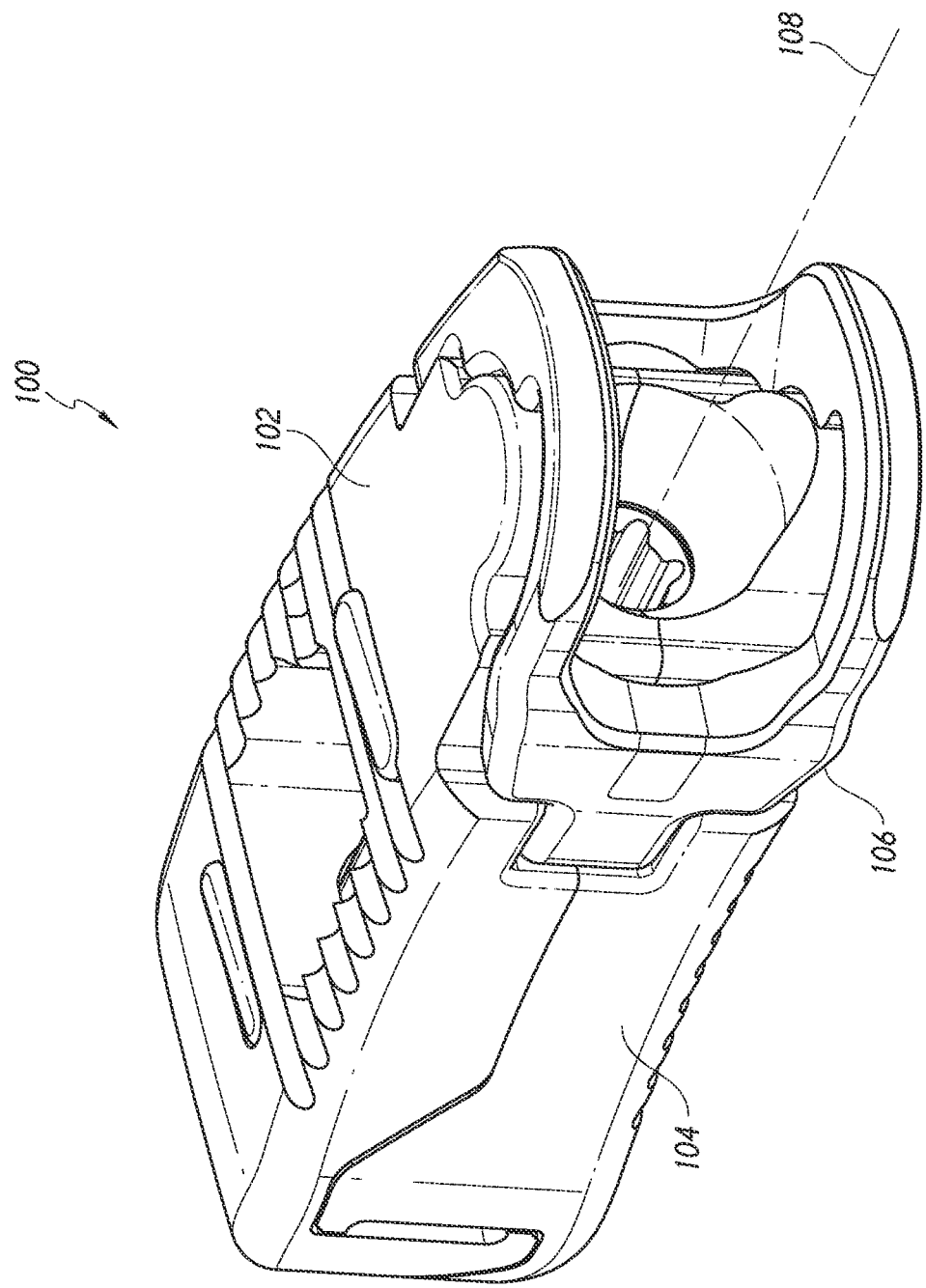
FIG. 1 is a perspective view showing an embodiment of a curved expandable interbody device in a collapsed configuration.

Curved expandable interbody devices can be configured to have an initial collapsed configuration having a first height suitable for being inserted into an intervertebral space between a pair of adjacent vertebrae, and an expanded configuration having a second height that is greater than the first height. The implant can be expanded from the initial collapsed configuration to the expanded configuration in-situ. The use of a small curved interbody implant which may be expanded in-situ allows the possibility of performing the surgery percutaneously with minimal disruption to tissues surrounding the surgical site and intervening soft tissue structures, through a minimally invasive or open procedure. The curved expandable interbody device can include features that reduce displacement of soft tissue and structures during placement of the curved expandable interbody device while providing support after placement to the adjacent vertebrae while bone fusion occurs. The curved expandable interbody device includes a collapsed configuration with dimensions that can allow insertion of the curved expandable interbody device between the vertebrae. Once the curved expandable interbody device is positioned in a desired location between the vertebrae, the curved expandable interbody device may be expanded to an expanded configuration. The curved expanded configuration can increase the distance or height between the adjacent vertebrae and provide support to the adjacent vertebrae while bone fusion occurs. The expanded configuration can also provide rigid support between the adjacent vertebrae that withstands compressive forces. The curved expandable interbody device may sometimes be referred to as a device, an implant, an expandable implant, a curved expandable interbody spacer or a curved expandable corpectomy device, all of which are envisioned for the present disclosure.

Several non-limiting embodiments will now be described with reference to the figures, wherein like numerals reflect like elements throughout. The terminology used in the description presented herein is not intended to be interpreted in any limited or restrictive way, simply because it is being utilized in conjunction with a detailed description of certain specific embodiments. Furthermore, some embodiments may include several novel features, no single one of which is solely responsible for its desirable attributes or which is essential to the devices and methods described herein.

The words proximal and distal are applied herein to denote specific ends of components of the instrument described herein. A proximal end refers to the end of a component nearer to an operator of the instrument when the instrument is being used. A distal end refers to the end of a component further from the operator and extending towards the surgical area of a patient and/or the implant. The words top, bottom, left, right, upper and lower are used herein to refer to sides of the device from the described point of view. These reference descriptions are not intended to limit the orientation of the implanted curved expandable interbody device. The curved expandable interbody device can be positioned in any functional orientation. For example, in some configurations, the curved interbody device can be used in an upside-down orientation from the specific orientation described herein.

Figure 2:
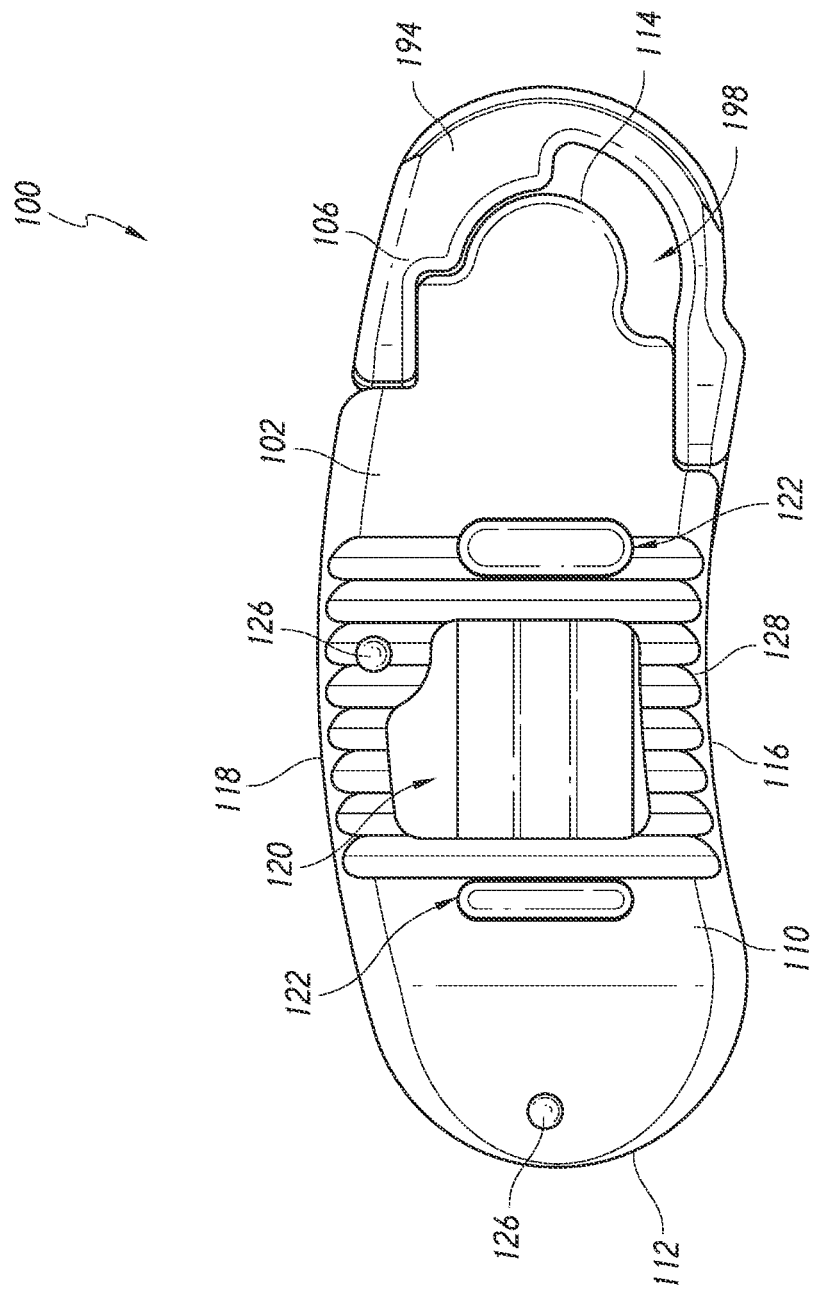
FIG. 2 is a top view of the curved expandable interbody device of FIG. 1.
Figure 3:
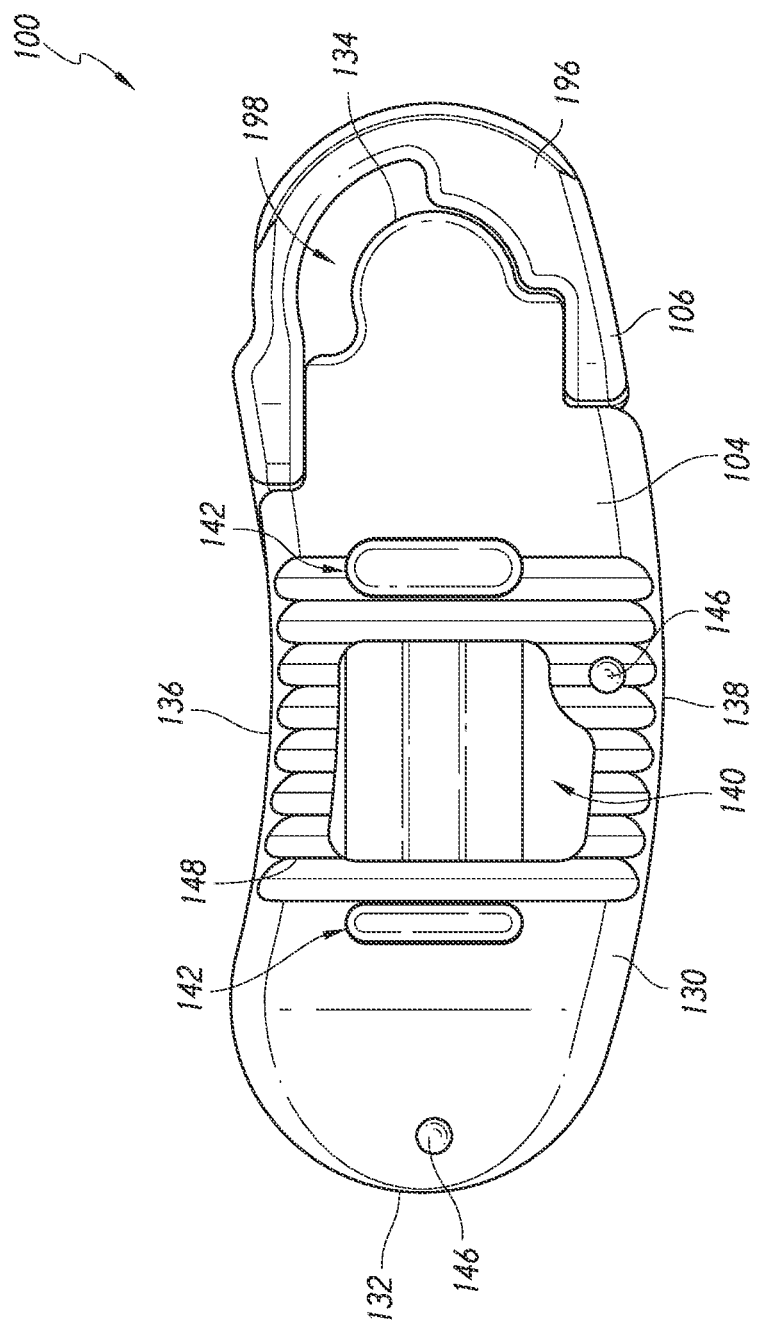
FIG. 3 is a bottom view of the curved expandable interbody device of FIG. 1.
Figure 4:
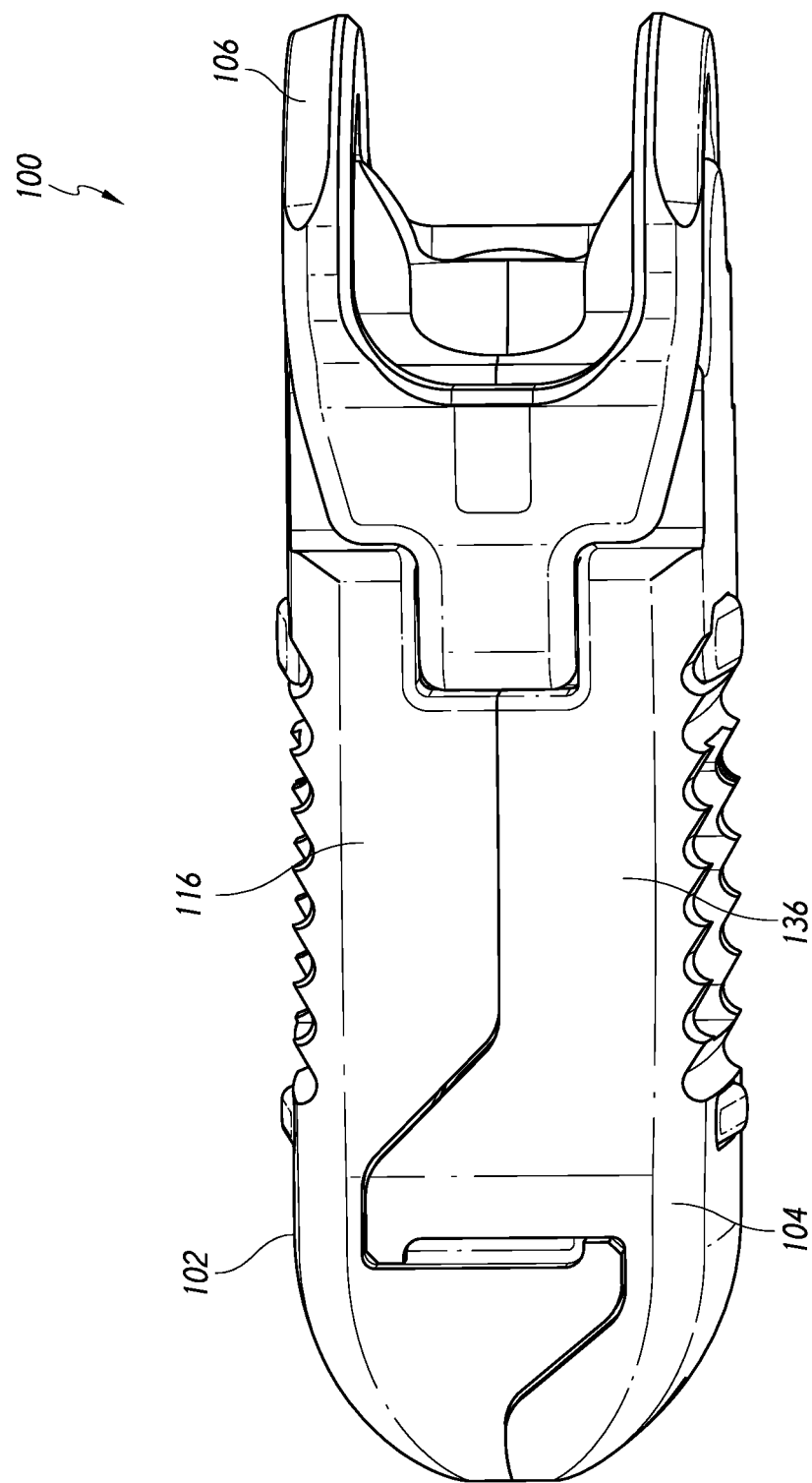
FIG. 4 is a left side view of the curved expandable interbody device of FIG. 1.
Figure 5:
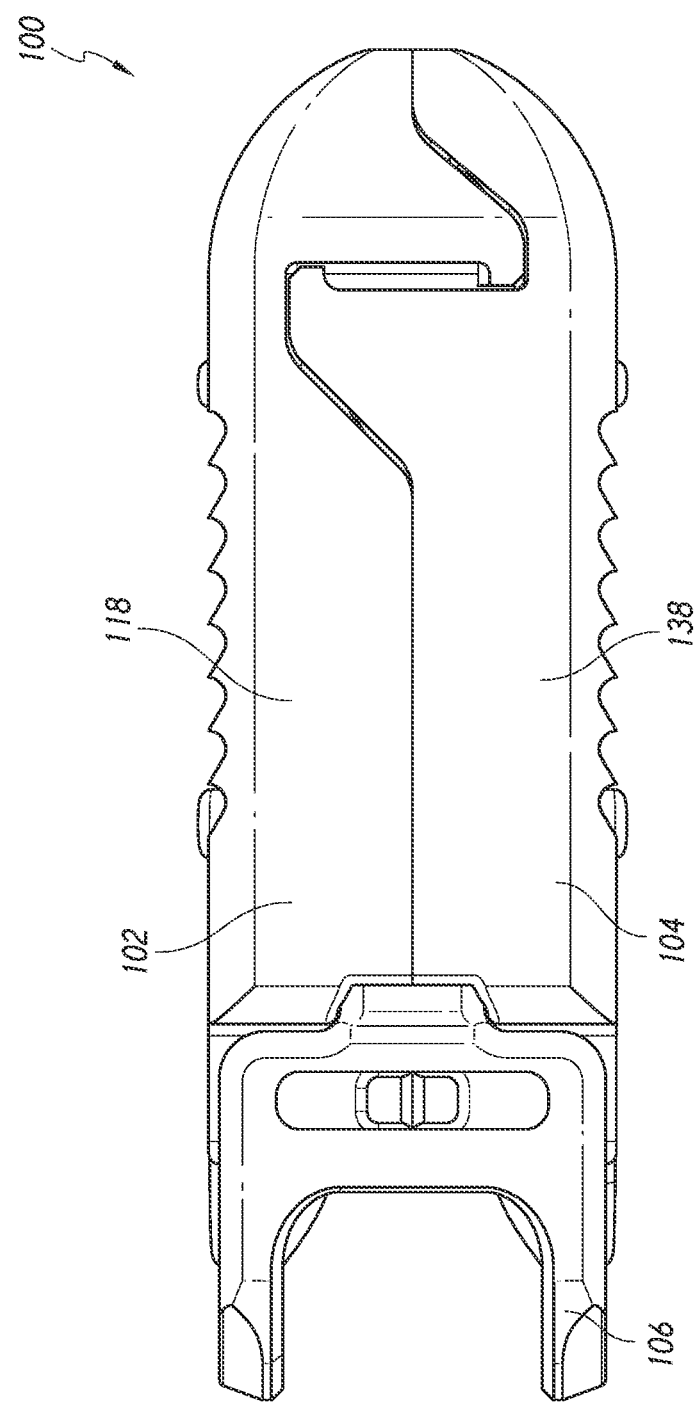
FIG. 5 is a right side view of the curved expandable interbody device of FIG. 1
Figure 7:
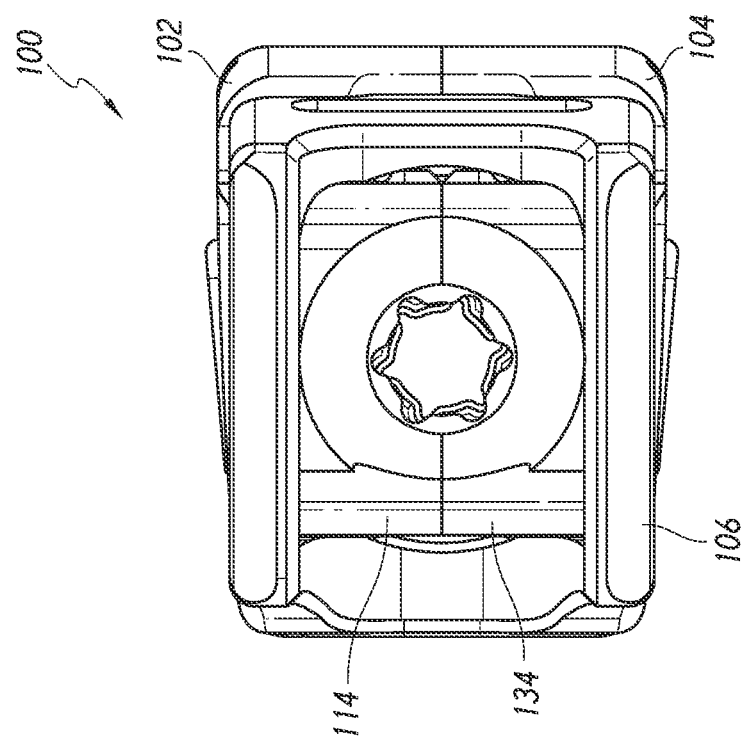
FIG. 7 is a rear view of the curved expandable interbody device of FIG. 1.
Figure 6:
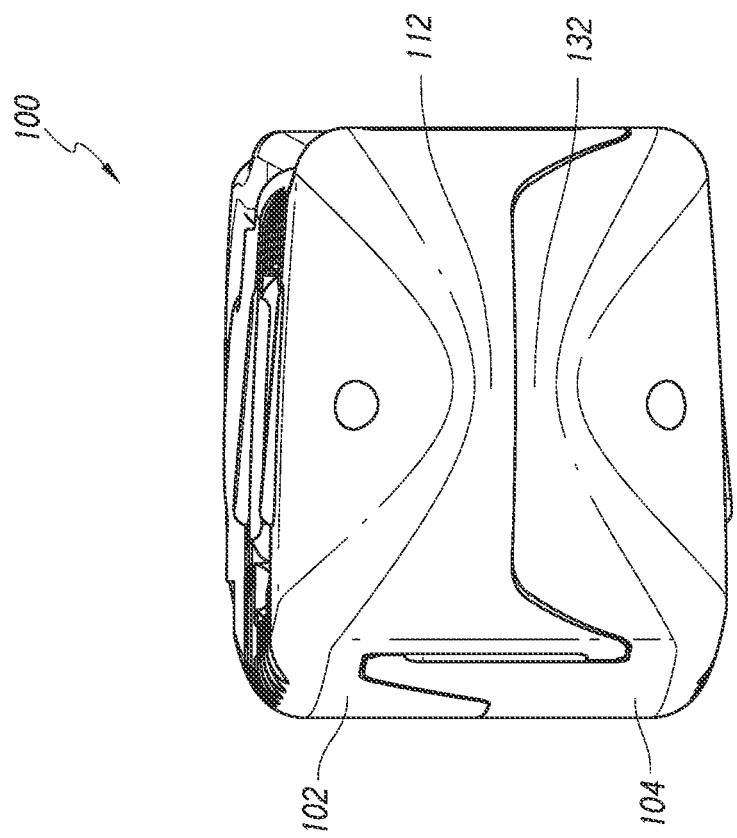
FIG. 6 is a front view of the curved expandable interbody device of FIG. 1.
Figure 8:
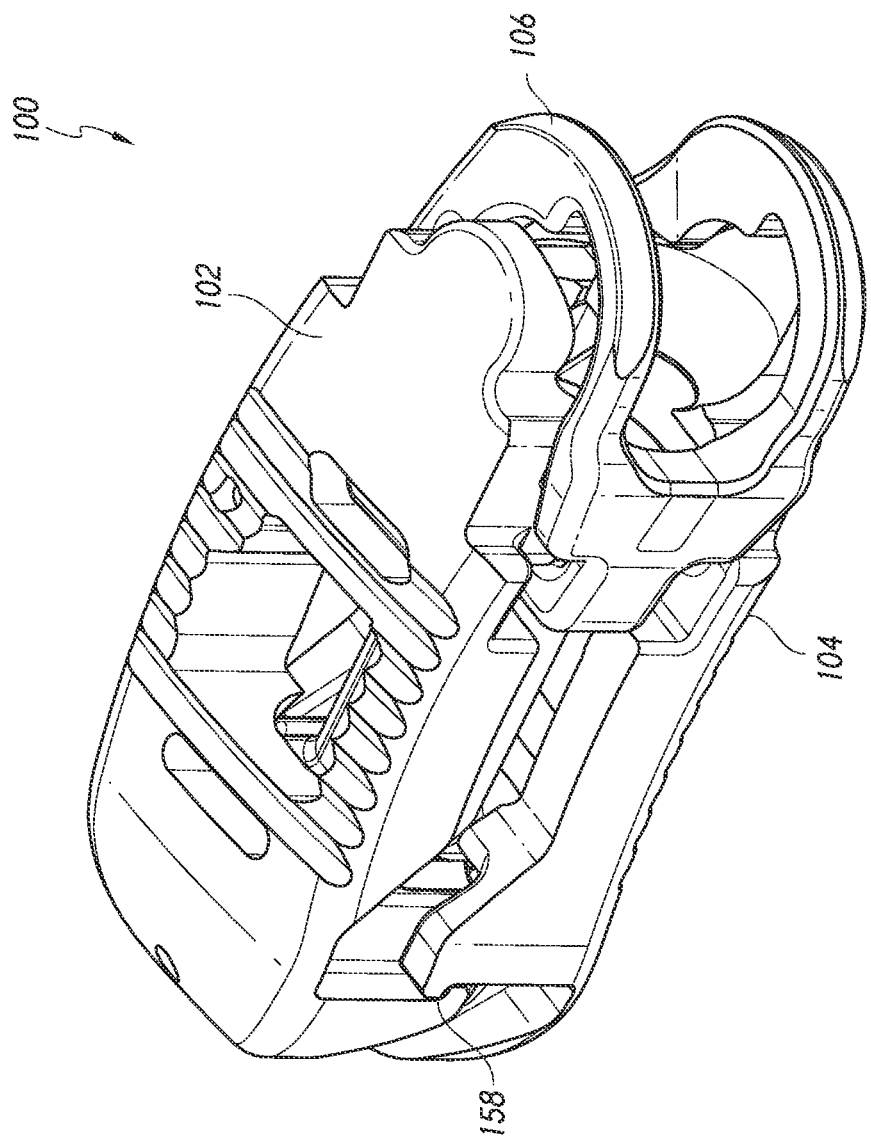
FIG. 8 is a perspective view showing the curved expandable interbody device of FIG. 1 in an expanded configuration.
Figure 9:
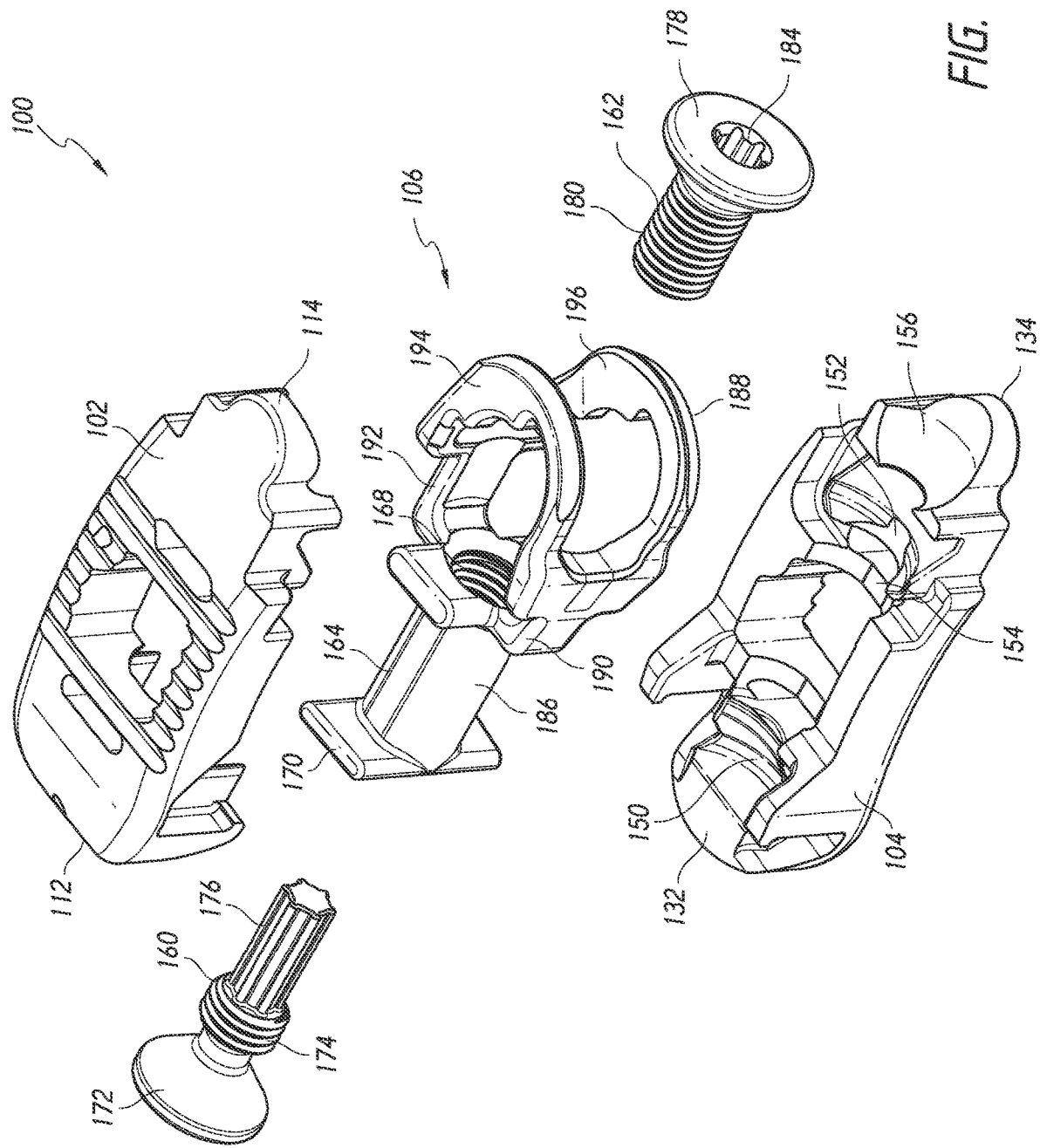
FIG. 9 is a perspective exploded view showing the curved expandable interbody device of FIG. 1.
Figure 10:
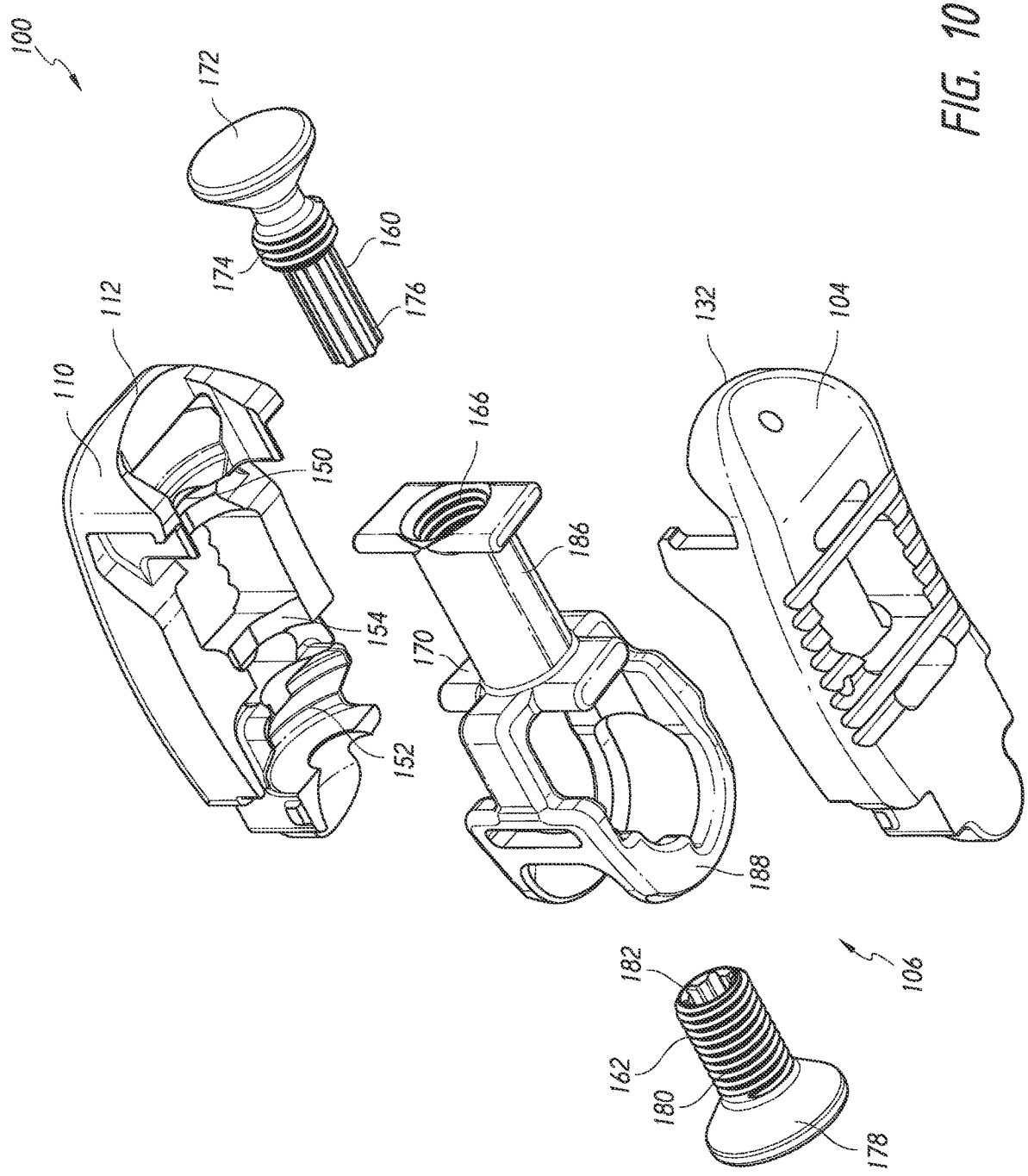
FIG. 10 is another perspective exploded view showing the curved expandable interbody device of FIG. 1.
Figure 11:
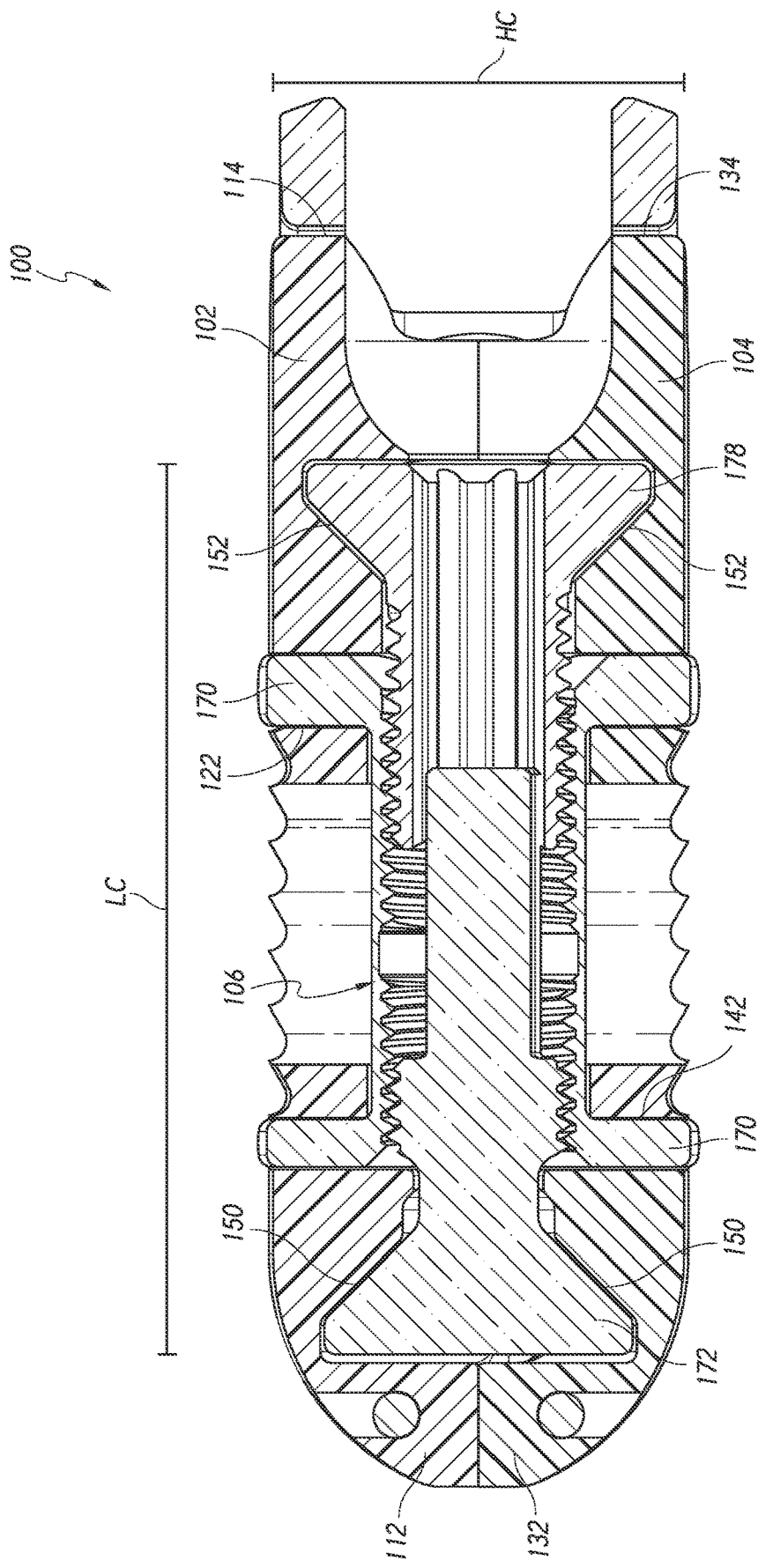
FIG. 11 is a cross-sectional view of the curved expandable interbody device of FIG. 1 in a collapsed configuration.
Figure 12:
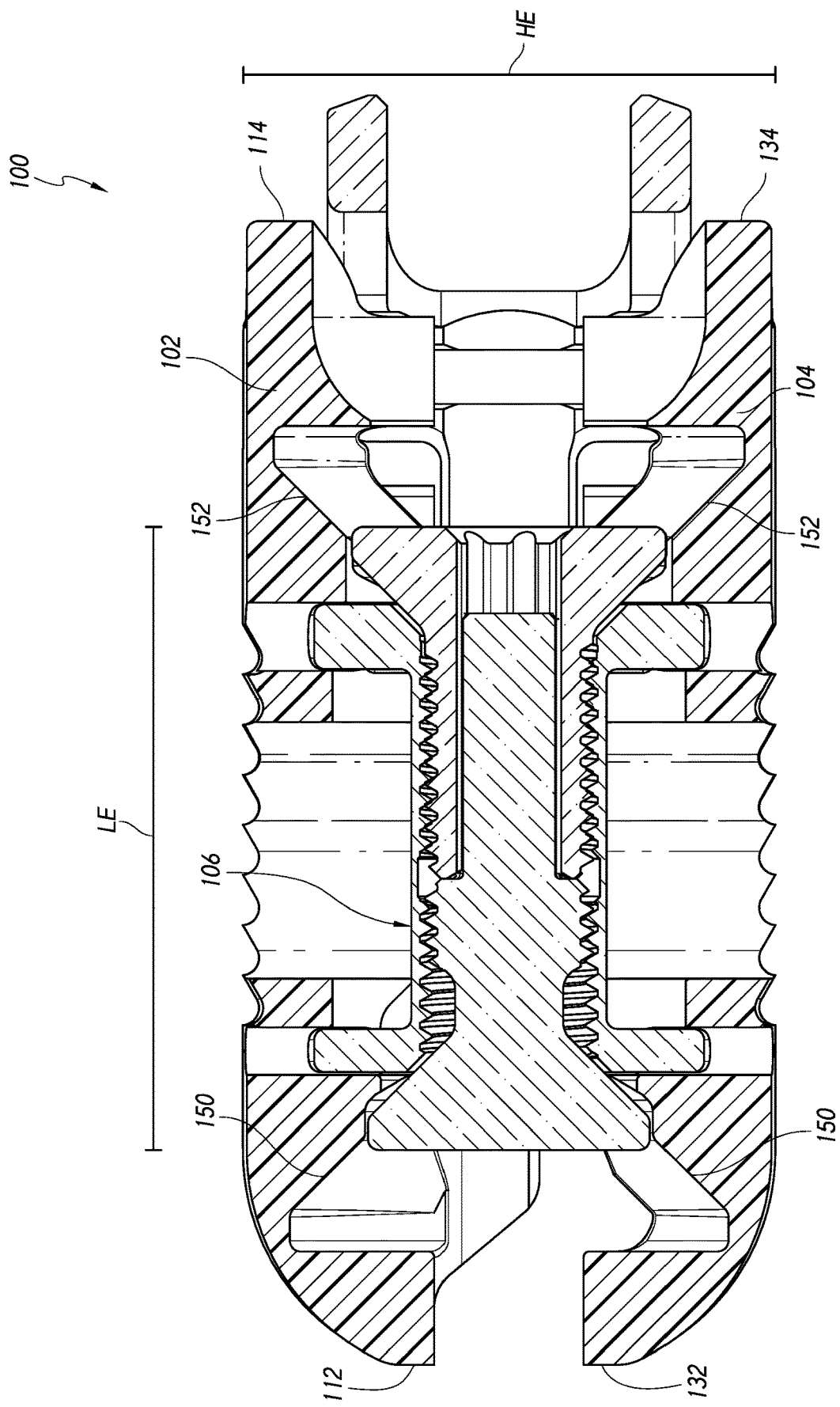
FIG. 12 is a cross-sectional view of the curved expandable interbody device of FIG. 1 in an expanded configuration.

FIGS. 1-12 illustrate a curved expandable interbody device 100. FIG. 1 is a perspective view. FIG. 2 is a top view. FIG. 3 is a bottom view. FIG. 4 is a left side view. FIG. 5 is a right side view. FIG. 6 is a front view. FIG. 7 is a rear view. FIG. 8 is a perspective view showing the curved expandable interbody device 100 in an expanded configuration. FIGS. 9-10 are perspective exploded views showing the curved expandable interbody device 100. FIG. 11 is a cross-sectional view of the curved expandable interbody device 100 in a collapsed configuration. FIG. 12 is a cross-sectional view of the curved expandable interbody device 100 in an expanded configuration. The expandable interbody device 100 can be configured to couple to a deployment tool 200 described in FIGS. 11-25.

Referring to FIG. 1, the curved expandable interbody device 100 can include an upper structure 102, a lower structure 104, and a screw mechanism 106. The upper structure 102 can include any of the features of the lower structure 104. The lower structure 104 can include any of the features of the upper structure 102. The curved expandable interbody device 100 can include a longitudinal axis 108. The longitudinal axis 108 can extend along the screw mechanism 106. The expandable interbody device 100 can be changeable between a collapsed configuration, as shown in FIG. 1, to an expanded configuration, as shown in FIG. 8.

Referring to FIG. 2, the upper structure 102 can include a top surface 110, a distal surface 112, a proximal surface 114, a left surface 116, and a right surface 118. The right and left orientation are taken when the curved expandable interbody device 100 is viewed from the top and from the proximal end. In some embodiments, the curved expandable interbody device 100 curves to the left. The left surface 116 can be concave. The right surface 118 can be convex. In some embodiments, the curved expandable interbody device 100 curves to the right. The right surface 118 can be concave. The left surface 116 can be convex.

In some embodiments, one or more openings 120 can extend through the upper structure 102. The upper structure 102 can have one central opening 120. The upper structure 102 can have a plurality of openings 120. The curved expandable interbody device 100 can facilitate fusion when the one or more openings 120 are packed with material, as described herein. The one or more openings 120 can be configured to receive fluids, medication, bone graft material, or other material to help in the integration of the interbody device with the vertebrae, such as with allograft and/or Demineralized Bone Matrix ("DBM") packing. In some embodiments, the upper structure 102 may not have any openings and the top surface 110 can be closed.

The upper structure 102 can include one or more alignment slots 122. The upper structure 102 can include two alignment slots 122. The upper structure 102 can include a distal alignment slot 122 positioned between the distal surface 112 and the opening 120. The upper structure 102 can include a proximal alignment slot 122 positioned between the proximal surface 114 and the opening 120. The alignment slots 122 can facilitate alignment between the screw mechanism 106 and the upper structure 102.

The upper structure 102 can have any size configured to be placed between vertebrae. The distal surface 112, the proximal surface 114, the left surface 116, and the right surface 118 may have a varying height. The distal surface 112, the proximal surface 114, the left surface 116, and the right surface 118 may have a varying length. The distal surface 112, the proximal surface 114, the left surface 116, and the right surface 118 may have a varying width. The distal surface 112, the proximal surface 114, the left surface 116, and the right surface 118 may have a varying wall thickness. The distal surface 112, the proximal surface 114, the left surface 116, and the right surface 118 may have a varying curvature radius.

In some embodiments, the upper structure 102 can have one or more markers 126 to help visualization using radiation during the implantation procedure. The one or more markers 126 can be made of a radiopaque material, such as titanium. The one or more markers 126 can be spherical. The one or more markers 126 can be inserted into lumens in the upper structure 102. The upper structure 102 can include a marker 126 near the distal surface 112. The upper structure 102 can include a marker near the right surface 118 when viewed from the top.

The top surface 110 of the upper structure 102 can have a roughened surface, such as a plurality of protrusions 128. The protrusions 128 can be configured to be spaced throughout the top surface 110 or a portion thereof. The protrusions 128 can be located near the opening 120 and the alignments slots 122. The protrusions 128 can be configured to have variable thickness, height, and width as well as angled surfaces. In some embodiments, the top surface 110 can have protrusions 128 that are angled toward the proximal surface 114. The distal facing side of the protrusions 128 can be less steep than the proximal facing side of the protrusions 128.

Referring to FIG. 3, the lower structure 104 can include a bottom surface 130, a distal surface 132, a proximal surface 134, a left surface 136, and a right surface 138. In some embodiments, the curved expandable interbody device 100 curves to the left. The left surface 136 can be concave. The right surface 138 can be convex. In some embodiments, the curved expandable interbody device 100 curves to the right. The right surface 138 can be concave. The left surface 136 can be convex.

In some embodiments, one or more openings 140 can extend through the lower structure 104. The lower structure 104 can have one central opening 140. The lower structure 104 can have a plurality of openings 140. The lower structure 104 can facilitate fusion when the one or more openings 140 are packed with material, as described herein. The one or more openings 120 of the upper structure 102 and the one or more openings 140 of the lower structure 104 can be aligned. The one or more openings 120 of the upper structure 102 and the one or more openings 140 of the lower structure 104 can form a lumen through the curved expandable interbody device 100. In some embodiments, the one or more openings 120 and the one or more openings 140 can extend through to the curved expandable interbody device 100 and can be used as an access location for delivering fluids, medication or other material, as disclosed herein. In some embodiments, the lower structure 104 may not have any openings and the bottom surface 130 can be closed.

The lower structure 104 can include one or more alignment slots 142. The lower structure 104 can include two alignment slots 142. The lower structure 104 can include a distal alignment slot 142 positioned between the distal surface 132 and the opening 140. The lower structure 104 can include a proximal alignment slot 142 positioned between the proximal surface 134 and the opening 140. The alignment slots 122 and the alignment slots 142 can be aligned. The alignment slots 142 can facilitate alignment between the screw mechanism 106 and the lower structure 104.

The lower structure 104 can have any size configured to be placed between vertebrae. The distal surface 132, the proximal surface 134, the left surface 136, and the right surface 138 may have a varying height. The distal surface 132, the proximal surface 134, the left surface 136, and the right surface 138 may have a varying length. The distal surface 132, the proximal surface 134, the left surface 136, and the right surface 138 may have a varying width. The distal surface 132, the proximal surface 134, the left surface 136, and the right surface 138 may have a varying wall thickness. The distal surface 132, the proximal surface 134, the left surface 136, and the right surface 138 may have a varying curvature radius.

In some embodiments, the lower structure 104 can have one or more markers 146 to help visualization using radiation during the implantation procedure. The one or more markers 146 can be made of a radiopaque material, such as titanium. The lower structure 104 can include a marker 146 near the distal surface 132. The lower structure 104 can include a marker near the right surface 138. The upper structure 102 and the lower structure 104 can include markers 126 that are aligned near the distal surfaces 112, 132. The upper structure 102 and the lower structure 104 can include markers 126 that are aligned near the right surfaces 118, 138.

The bottom surface 130 of the lower structure 104 can have a roughened surface, such as a plurality of protrusions 148. The protrusions 128 can be configured to be spaced throughout the bottom surface 130 or a portion thereof. The protrusions 148 can be located near the opening 140 and the alignments slots 142. The protrusions 148 can be configured to have variable thickness, height, and width as well as angled surfaces. In some embodiments, the bottom surface 130 can have protrusions 148 that are angled toward the proximal surface 134. The distal facing side of the protrusions 148 can be less steep than the proximal facing side of the protrusions 148.

The shape of the protrusions 128, 148 can allow for easy insertion of the curved expandable interbody device 100 and help prevent backing out of the device from the intervertebral space. The protrusions 128, 148 can be configured to provide additional support after the curved expandable interbody device 100 is implanted in the intervertebral space of the patient. For example, the friction between the vertebrae and the structures 102, 104 provided at least in part by the protrusions 128, 148 can help reduce movement of the curved expandable interbody device 100 in the intervertebral space.

Referring to FIG. 4, in some embodiments, the left surfaces 116, 136 align. The left surfaces 116, 136 can form a smooth concave side. The left surfaces 116, 136 can have the same radius of curvature. Referring to FIG. 5, in some embodiments, the right surfaces 118, 138 can align. The right surfaces 118, 138 can form a smooth convex side. The right surfaces 118, 138 can have the same radius of curvature. In some embodiments, the upper structure 102 and the lower structure 104 can have the same or similar perimeter. In some embodiments, the top surface 110 and the bottom surface 130 can be skewed relative to each other. The top surface 110 and the bottom surface 130 can be angled. In some embodiments, the top surface 110 and the bottom surface 130 can be parallel. The top surface 110 and the bottom surface 130 can be mirror images. The top surface 110 and the bottom surface 130 can be symmetrical.

Referring to FIG. 6, the distal surfaces 112, 132 can align. In some embodiments, the distal surfaces 112, 132 can form a smooth bullet shape. Referring to FIG. 7, the proximal surfaces 114, 134 can align. In some embodiments, the proximal surfaces 114, 134 can form a keyed shape as shown in FIG. 3. The keyed shape can be configured to interlock with a coupler of the screw mechanism 106 as described herein.

The upper structure 102 and lower structure 104, or portions thereof, can be made of any of a variety of materials known in the art, including but not limited to a polymer such as polyetheretherketone (PEEK), polyetherketoneketone (PEKK), polyethylene, fluoropolymer, hydrogel, or elastomer; a ceramic such as zirconia, alumina, or silicon nitride; a metal such as titanium, titanium alloy, cobalt chromium or stainless steel; or any combination of the above materials. The curved expandable interbody device 100 may be made of multiple materials in combination. The upper structure 102 and the lower structure 104 can be made of the same material. The upper structure 102 and the lower structure 104 can be made of different materials. For example, the upper structure 102 can comprise a first material such as a polymer, such as PEEK or polyethylene, and the lower structure 104 can comprise a second, different material such as a metal or ceramic.

In some embodiments, the upper structure 102 and/or the lower structure 104 may be formed of a porous material or have a roughened surface. The surfaces may be formed of a porous material, coated with a porous material, or chemically etched to form a porous or roughened surface with pores, which may help participate in the growth of bone with the adjacent vertebra. In some embodiments, only portions of the curved expandable interbody device 100 may be formed of a porous material, coated with a porous material, or chemically etched to form a porous surface. For example, at least some portions of the top surface 110 and/or the bottom surface 130 can be coated with a porous material, such as a titanium coating. FIG. 8 illustrates the coating. In some embodiments, the surface porosity may be at least approximately 50 microns and less than or equal to approximately 300 microns.

Referring to FIG. 8, the curved expandable interbody device 100 can expand. The upper structure 102 can be configured to slideably fit with the lower structure 104. The upper structure 102 and the lower structure 104 can have smooth surfaces at the interface between the structures. The upper structure 102 and the lower structure 104 can have smooth surfaces to form a slide bearing. In other embodiments, the upper structure 102 and lower structure 104 can have any of a plurality of different types of functional couplers to form a slideable connection.

Referring to FIGS. 9-10, the screw mechanism 106 is configured to expand the curved expandable interbody device 100. The upper structure 102 and the lower structure 104 can have one or more grooves 150, 152 that accepts the screw mechanism 106. In the illustrated embodiments, the upper structure 102 can include the groove 150 near the distal surface 112 and the groove 152 near the proximal surface 114. In the illustrated embodiments, the lower structure 104 can include the groove 150 near the distal surface 132 and the groove 152 near the proximal surface 134. The grooves 150 near the distal surfaces 112, 132 can form a cavity to accept a distal portion of the screw mechanism 106. The grooves 152 near the proximal surface 114, 134 can form a cavity to accept a proximal portion of the screw mechanism 106.

Referring to FIGS. 11-12, the grooves 150, 152 can have an angled surface. The grooves 150, 152 can be conical. The grooves 150 can flare outward toward the distal surfaces 112, 132. The grooves 150 can be larger near the distal surfaces 112, 132 than toward the middle. The grooves 152 can flare outward toward the proximal surfaces 114, 134. The grooves 152 can be larger near the proximal surface 114, 134 than toward the middle. When the upper structure 102 and the lower structure 104 are in the collapsed configuration as shown in FIG. 11, the grooves 150, 152 can form a frustoconical shape. The upper structure 102 can have approximately half of the cone and the lower structure 104 can have approximately half of the cone. The grooves 150, 152 can interface with the screw mechanism 106 to transition the curved expandable interbody device 100 from the collapsed to expanded configuration, as disclosed herein.

The upper structure 102 and the lower structure 104 can have one or more cavities 154 to receive the screw mechanism 106. The cavities 154 can be continuous with one or more grooves 150, 152. The cavities 154 can be continuous with one or more openings 120, 140. In some embodiments, the cavities 154 can be packed with material. In some embodiments, only the openings 120, 140 are packed with material. The cavities 154 can be larger than the corresponding components of the screw mechanism 106. In some embodiments, only the grooves 150, 152 contact movable components of the screw mechanism 106. In some embodiments, the cavities 154 do not contact movable components of the screw mechanism 106.

The cavities 154 can include one or more proximal cavities 156. The one or more proximal cavities 156 can receive the deployment tool 200 as described herein. The one or more proximal cavities 156 can be open on the proximal surfaces 114, 134. The one or more proximal cavities can be concave between the upper structure 102 and the lower structure 104. The one or more proximal cavities 156 can be semi-spherical. The one or more proximal cavities can be rounded inwards toward the middle. When the upper structure 102 and the lower structure 104 are in the collapsed configuration, the proximal cavities 156 can form a concave, semi-spherical shape. The upper structure 102 can have approximately half of the semi-sphere and the lower structure 104 can have approximately half of the semi-sphere. The one or more proximal cavities 156 can receive the deployment tool 200 to transition the curved expandable interbody device 100 from the collapsed to expanded configuration, as disclosed herein.

Referring back to FIG. 8, the upper structure 102 and the lower structure 104 can include a catch 158. The upper structure 102 and the lower structure 104 can be configured to expand vertically. The upper structure 102 and the lower structure 104 can move linearly apart from one another. The catch 158 can prevent additional expansion. In some embodiments, the upper structure 102 and the lower structure 104 can be configured to expand along a single axis. In some embodiments, the upper structure 102 and the lower structure 104 can be configured to expand without translation. In some embodiments, both the upper structure 102 and the lower structure 104 expand.

In some embodiments, the curved expandable interbody device 100 can have a slight inclination, called a lordosis angle. In some embodiments, the lordosis angle decreases the height of the curved expandable interbody device 100. In some embodiments, the height of the curved expandable interbody device 100 decreases near the left surface 116, 136 compared to the right surface 118, 138. In some embodiments, the lordosis angle is approximately 5 degrees. Other configurations are contemplated, for example 1 degree, 2 degrees, 3 degrees, 4 degrees, 5 degrees, 6 degrees, 7 degrees, 8 degrees, 9 degrees, 10 degrees, 11 degrees, 12 degrees, 13 degrees, 14 degrees, 15 degrees, 16 degrees, 17 degrees, 18 degrees, 19 degrees, 20 degrees, between 4 degrees and 6 degrees, between 0 degrees and 5 degrees, between 3 degrees and 5 degrees, between 8 degrees and 12 degrees, between 14 degrees and 16 degrees, or any range of two of the foregoing values. In some embodiments, the curved expandable interbody device 100 can be slightly enlarged at the convex surface. The right surface 118, 138 can be the maximum height of the curved expandable interbody device 100. The curved expandable interbody device 100 can taper slightly by the lordosis angle toward the concave surface. In some embodiments, the top surface 110 of the upper structure 102 can be tapered by the lordosis angle. In some embodiments, the bottom surface 130 of the lower structure 104 can be tapered by the lordosis angle. In some embodiments, both the top surface 110 and the bottom surface 130 taper toward the left. In some embodiments, both the top surface 110 and the bottom surface 130 taper toward the concave surface. In some embodiments, the curved expandable interbody device 100 can have a width measured from the maximum left surface to the maximum right surface. This width can be the total tangent envelop of the device. In some embodiments, the curved expandable interbody device 100 can have a width measured from the convex surface to the concave surface. In some embodiments, the curved expandable interbody device 100 can have a width of 6 mm, 8 mm, 10 mm, 12 mm, 13 mm, 14 mm, 15 mm, 16 mm, or any range of two of the foregoing values. In some embodiments, the curved expandable interbody device 100 can have a length measured from the maximum proximal surfaces to the maximum distal surfaces of the upper and lower structures 102, 104. In some embodiments, the length accounts for the upper and lower structures 102, 104 without the screw mechanism 106. In some embodiments, the length accounts for the upper and lower structures 102, 104 without the coupler 164. In some embodiments, the curved expandable interbody device 100 can have a length measured from the maximum distal surfaces of the upper and lower structures 102, 104 to the maximum proximal surfaces of the coupler 164. In some embodiments, the curved expandable interbody device 100 can have a length measured from the maximum distal surfaces of the upper and lower structures 102, 104 to the maximum proximal surfaces of the upper and lower connectors 194, 196. In some embodiments, the length of the curved expandable interbody device 100 includes the length of the coupler 164. In some embodiments, the curved expandable interbody device 100 can have a length of 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm, 41 mm, 42 mm, or any range of the foregoing values. In some embodiments, the curved expandable interbody device 100 can have a height of 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, or any range of the foregoing values. In some embodiments, the curved expandable interbody device 100 can have a width of 12 mm to 13 mm, a length of 27 mm to 37 mm, a height of 8 mm to 12 mm, an expansion of up to 4 mm, and a lordosis of 5 degrees to 15 degrees. Other configurations are contemplated.

Referring back to FIGS. 9-12, the screw mechanism 106 can include a distal section 160, a proximal section 162 and a coupler 164. The coupler 164 can have a distal opening 166 configured to engage the distal section 160. The coupler 164 can have a proximal opening 168 configured to engage the proximal section 162. The distal opening 166 and the proximal opening 168 can be threaded. The openings 166, 168 can have threads in opposite directions. In some embodiments, the distal opening 166 is left handed threads and the proximal opening 168 is right handed threads.

The coupler 164 can include alignment protrusions 170 configured to engage with alignment slots 122, 142 in the upper structure 102 and lower structure 104, respectively. The alignment protrusions 170 can prevent the coupler 164 from rotating as the proximal section 162 of the screw mechanism 106 is rotated with the deployment tool 200. The alignment protrusions 170 can facilitate smooth expansion along a single plane. The alignment protrusions 170 can prevent translation of the upper structure 102 relative to the lower structure 104 during expansion.

In the illustrated embodiment, the coupler 164 includes four alignment protrusions 170. The coupler 164 can include any number of alignment protrusions 170. The coupler 164 can include two alignment protrusions 170 configured to engage the upper structure 102 and two alignment protrusions 170 configured to engage the lower structure 104. The alignment protrusions 170 can be located to maximize the surface area of the openings 120, 140. The alignment protrusions 170 can have any shape. In the illustrated embodiment, the alignment protrusions 170 can have an elongated or oval shape. In some embodiments, the protrusions can have any of a variety of shapes, such as cylindrical or rectangular extensions.

The distal section 160 can include a head 172. The head 172 can be configured to be positioned distally within the upper section 102 and the lower section 104. The head 172 can be conical. The head 172 can flare outward toward the distal surfaces 112, 132. The head 172 can be larger near the distal surfaces 112, 132 than toward the middle. The head 172 can form a frustoconical shape. The head 172 can have an angled surface configured to slide against the angled surfaces of the grooves 150. The head 172 can be configured to slide and press against the grooves 150 of the upper structure 102 and lower structure 104. The head 172 can have sufficient smoothness to functionally slide and press against the grooves 150.

The distal section 160 can include a threaded portion 174. The threaded portion 174 can extend proximally from the head 172. The threaded portion 174 can be configured to couple with the distal opening 166 of the coupler 164. The threaded portion 174 can be integrally or monolithically formed with the head 172. The threaded portion 174 can be separately formed from the head 172 and coupled thereto.

The distal section 160 can also have a keyed shaft 176. The keyed shaft 176 can extend proximally from the threaded portion 174. The keyed shaft 176 can extend proximally along a longitudinal axis of the screw mechanism 106. The keyed shaft 176 is configured to slideably couple with the proximal section 162. As described below, the keyed shaft 176 can be keyed, such that when the proximal section 162 is rotated, the distal section 160 also rotates as a unit. The keyed shaft 176 can be integrally or monolithically formed with the head 172 and/or the threaded portion 174. The keyed shaft 176 can be separately formed from the head 172 and/or the threaded portion 174 and coupled thereto.

The proximal section 162 can include a head 178. The head 178 can be configured to be positioned proximally within the upper section 102 and the lower section 104. The head 178 can be conical. The head 178 can flare outward toward the proximal surfaces 114, 134. The head 178 can be larger near the proximal surfaces 114, 134 than toward the middle. The head 178 can form a frustoconical shape. The head 178 can have an angled surface configured to slide against the angled surfaces of the grooves 152. The head 178 can be configured to slide and press against the grooves 152 of the upper structure 102 and lower structure 104. The head 178 can have sufficient smoothness to functionally slide and press against the grooves 152.

The proximal section 162 can include a threaded portion 180. The threaded portion 180 can extend distally from the head 178. The threaded portion 180 can be configured to couple with the proximal opening 168 of the coupler 164. The threaded portion 180 can be integrally or monolithically formed with the head 178. The threaded portion 180 can be separately formed from the head 178 and coupled thereto.

The proximal section 162 can also have a keyed bore 182. The keyed shaft 176 of the distal section 160 can be configured to extend into the keyed bore 182 from the distal end of the proximal section 162. The keyed shaft 176 of the distal section 160 can be inward from the threaded portion 180 of the proximal section 162 when disposed therein. The keyed bore 182 can extend along a longitudinal axis of the screw mechanism 106. The keyed bore 182 is configured to slideably couple with the keyed shaft 176 of the distal portion 160. The keyed bore 182 and the keyed shaft 176 transmit torque. As the proximal section 162 is rotated, the distal section 160 also rotates due to the interaction between the keyed bore 182 and the keyed shaft 176. While the proximal portion 162 includes the keyed bore 182 and the distal portion 160 includes the keyed shaft 176, in other embodiments, the proximal portion 162 includes the keyed shaft and the distal portion 160 includes the keyed bore.

The head 178 can include a drive interface 184 configured to receive the deployment tool 200 for rotating or driving the proximal section 162. In the illustrated embodiment, the head 178 has a fluted socket with six flutes. In other embodiments, the head 178 can have any of a variety of drive interfaces, such as slotted, cross and polygonal heads. In some embodiments, the drive interface 184 and the keyed bore 182 are continuous. In some embodiments, the drive interface 184 and the keyed bore 182 have the same keyed shape.

The distal section 160 and the proximal section 162 can be threaded. The distal section 160 and the proximal section 162 can have threads in opposite directions. In some embodiments, the distal section 160 is left handed threads and the proximal section 162 is right handed threads. As disclosed herein, the threads in opposite directions enable the screw mechanism 106 to contract or extend when rotated. The distal section 160 can have threads that are configured to engage threads in the distal opening 166 of the coupler 164. The proximal section 162 can have threads that are configured to engage threads in the proximal opening 168 of the coupler 164. In the illustrated embodiment, the distal section 160 and the proximal section 162 have external threads while the coupler 164 has internal threads. In other embodiments, the coupler 164 can have external threads while the distal section 160 and the proximal section 162 can have internal threads.

The distal section 160 and the proximal section 162 can be rotatably linked with the keyed coupling, such that when the proximal section 162 is rotated, the distal section 160 also rotates as a unit. The keyed shaft 176 on the distal section 160 can have a keyed shape that slideably engages with the keyed bore 182 on the proximal section 162. In the illustrated embodiment the keyed shaft 176 has six flutes that slideably engage the keyed bore 182 having a fluted socket with six flutes. Other suitable shapes or geometric configurations for a keyed connection between the distal section 160 and the proximal section 162 may be used in the screw mechanism 106 to achieve the desired results, such as triangular, hexagonal, oval, star-shaped, or other non-circular shape.

The drive interface 184 can be engaged by the deployment tool 200 to rotate the proximal portion 162. The drive interface 184 can be rotated to compress the screw mechanism 106. Rotation of the drive interface 184 can cause the distal section 160 and the proximal section 162 of the screw mechanism 106 to move toward each other. During movement, the heads 172, 178 of the portions 160, 162 slide along the grooves 150, 152 in the upper structure 102 and lower structure 104 toward each other.

The movement of the distal portion 160 and the proximal portion 162 toward each other moves the two structures 102, 104 away from each other to expand the curved expandable interbody device 100. The movement of the distal portion 160 and the proximal portion 162 away from each other moves the two structures 102, 104 toward each other to collapse the curved expandable interbody device 100. The distal portion 160 and the proximal portion 162 move toward and way from each other along the longitudinal axis of the screw mechanism 106. The upper structure 102 and the lower structure 104 expand and collapse in a direction perpendicular to the longitudinal axis of the screw mechanism 106. The alignment protrusions 170 prevent the translation of the upper structure 102 and the lower structure 104 during expansion.

In some embodiments, turning the drive interface 184 clockwise causes the expansion of the curved expandable interbody device 100. In some methods, the drive interface 184 may be actuated in the opposite direction to change the curved expandable interbody device 100 from the expanded configuration back to the collapsed configuration. In some embodiments, turning the drive interface counter-clockwise causes the collapsing of the curved expandable interbody device 100. This ability to reversibly expand and collapse the curved expandable interbody device 100 can allow the curved expandable interbody device 100 to be moved to another location, repositioned, or removed from the patient.

The screw mechanism 106 can vary in length to change the curved expandable interbody device 100 from the collapsed configuration to the expanded configuration. Initially, the length of the screw mechanism 106 between the heads 172, 178 can be LC in the fully collapsed configuration as shown in FIG. 11. As the drive interface 184 of the proximal section 162 is rotated in a first direction, the proximal section 162 is screwed into the coupler 164 and the distal section 160 is screwed into the coupler 164. The distal section 160 rotates with the proximal section 162 due to the keyed interface. The distal section 160 and the proximal section 162 can have opposite handed threads so as the proximal section 162 is screwed into the coupler 164, the distal section 160 is also screwed into the coupler 164. The length of the screw mechanism 106 between the heads 172, 178 contracts to LE in the fully expanded configuration as shown in FIG. 12. By reversing rotation of the drive interface 184 in a second direction, opposite the first, the screw mechanism 106 can be extended in length from LE back to LC or any length therebetween. The curved expandable interbody device 100 can be expanded by any incremental height between the fully collapsed configuration and the fully expanded configuration. In some embodiments, the expansion of the curved expandable interbody device 100 is the expansion from the fully collapsed configuration to the fully expanded configuration. In some embodiments, the expansion of the curved expandable interbody device 100 is 2.5 mm. In some embodiments, the expansion of the curved expandable interbody device 100 is 3 mm. In some embodiments, the expansion of the curved expandable interbody device 100 is 3.5 mm. In some embodiments, the expansion of the curved expandable interbody device 100 is up to 4 mm. In some embodiments, the curved expandable interbody device 100 can be expanded by any height greater than 0 mm and up to 3 mm. In some embodiments, the curved expandable interbody device 100 can be expanded by any height greater than 0 mm and up to 4 mm. In some embodiments, the curved expandable interbody device 100 can be designed to be expanded by any height, including greater than 3 mm.

The alignment protrusions 170 on the coupler 164 are constrained in the alignment slots 122, 142 on the upper structure 102 and lower structure 104 to prevent the coupler 164 from rotating with the distal section 160 and the proximal section 162 as the drive interface 184 is rotated. The coupler 164 remains stationary as the distal section 160 and the proximal section 162 rotate relative to the coupler 164. The coupler 164 remains stationary as the upper structure 102 and the lower structure 104 expand relative to the coupler 164. The alignment protrusions 170 on the coupler 164 remain within the alignment slots 122, 142 on the upper structure 102 and lower structure 104 in the fully collapsed configuration and the fully expanded configuration.

The rotation of the proximal portion 162 can cause the rotation of the distal portion 160. The rotation of the proximal portion 162 can cause the distal portion 160 and the proximal portion 162 to move toward each other. The rotation of the proximal portion 162 can cause the distal portion 160 and the proximal portion 162 to move away from each other. The opposite threads of the distal portion 160 and the proximal portion 162 causes this relative movement. The keyed shaft 176 and keyed bore 182 transmit rotational forces from the drive interface 184 to the distal portion 160.

In some embodiments, in the collapsed configuration the curved expandable interbody device 100 has a height of HC. The head 172 of the distal section 160 can engage the grooves 150 of the upper structure 102 and lower structure 104. The head 178 of the proximal section 162 can contact the grooves 152 of the upper structure 102 and lower structure 104. When the drive interface 184 is rotated in a first direction, the distal section 160 and the proximal section 162 can move toward each other from LC to LE, or any length therebetween. When this happens, the heads 172, 178 can push against the grooves 150, 152 in the upper structure 102 and lower structure 104, causing the upper structure 102 and lower structure 104 to separate. The height between the upper structure 102 and the lower structure 104 can increase from HC (collapsed configuration) to HE (expanded configuration), or any height therebetween. The curved expandable interbody device 100 does not have to be completely expanded to HE and may only be expanded to a partial height between HC and HE, depending on the expansion needed between the adjacent vertebrae. In some embodiments, the grooves 150, 152 can have features that increase resistance to turning of the screw mechanism 106, so that increased actuating forces are required during select portions of the expansion procedure. This variation of actuating forces can provide tactile feedback to the user that the curved expandable interbody device 100 is nearing the limits of its expansion.

The threaded portion 174 of the distal section 160 can engage with the distal opening 166 of the coupler 164 and the threaded portion 180 of the proximal section 162 can engage with the proximal opening 168 of the coupler 164. The distal opening 166 and the proximal opening 168 can have thread patterns in opposite directions. The threaded portions 174, 180 can have thread patterns in opposite directions. In some embodiments, the openings 166, 168 and the threaded portions 174, 180 may have equal pitch, such that during expansion, the proximal portion and the distal portion of the upper structure 102 and the lower structure 104 translate or move at the same rate. In other embodiments, the openings 166, 168 and the threaded portions 174, 180 may have different pitches, such that during expansion, the proximal portion and the distal portion of the upper structure 102 and the lower structure 104 translate or move at different rates. For example, the proximal portion of the upper structure 102 and the lower structure 104 may translate or move at a first rate of speed and the distal portion of the upper structure 102 and the lower structure 104 may translate or move at a second rate of speed. The first rate of speed may be faster or slower than the second rate of speed.

This allows for some angularity between the upper structure 102 and lower structure 104 during expansion. The difference between the first and second rates of speed allows the user to select a curved expandable interbody device that has some angulation after expansion, for example to account for the lordotic curvature of the spine.

The screw mechanism 106 or portions of the screw mechanism 106 can be fabricated from any biocompatible material suitable for implantation in the human spine, such as metals including, but not limited to, stainless steel, titanium and titanium alloys, as well as surgical grade plastics, plastic composites, ceramics, bone, and other suitable materials. In some embodiments, the distal portion 160 and the proximal portion 162 may be formed of a porous material that participates in the growth of bone with the adjacent vertebral bodies. In some embodiments, the screw mechanism 106 can include a roughened surface that is coated with a porous material, such as a titanium coating, or the material may be chemically etched to form pores that participate in the growth of bone with the adjacent vertebra. In some embodiments, only portions of the screw mechanism 106 may be formed of a porous material, coated with a porous material, or chemically etched to form a porous surface, such as the heads 172, 178, which may be exposed to the native anatomy after implantation. In some embodiments, the surface porosity may be between 50 and 300 microns.

In some embodiments, the screw mechanism may be a compression screw having a proximal section threadably coupled to a distal section, the proximal section having a threaded shaft and the distal section having a threaded bore, or vice-versa, such that when the proximal section is rotated, the threaded shaft engages the threaded bore to shorten or lengthen the distance between the distal head 172 and the proximal head 178. The distal section can have anti-rotational features, such as for example an oblong head shape, to prevent it from rotating as the proximal section is engaged with distal section.

The coupler 164 can include features to facilitate coupling with the deployment tool 200 as described herein. The coupler 164 can include a central portion 186. The central portion 186 can be disposed between the distal portion 160 and the proximal portion 162 in use. The central portion 186 can include the distal opening 166 and the proximal opening 168. The central portion 186 can include the alignment protrusions 170 extending through the upper structure 102 and the lower structure 104. The central portion 186 can be viewed through the openings 120, 140. The central portion 186 can prevent material from encroaching the threads of the screw mechanism during use. The central portion 186 can protect the threads as the openings 120, 140 are packed with material.

The coupler 164 can include a proximal interface 188. The proximal interface 188 can include a left arm 190 and a right arm 192. In some embodiments, the left arm 190 and the right arm 192 extend laterally from the proximal opening 168. In some embodiments, the left arm 190 and the right arm 192 are aligned with the proximal alignment protrusions 170. The left arm 190 can have a shaped surface configured to complement a shaped surface of the left surface 116 of the upper structure 102 and the left surface 136 of the lower structure 104. The right arm 192 can have a shaped surface configured to complement a shaped surface of the right surface 118 of the upper structure 102 and the right surface 138 of the lower structure 104.

The coupler 164 can include an upper connector 194 and a lower connector 196. The upper connector 194 can span between the left arm 190 and the right arm 192. The lower connector 194 can span between the left arm 190 and the right arm 192. The upper connector 194 and the lower connector 196 can form the proximal end of the curved expandable interbody device 100. The upper connector 194 can be shaped to receive the proximal surface 114 of the upper structure 102. The lower connector 196 can be shaped to receive the proximal surface 134 of the lower structure 104. The upper connector 194 can form a portion of a ring. The lower connector 196 can form a portion of a ring.

In some embodiments, the upper connector 194 and the lower connector 196 can have the same or similar perimeter. In some embodiments, the upper connector 194 and the lower connector 196 can be parallel. In some embodiments, the upper connector 194 and the lower connector 196 can be mirror images. In some embodiments, the upper connector 194 and the lower connector 196 can be symmetrical. The upper connector 194 and the lower connector 196 can receive the deployment tool 200 therebetween.

Referring back to FIGS. 2-3, the curved expandable interbody device 100 can include one or more curved slots 198. The upper structure 102 and the upper connector 194 can form a curved slot 198 therebetween. The lower structure 104 and the lower connector 196 can form a curved slot 198 therebetween. The curved slots 198 accept a portion of the deployment tool 200 as described herein. The curved slots 198 can facilitate locking the deployment tool 200 to the curved expandable interbody device 100 while allowing the deployment tool 200 to pivot relative to the curved expandable interbody device 100, as described herein.

Figure 13:
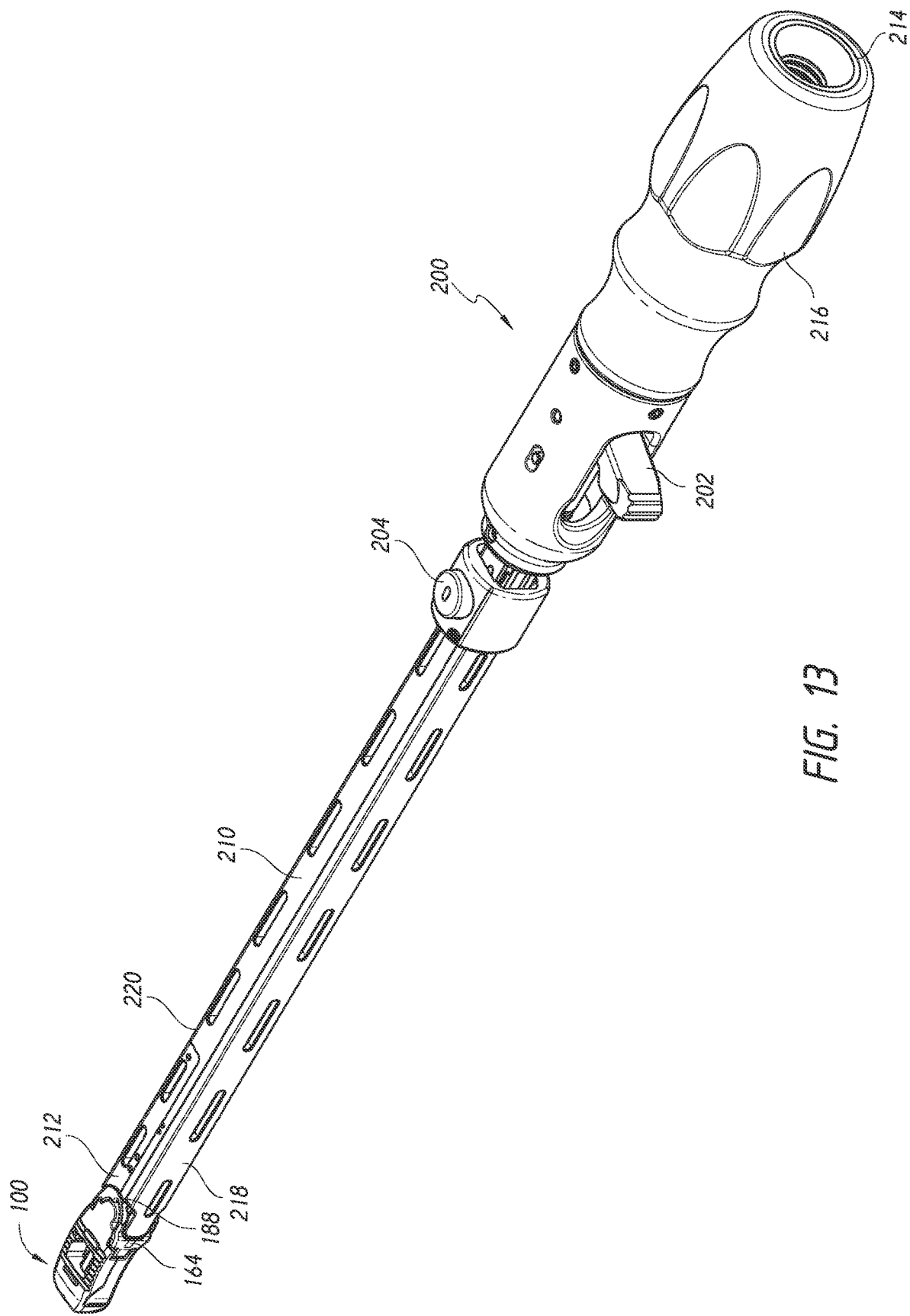
FIG. 13 is a perspective view of the curved expandable interbody device of FIG. 1 coupled to a deployment tool.
Figure 14:
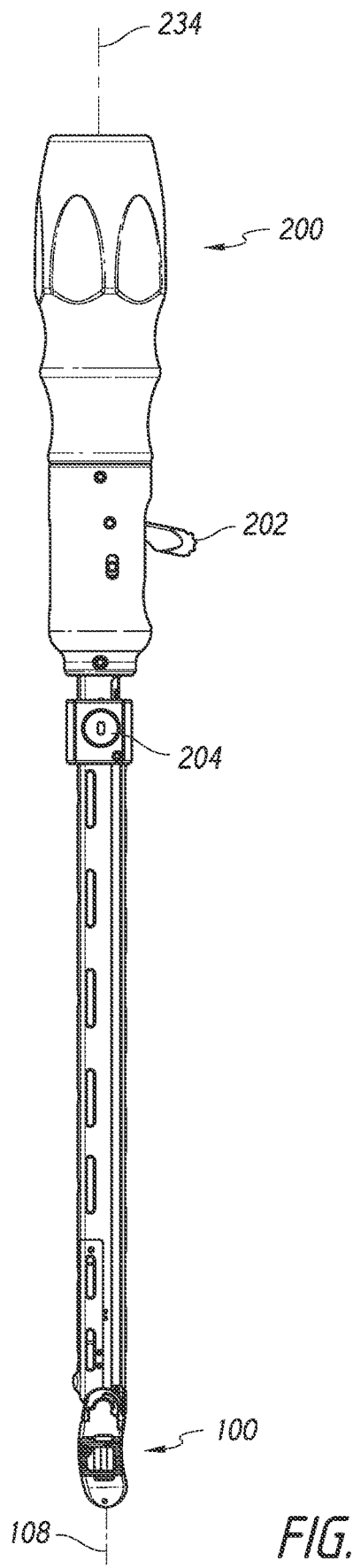
FIG. 14 is a top view of the curved expandable interbody device and the deployment tool of FIG. 13.
Figure 15:
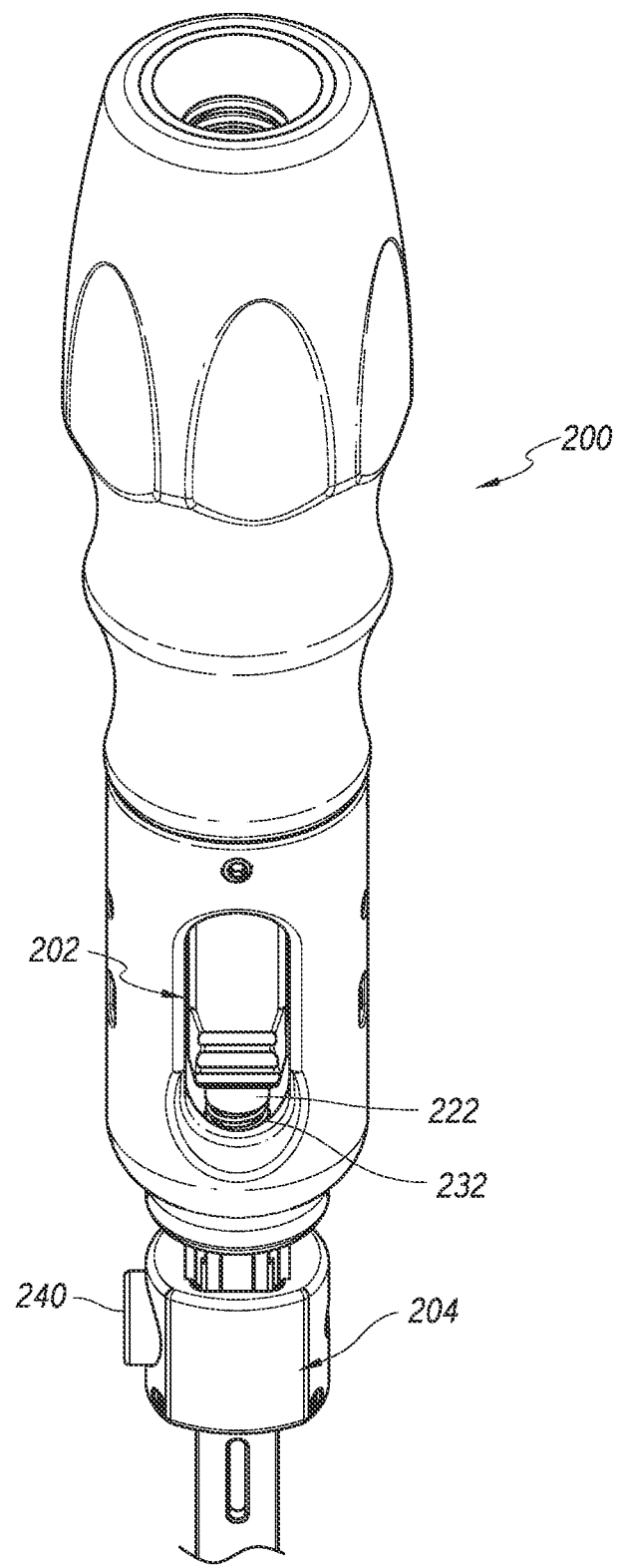
FIG. 15 is a close-up side view of the deployment tool of FIG. 13.

With reference to FIGS. 13-26, the deployment tool 200 can be used to implant the curved expandable interbody device 100 into the patient. FIG. 13 is a perspective view of the curved expandable interbody device 100 coupled to the deployment tool 200. FIG. 14 is a top view. FIG. 15 is a close-up side view. In use, an incision can be made on the patient to allow access to the implant site in the intervertebral space. The incision can be made for implanting the curved expandable interbody device 100 from any approach, including from the posterior, lateral or anterior directions. The incision can be small for a minimally invasive procedure or a larger incision can be used for an open surgery. Once the implant site is accessed, the two adjacent vertebrae can be distracted in some situations to open up the intervertebral space. In some situations, the curved expandable interbody device 100 can be used to at least partially distract the vertebrae during the implant procedure. In some situations, the intervertebral space may include a degenerated disc or other disorder that may require a partial or complete discectomy prior to insertion of the curved expandable interbody device 100.

In some configurations, more than one curved expandable interbody device 100 can be implanted between the adjacent vertebrae of the patient. In such embodiments, multiple curved expandable interbody device 100 can be placed in a side-by-side configuration or any other suitable configuration, thereby creating additional support. In some methods, only one curved expandable interbody device 100 is utilized in the intervertebral space. In some methods, two or more curved expandable interbody device 100 are utilized in the intervertebral space.

The deployment tool 200 can perform multiple functions. The deployment tool 200 can reversibly lock onto the curved expandable interbody device 100. The deployment tool 200 can include a locking mechanism 202. The deployment tool 200 can pivot relative to the curved expandable interbody device 100. The deployment tool 200 can include pivoting mechanism 204. The pivoting mechanism 204 can hold the deployment tool 200 in a straight position or the pivoting mechanism 204 can allow the deployment tool 200 to pivot. The deployment tool 200 can rotate the drive interface 184 of the screw mechanism 106. The deployment tool 200 can include a driving mechanism 206. The driving mechanism 206 can allow driving of the screw mechanism 106 in any straight or pivoted position of the deployment tool 200 relative to the curved expandable interbody device 100. The deployment tool 200 is configured to attach securely to the curved expandable interbody device 100 to provide control during insertion.

Figure 16:
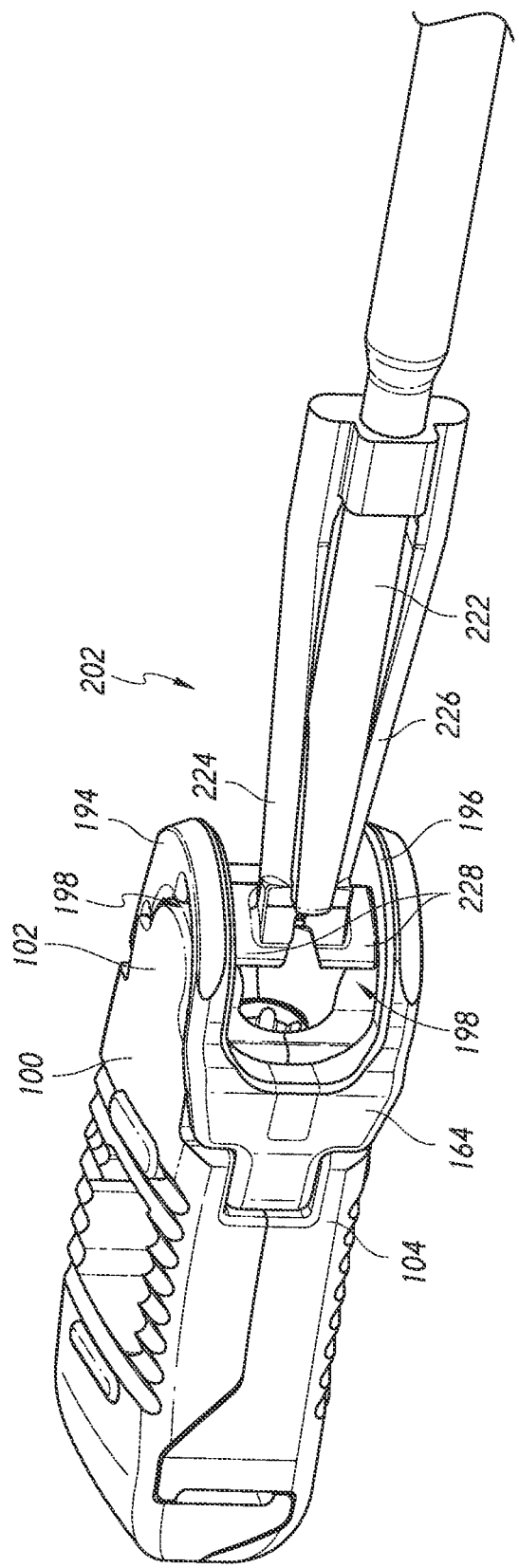
FIG. 16 is a close-up side view of a locking mechanism of the deployment tool of FIG. 13 in an unlocked configuration.
Figure 17:
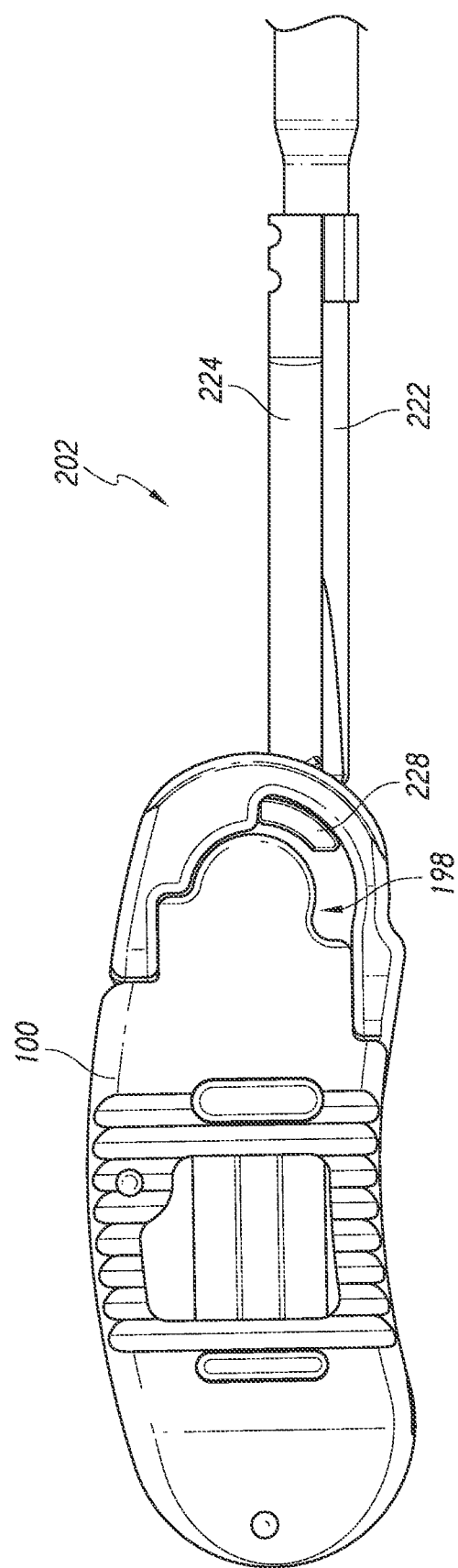
FIG. 17 is a close-up top view of the locking mechanism of the deployment tool of FIG. 13 in an unlocked configuration.
Figure 18:
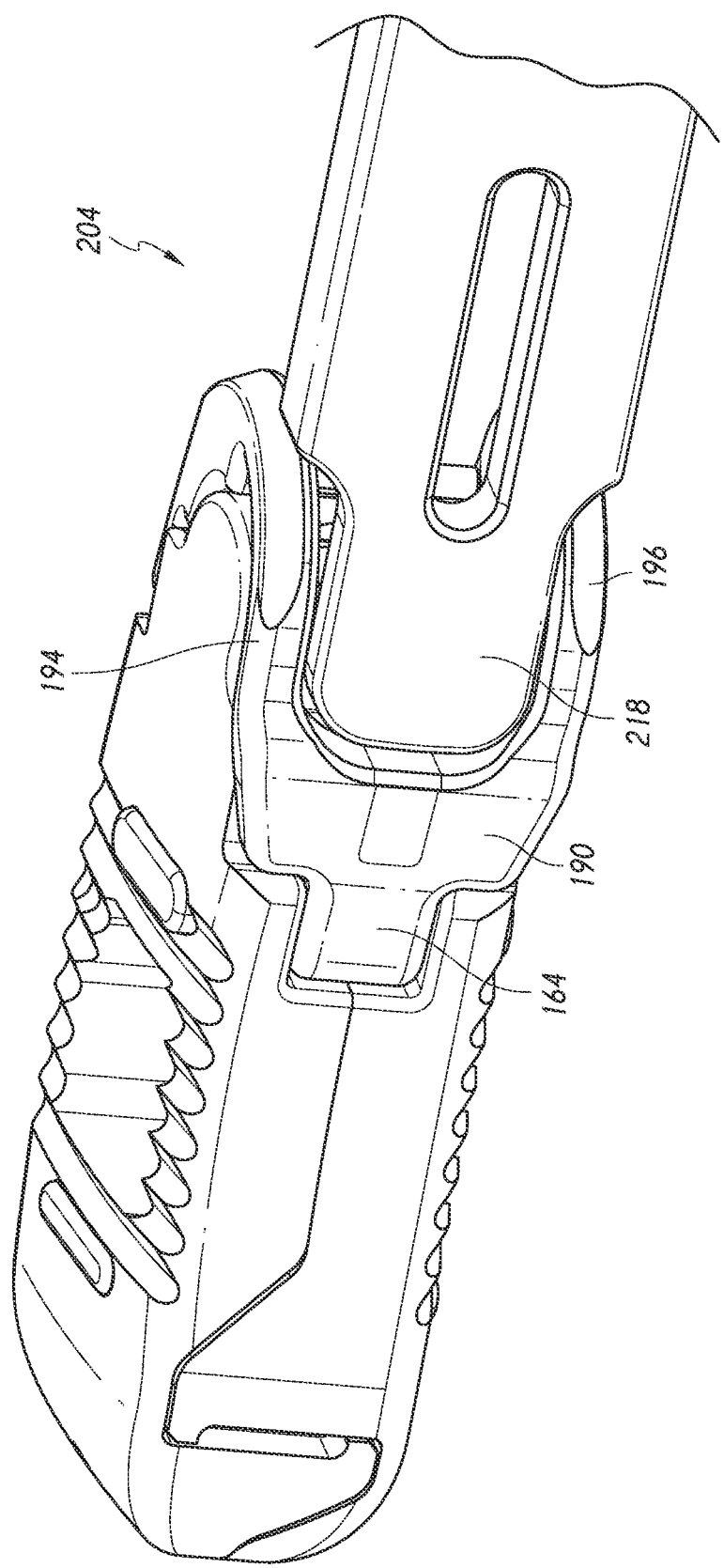
FIG. 18 is a close-up side view of a pivoting mechanism of the deployment tool of FIG. 13 in a distal position.
Figure 19:
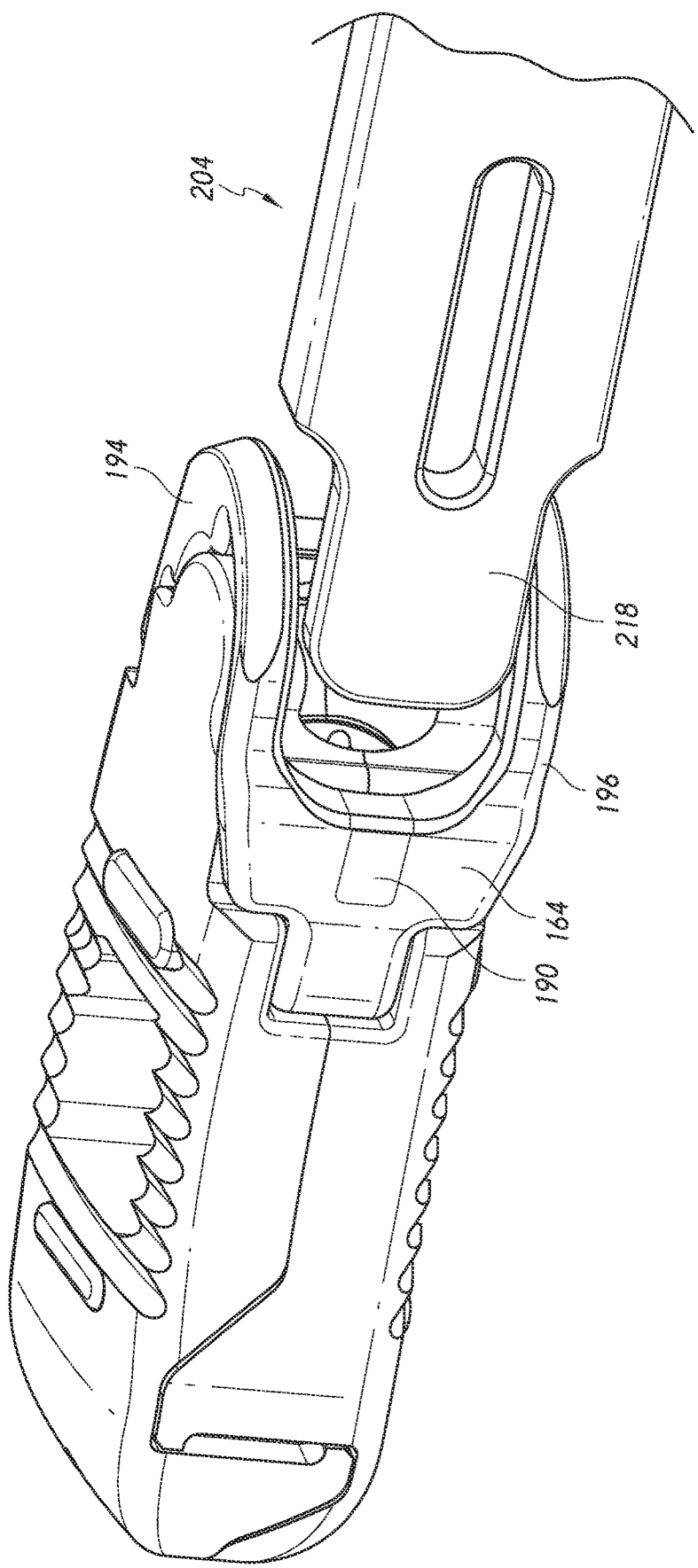
FIG. 19 is a close-up side view of the pivoting mechanism of the deployment tool of FIG. 13 in a proximal position.
Figure 20:
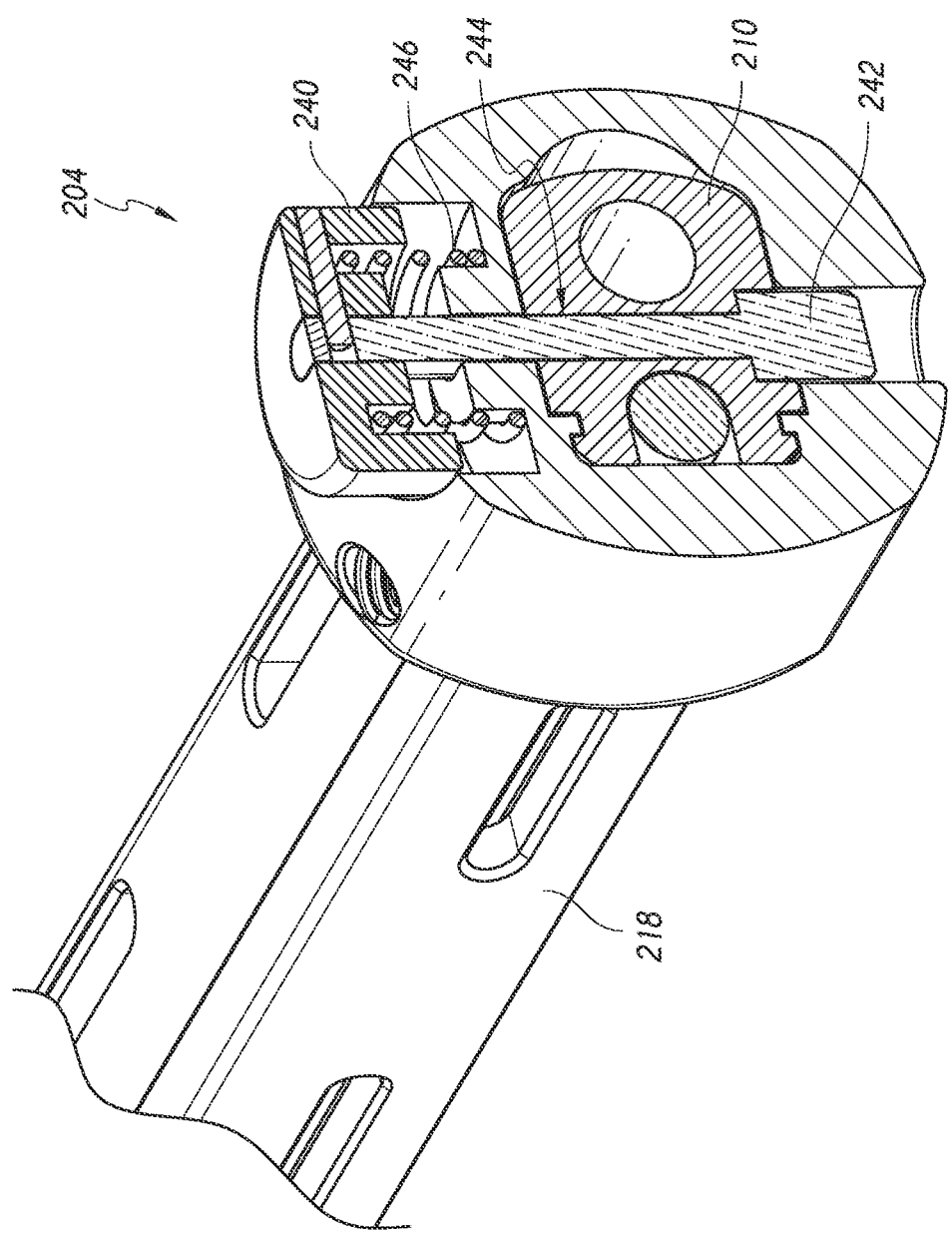
FIG. 20 is a close-up cross-sectional view of the pivoting mechanism of the deployment tool of FIG. 13.
Figure 21:
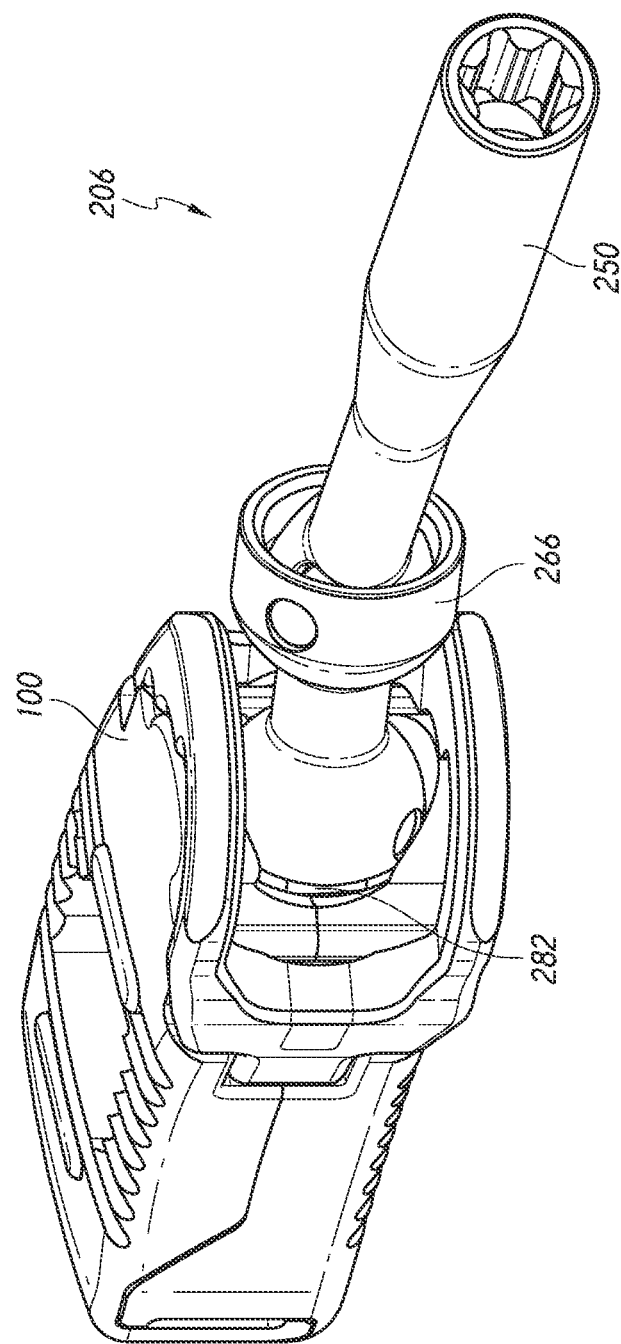
FIG. 21 is a close-up side view of a driving mechanism of the deployment tool of FIG. 13.
Figure 22:
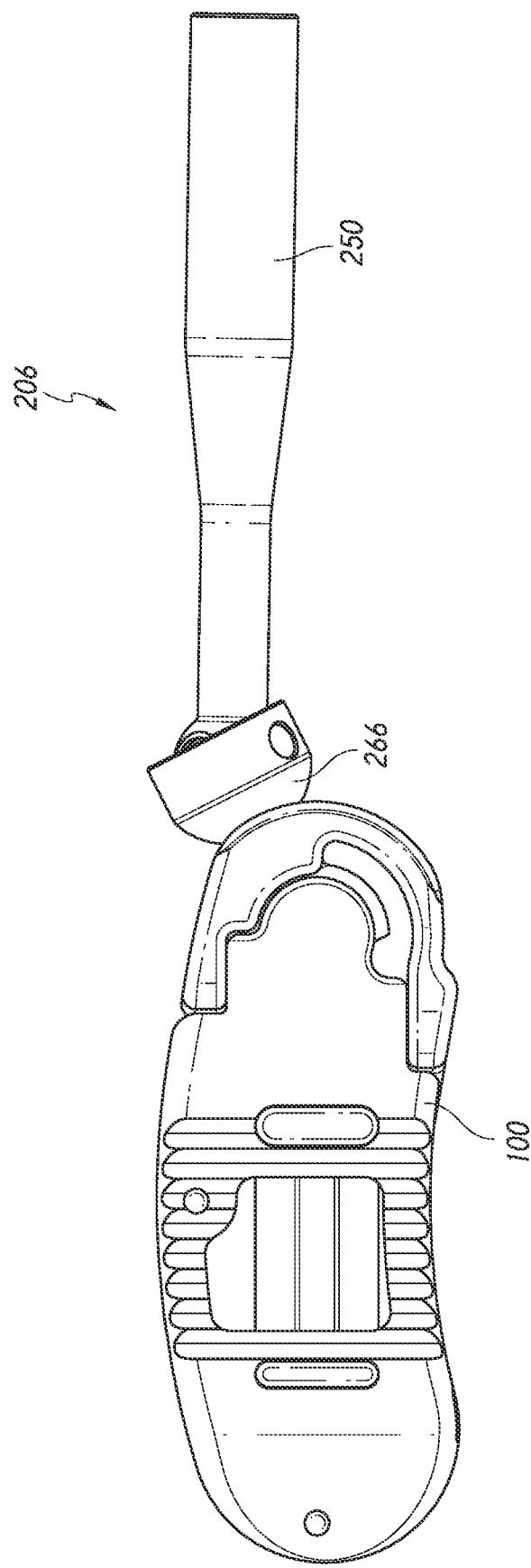
FIG. 22 is a close-up top view of the driving mechanism of the deployment tool of FIG. 13.
Figure 23:
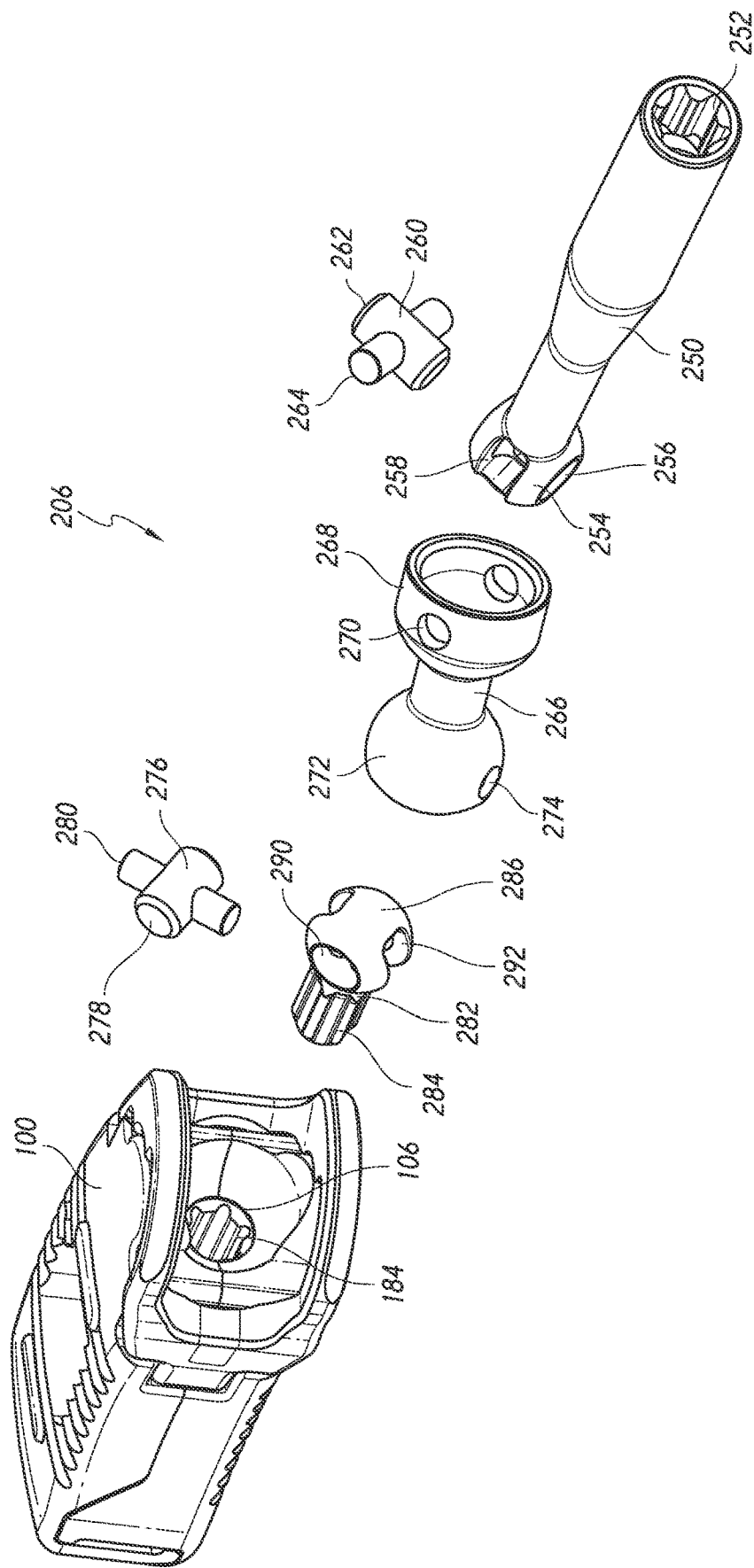
FIG. 23 is an exploded view of the driving mechanism of the deployment tool of FIG. 13.
Figure 24:
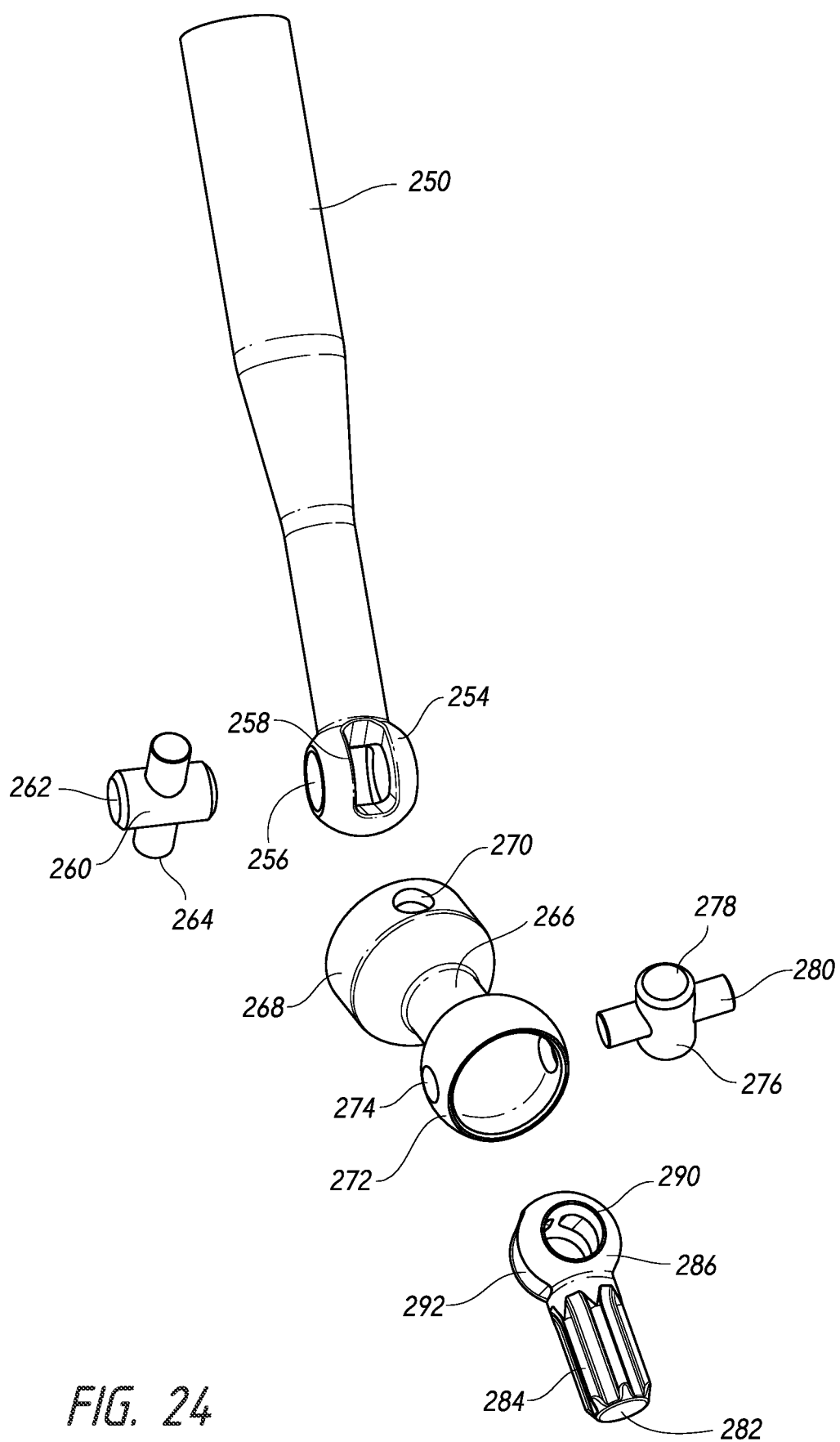
FIG. 24 is another exploded view of the driving mechanism of the deployment tool of FIG. 13.
Figure 25:
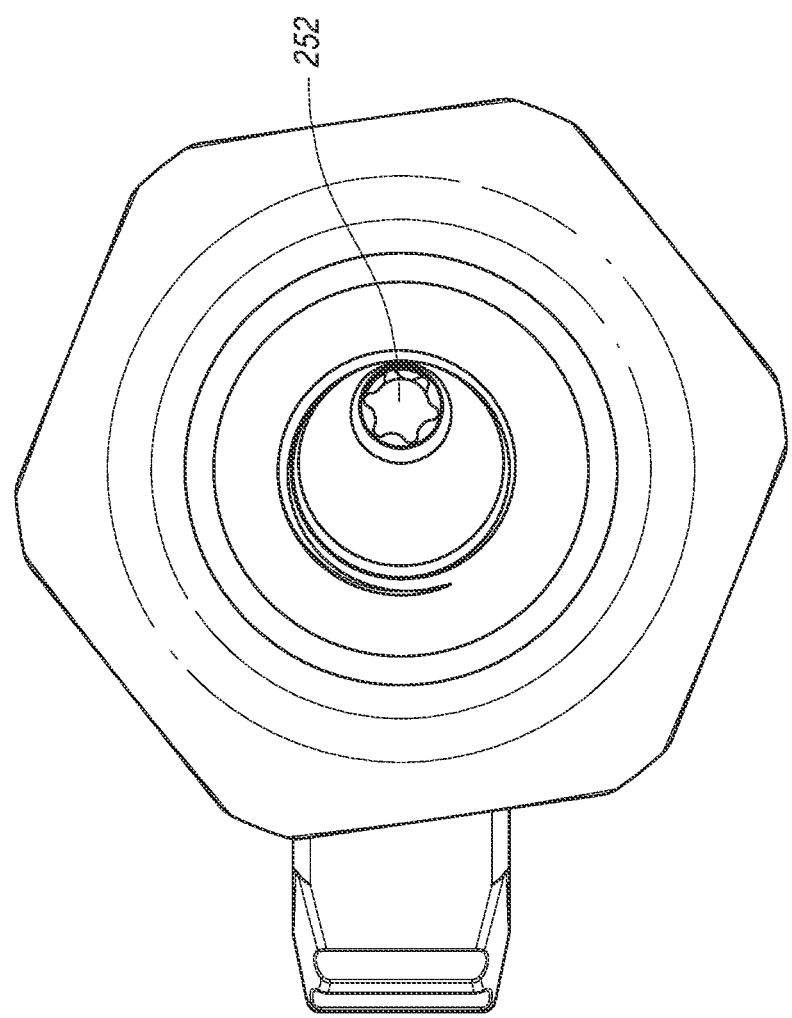
FIG. 25 is a rear view of the deployment tool of FIG. 13.
Figure 26:
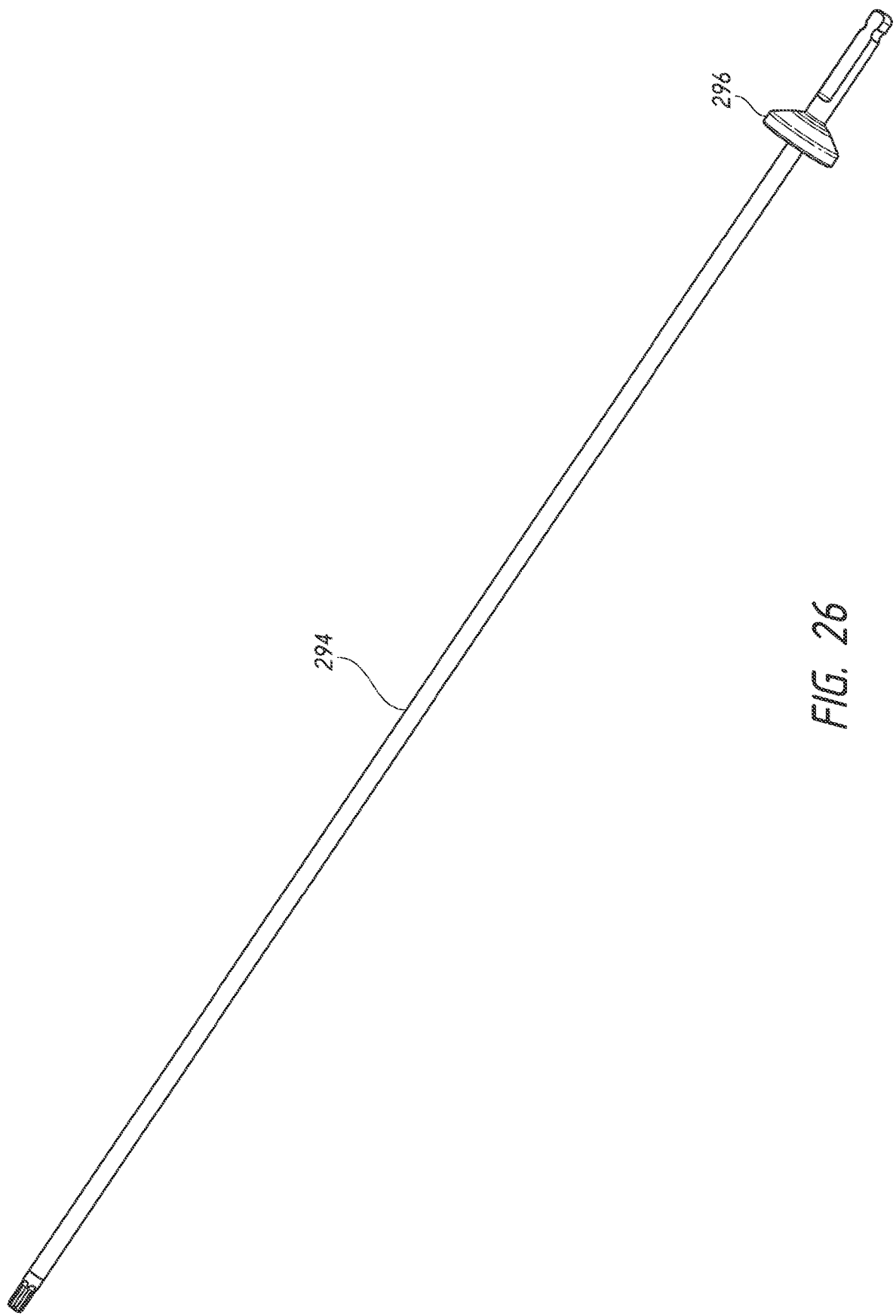
FIG. 26 is a perspective view of a keyed shaft.

FIG. 16 is a close-up side view of the locking mechanism 202. FIG. 17 is a close-up top view of the locking mechanism 202. FIGS. 18-19 are close-up side views of the pivoting mechanism 204. FIG. 20 is a close-up cross-sectional view of the pivoting mechanism 204. FIG. 21 is a close-up side view of the driving mechanism 206. FIG. 22 is a close-up top view of the driving mechanism 206. FIGS. 23-24 are exploded views of the driving mechanism 206. FIG. 25 is a rear view of the deployment tool 200. FIG. 26 is a perspective view of a keyed shaft of the driving mechanism 206.

Referring back to FIG. 13, the deployment tool 200 can include an elongated shaft 210. The deployment tool 200 can include a distal end 212 that is configured to interact with the curved expandable interbody device 100. The deployment tool 200 can include a proximal end 214. The proximal end 214 of the deployment tool 200 can include a handle 216. The handle 216 can be configured to be gripped by the user. The handle 216 can include features to facilitate the grip of the user. The handle 216 can be made of a material to facilitate gripping. In some embodiments, the handle 216 comprises a silicone rubber.

In methods of use, the deployment tool 200 is brought into proximity of the curved expandable interbody device 100. The distal end 212 can have a complementary shape to the curved expandable interbody device 100. The distal end 212 can mate with the proximal interface 188 of the coupler 164 shown in greater detail in FIG. 9. The distal end 212 facilitates alignment between the deployment tool 200 and the curved expandable interbody device 100 before the deployment tool is locked with the locking mechanism 202.

FIGS. 16 and 17 illustrate the locking mechanism 202 with portions of the deployment tool 200 removed. The locking mechanism 202 can be configured to interact with one or more curved slots 198 as described herein. The one or more curved slots 198 can be between the structures 102, 104 and the coupler 164. In some embodiments, the one or more curved slots 198 can be configured to allow pivoting in a certain direction. In some embodiments, the one or more curved slots 198 can extend toward the left of the curved expandable interbody device 100. In some embodiments, the one or more curved slots 198 can extend toward the concave surface of the curved expandable interbody device 100. In some embodiments, the one or more curved slots 198 can be configured to allow clockwise pivoting of the deployment tool 200 relative to the curved expandable interbody device 100 from the straight position. In some embodiments, the one or more curved slots 198 can extend toward the right of the curved expandable interbody device 100. In some embodiments, the one or more curved slots 198 can extend toward the convex surface of the curved expandable interbody device 100. In some embodiments, the one or more curved slots 198 can be configured to allow counter-clockwise pivoting of the deployment tool 200 relative to the curved expandable interbody device 100 from the straight position.

In some embodiments, the locking mechanism 202 can extend along the left side of the deployment tool 200. The locking mechanism 202 can include an inner shaft 222. The locking mechanism 202 can include an upper deflection arm 224 and a lower deflection arm 226. The upper deflection arm 224 and the lower deflection arm 226 can be coupled near a proximal end of the deflection arms 224, 226. The deflection arms 224, 226 can include one or more tines 228. The upper deflection arm 224 can include a tine 228 extending upward. The lower deflection arm 226 can include a tine 228 extending downward. The inner shaft 222 can extend between the upper deflection arm 224 and the lower deflection arm 226. The inner shaft 222 can move proximally and distally relative to the upper deflection arm 224 and the lower deflection arm 226.

The locking mechanism 202 can include a locking actuator 230 as shown in FIG. 15. The locking actuator 230 can control the proximal and distal movement of the inner shaft 222 relative to the upper deflection arm 224 and the lower deflection arm 226. The locking actuator 230 can be a switch. The locking actuator 230 can be near the proximal end of the deployment tool 200.

The locking actuator 230 can include a neutral positon as shown in FIG. 15. In some embodiments, the locking actuator 230 is perpendicular to the deployment tool 200 in the neutral positon. In some embodiments, the locking actuator 230 extends outward from the deployment tool 200 in the neutral positon. In some embodiments, the locking actuator 230 can be biased toward the neutral position. The locking mechanism 202 can include a spring 232. The spring 232 can bias the inner shaft 222 in the proximal direction. The spring 232 can bias the locking actuator 230 outward from the deployment tool 200.

In the neutral positon, the deployment tool 200 is not locked to the curved expandable interbody device 100. The deployment tool 200 can be in the neutral positon as the user positions the deployment tool 200 relative to the curved expandable interbody device 100. The deployment tool 200 is properly positioned relative to the curved expandable interbody device 100 when the distal end 212 of the deployment tool 200 abuts the upper connector 194 and the lower connector 196 of the coupler 164 of the curved expandable interbody device 100. The distal end 212 of the deployment tool 200 and the proximal end of the coupler 164 can have a corresponding shape to facilitate alignment between the deployment tool 200 and the curved expandable interbody device 100. The distal end 212 can have a shaped surface that complements the curved expandable interbody device 100 to facilitate the proper positioning of the components. The distal end 212 can include a left arm 218 and a right arm 220. The locking mechanism 202 can constrain at least one degree of freedom such that the deployment tool 200 is secured to the curved expandable interbody device 100.

Once the deployment tool 200 is properly positioned relative to the curved expandable interbody device 100, the locking mechanism 202 can be activated. The locking actuator 230 can include a retention position. In some embodiments, the locking actuator 230 is parallel to a longitudinal axis 234 of the deployment tool 200 in the retention positon. In some embodiments, the locking actuator 230 sits in-line with the longitudinal axis 234 of the deployment tool 200 in the retention positon. In some embodiments, the locking actuator 230 is pushed inward. The locking actuator 230 is coupled to the inner shaft 222 such that inward movement of the locking actuator 230 causes distal movement of inner shaft 222. The inner shaft 222 moves distally between the upper deflection arm 224 and the lower deflection arm 226, referring to FIG. 16. The inner shaft 222 can splay the upper deflection arm 224 and the lower deflection arm 226. The upper deflection arm 224 and the lower deflection arm 226 move radially outward from the inner shaft 222. The tines 228 of the upper deflection arm 224 and the lower deflection arm 226 move into the curved slots 198. The upper structure 102 and the upper connector 194 can form a curved slot 198 that receives the tine 228 of the upper deflection arm 224. The lower structure 104 and the lower connector 196 can form a curved slot 198 that receives the tine 228 of the lower deflection arm 226. The tines 228 are retained within the curved slots 198. The tines 228 constrain an additional degree of freedom. The tines 228 limit proximal movement of the deployment tool 200 relative to the curved expandable interbody device 100. The tines 228 function as a stop. The locking mechanism 202 can be considered a retention mechanism. The locking mechanism 202 retains the curved expandable interbody device 100 relative to the deployment tool 200. As described herein, the deployment tool 200 can pivot relative to the curved expandable interbody device 100 when the curved expandable interbody device 100 is retained.

FIGS. 18 and 19 illustrate the pivoting mechanism 204 with portions of the deployment tool 200 removed. The deployment tool 200 can allow pivoting of the deployment tool 200 relative to the curved expandable interbody device 100 in some configurations and prevent pivoting of the deployment tool 200 relative to the curved expandable interbody device 100 in other configurations. The deployment tool 200 can include the pivoting mechanism 204. Referring back to FIG. 14, the curved expandable interbody device 100 can include the longitudinal axis 108. The deployment tool 200 can include the longitudinal axis 234. The deployment tool 200 can have a straight position as shown in FIG. 14. The longitudinal axis 234 of the deployment tool 200 can be coaxial with the longitudinal axis 108 of the curved expandable interbody device 100 in the straight position. The longitudinal axis 234 of the deployment tool 200 can be aligned with the longitudinal axis 108 of the curved expandable interbody device 100 in the straight position. The longitudinal axis 234 of the deployment tool 200 can be parallel to the longitudinal axis 108 of the curved expandable interbody device 100 in the straight position.

The deployment tool 200 can have one or more pivoted position. The longitudinal axis 234 of the deployment tool 200 can be angled with respect to the longitudinal axis 108 of the curved expandable interbody device 100 in a pivoted position. The longitudinal axis 234 of the deployment tool 200 can be skewed relative to the longitudinal axis 108 of the curved expandable interbody device 100 in a pivoted position. The longitudinal axis 234 of the deployment tool 200 is not aligned with the longitudinal axis 108 of the curved expandable interbody device 100 in a pivoted position. The deployment tool 200 can have a plurality of pivoted positions. The deployment tool 200 can smoothly transition between pivoted positions as the tines 228 slide within the curved slots 198. The deployment tool 200 can include an infinite number of pivoted positions. The maximum angle of the longitudinal axis 234 of the deployment tool 200 with respect to the longitudinal axis 108 of the curved expandable interbody device 100 can be determined by the curved slots 198. In some embodiment, the deployment tool 200 can pivot relative to the curved expandable interbody device 100 by 0 degrees, 10 degrees, 20 degrees, 30 degrees, 40 degrees, 50 degrees, 60 degrees, 70 degrees, 80 degrees, 90 degrees, 100 degrees, 110 degrees, 120 degrees, 130 degrees, 140 degrees, 150 degrees, 160 degrees, 170 degrees, 180 degrees, between 70 degrees and 90 degrees, between 50 degrees and 70 degrees, or any range of two of the foregoing values. In the illustrated embodiment, the angle of the deployment tool 200 relative to the curved expandable interbody device 100 can be between 0 degrees and 50 degrees. In some embodiments, the nominal pivot range of the deployment tool 200 relative to the curved expandable interbody device 100 is approximately in the range of 0° to 60°. In some embodiments, the nominal pivot range of the deployment tool 200 and curved expandable interbody device 100 relative to each other is approximately in the range of 4° to 55°. In some embodiments, the deployment tool 200 and the curved expandable interbody device 100 can pivot relative to each other by 0 degrees, 5 degrees, 10 degrees, 15 degrees, 20 degrees, 25 degrees, 30 degrees, 35 degrees, 40 degrees, 45 degrees, 50 degrees, 55 degrees, 60 degrees, 65 degrees, 70 degrees, or any range of two of the foregoing values. The range can account for manufacturing tolerances on both the curved expandable interbody device 100 and the deployment tool 200. In some embodiments, by the nature of the double-joint driving mechanism 206 of the deployment tool 200 as described herein, the designed operating range is from 0 degrees to 60 degrees. In some embodiments, other ranges are contemplated.

In some embodiments, the pivoting mechanism 204 can extend along the left side of the deployment tool 200. The pivoting mechanism 204 can include the left arm 218. The left arm 218 can extend along a portion of the length of the deployment tool 200. The left arm 218 can align with the left arm 190 of the coupler 164. The left arm 218 can fit within a space between the upper connector 194 and the lower connector 196 of the coupler 164. The left arm 218 can generally compliment the shape of the upper connector 194 and the lower connector 196.

Referring to FIGS. 15 and 20, the pivoting mechanism 204 can include a pivoting actuator 240. The pivoting actuator 240 can control the proximal and distal movement of the left arm 218 relative to the curved expandable interbody device 100. The pivoting actuator 240 can control the proximal and distal movement of the left arm 218 relative to the upper connector 194 and the lower connector 196. The pivoting actuator 240 can be a button. The pivoting actuator 240 can be near the proximal end of the deployment tool 200.

The pivoting actuator 240 can include two discrete position. The pivoting actuator 240 can slide between these two discrete positions. The pivoting actuator 240 can be biased to be in one of two discrete positions. The pivoting actuator 240 can include a straight position. The pivoting actuator 240 can include a pivoting position. The pivoting actuator 240 can be depressed to slide between the two positions. The pivoting actuator 240 can include a shaft 242. The upper portion of the shaft 242 can include a smaller profile. The lower portion of the shaft 242 can include a larger profile. The elongated shaft 210 can have a shaped slot 244 to receive the shaft 242. The lower portion of the shaft 242 with the larger profile fits within a shaped slot 244 at the straight position and the pivoting position. The shaft 242 must be depressed to lower the larger profile from the shaped slot 244 to allow the smaller profile of the shaft to be within the shaped slot 244. Depressing the pivoting actuator 240 lowers the shaft 242 such that the shaft 242 can move between the straight position and the pivoting position. The pivoting actuator 240 can include a spring 246. The spring 246 can bias the button outward from the deployment tool 200. The spring 246 can bias the lower portion of the shaft 242 into the shaped slot 244. The spring 246 can bias the upper portion of the shaft 242 out of the shaped slot 244.

The pivoting actuator 240 can include the straight position as shown in FIG. 18. The left arm 218 can be interlocked with the coupler 164 of the curved expandable interbody device 100 when the pivoting actuator 240 is in the straight position. The left arm 218 can be between the upper connector 194 and the lower connector 196. The pivoting actuator 240 can prevent or limit pivoting when the pivoting actuator 240 is in the straight position. The pivoting actuator 240 can prevent or limit pivoting by positioning the left arm 218 relative to the curved expandable interbody device 100. The pivoting actuator 240 can provide tactile feedback to the user that the pivoting actuator 240 is in the straight positon. In some embodiments, the spring 246 can push the button outward when the pivoting actuator 240 is in the straight position. In some embodiments, the straight position can correspond to a distal position of the pivoting actuator 240 on the deployment tool 200 as shown in FIG. 15.

The pivoting actuator 240 can include the pivoting position as shown in FIG. 19. The left arm 218 can be at least partially withdrawn relative to the curved expandable interbody device 100 when the pivoting actuator 240 is in the pivoting position. The left arm 218 can be at least partially removed from between the upper connector 194 and the lower connector 196. The pivoting actuator 240 can allow pivoting when the pivoting actuator 240 is in the pivoting position. The pivoting actuator 240 can allowing pivoting by retracting the left arm 218 proximally relative to the curved expandable interbody device 100. The pivoting actuator 240 can provide tactile feedback to the user that the pivoting actuator 240 is in the pivoting positon. In some embodiments, the spring 246 can push the button outward when the pivoting actuator 240 is in the pivoting position. In some embodiments, the pivoting position of the pivoting actuator 240 can allow the deployment tool 200 to assume one or more pivoted position upon a torque being applied by the user to pivot the deployment tool 200. In some embodiments, the pivoting positon can correspond to a proximal position of the pivoting actuator 240 on the deployment tool 200.

The locking mechanism 202 and the pivoting mechanism 204 can be utilized in any order. In some embodiments, the locking mechanism 202 is actuated before the pivoting actuator 240 is actuated. The locking mechanism 202 is actuated to lock the deployment tool 200 first. In some embodiments, the locking mechanism 202 is actuated to lock the deployment tool 200 to the curved expandable interbody device 100 when the pivoting actuator 240 is in the pivoting position. In some embodiments, the locking mechanism 202 is actuated to lock the deployment tool 200 to the curved expandable interbody device 100 when the pivoting actuator 240 is in the pivoting position and then the pivoting actuator 240 is actuated to the straight position. In some embodiments, pivoting actuator 240 is actuated to the straight position after the locking mechanism 202 is locked. Other configurations are possible. In some embodiments, the locking mechanism 202 is actuated to lock the deployment tool 200 to the curved expandable interbody device 100 when the pivoting actuator 240 is in the straight position. In some embodiments, the locking mechanism 202 is actuated after the pivoting actuator 240 is actuated.

In some methods, the deployment tool 200 can be locked in the straight position relative to the curved expandable interbody device 100 by pressing the pivoting actuator 240 and moving the pivoting actuator 240 distally into the straight position. In some methods, the deployment tool 200 can allow pivoting motion relative to the curved expandable interbody device 100 by pressing the pivoting actuator 240 and moving the pivoting actuator 240 proximally into the pivoting position. The deployment tool 200 can retain the curved expandable interbody device 100 via the locking mechanism 202 regardless of whether the deployment tool 200 is in a straight position or a pivoted position.

FIGS. 21-24 illustrate the driving mechanism 206 with portions of the deployment tool 200 removed. In some embodiments, the driving mechanism 206 can extend along the left side of the deployment tool 200. The driving mechanism 206 can include a first shaft 250. The first shaft 250 can be generally straight within the deployment tool 200. The first shaft 250 can include a keyed bore 252. The keyed bore 252 can extend from the proximal end of the first shaft 250. The keyed bore 252 can extend a portion of the length of the first shaft 250. The keyed bore 252 can extend along a longitudinal axis of the first shaft 250.

The first shaft 250 can include a ball end 254. The ball end 254 can include a first bore 256. The ball end 254 can include a first slot 258. The first bore 256 and the first slot 258 can be perpendicular.

The driving mechanism 206 can include a first connector 260. The first connector can include a first bore pin 262 and a first slot pin 264. The first bore pin 262 can be configured to be received in the first bore 256. The first bore pin 262 can be configured to couple the first connector 260 and the first shaft 250. The first slot pin 264 can be configured to be received in the first slot 258. In some methods of use, the first slot pin 264 can slide within the first slot 258.

The driving mechanism 206 can include a second shaft 266. The second shaft 266 can be generally skewed within the deployment tool 200. The second shaft 266 can include a proximal socket end 268. The proximal socket end 268 can extend from the proximal end of the second shaft 266. The proximal socket end 268 can receive the ball end 254 of the first shaft 250. The proximal socket end 268 can allowing pivoting motion of the ball end 254 of the first shaft 250. The proximal socket end 268 can extend a portion of the length of the second shaft 266. The proximal socket end 268 can extend along a longitudinal axis of the second shaft 266. The proximal socket end 268 can include a second proximal bore 270. The first slot pin 264 can be configured to be received in the second proximal bore 270. The first slot pin 264 can couple the first shaft 250 and the second shaft 266. The first slot pin 264 can allow the first shaft 250 and the second shaft 266 to pivot relative to each other over a very limited range. In some embodiments, the first shaft 250 and the second shaft 266 do not pivot. In some embodiments, the first shaft 250 and the second shaft 266 are held at a fixed pivot angle. This fixed pivot angle can be any angle. In some embodiments, the fixed pivot angle is between 27 degrees and 30 degrees. In some embodiments, the first slot 258 is designed to accommodate the fixed pivot angle. The first shaft 250 and the second shaft 266 can be held by an internal pocket geometry in the deployment tool 200. The first shaft 250 and the second shaft 266 can be held by an internal pocket geometry in the right arm 220 near the distal end 212 of the deployment tool 200. This joint design can allow rotation and/or torque to be transmitted from the axis of the first shaft 250 to the axis of the second shaft 266. The first shaft 250 can function as the input drive shaft. The second shaft 266 can function as a double joint coupling, as described herein.

The second shaft 266 can include a distal socket end 272. The distal socket end 272 can extend from the distal end of the second shaft 266. The distal socket end 272 can extend a portion of the length of the second shaft 266. The distal socket end 272 can extend along a longitudinal axis of the second shaft 266. The distal socket end 272 can include a second distal bore 274. The second proximal bore 270 and the second distal bore 274 can be perpendicular.

The driving mechanism 206 can include a second connector 276. The second connector 276 can include a second bore pin 278 and second slot pin 280. The second slot pin 280 can be configured to be received in the second distal bore 274.

The driving mechanism 206 can include a third shaft 282. The third shaft 282 can be generally straight within the deployment tool 200. The third shaft 282 can include a keyed shaft 284. The keyed shaft 284 can extend from the distal end of the third shaft 282. The keyed shaft 284 can extend a portion of the length of the third shaft 282. The keyed shaft 284 can extend along a longitudinal axis of the third shaft 282. The keyed shaft 284 can be configured to engage the drive interface 184. The screw mechanism 106 can include the drive interface 184 configured to receive the keyed shaft 284 of the driving mechanism 206 for rotating the screw mechanism 106.

The third shaft 282 can include a ball end 286. The ball end 286 can include a third bore 290. The ball end 286 can include a third slot 292. The third bore 290 and the third slot 292 can be perpendicular. The distal socket end 272 can receive the ball end 286 of the third shaft 282. The distal socket end 272 can allowing pivoting motion of the ball end 286 of the third shaft 282.

The second bore pin 278 can be configured to be received in the third bore 290. The second bore pin 278 can be configured to couple the second connector 276 and the third shaft 282. The second slot pin 280 can be configured to be received in the third slot 292. In some methods of use, the second slot pin 280 can slide within the third slot 292.

The second slot pin 280 can be configured to be received in the second distal bore 274. The second slot pin 280 can couple the second shaft 266 and the third shaft 282. The second slot pin 280 can allow the second shaft 266 and the third shaft 282 to pivot. In some embodiments, the first shaft 250 and the second shaft 266 do not pivot. In some embodiments, only the second shaft 266 and the third shaft 282 pivot. In some embodiments, the second shaft 266 and the third shaft 282 allow for pivoting for the total range of the deployment tool 200 relative to the curved expandable interbody device 100.

The first shaft 250, the first connector 260, the second shaft 266, the second connector 276, and the third shaft 282 couple together to form an assembly. In methods of use, the rotation of the first shaft 250 cause rotation of the second shaft 266 and the third shaft 282. The torque is transmitted by the first slot pin 264 which couples the first shaft 250 and the second shaft 266. The torque is transmitted by the second slot pin 280 which couples the second shaft 266 and the third shaft 282. The third shaft 282 can be coupled to the screw mechanism 106. The rotation of the first shaft 250 cause rotation of the screw mechanism 106 to expand the curved expandable interbody device 100.

The first shaft 250, the first connector 260, the second shaft 266, the second connector 276, and the third shaft 282 allow the deployment tool 200 to be in any pivoted position while allowing the driving mechanism 206 to rotate the screw mechanism 106. As the deployment tool 200 pivots, the first slot pin 264 can slide within the first slot 258 of the first shaft 250. As the deployment tool 200 pivots, the second slot pin 280 can slide within the third slot 292 of the third shaft 282. The slots 258, 292 accommodate the range of pivoted positions of the deployment tool 200. The slots 258, 292 accommodate pivoting up to 30 degrees, 40 degrees, 50 degrees, 60 degrees, 70 degrees, 80 degrees, 90 degrees, or any range of two of the foregoing values. In some methods of use, the first shaft 250 and the third shaft 282 can remain stationary as the deployment tool 200 pivots. In some methods of use, the third shaft 282 remains coaxial with the longitudinal axis 108 of the curved expandable interbody device 100 regardless of the position of the deployment tool 200. The first shaft 250 and the second shaft 266 can pivot relative to the third shaft 282 as the deployment tool 200 pivots.

As described herein, the deployment tool 200 can have a straight position. In the straight position of the deployment tool 200, the first shaft 250 and the second shaft 266 can be at the fixed pivot angle relative to each other. In the straight position, the first slot pin 264 transmits torque between the first shaft 250 and the second shaft 266. In the straight position, the first slot pin 264 slides within the first slot 258 as the first shaft 250 rotates. The first slot 258 enables a sweep of the first slot pin 264 that is necessitated by the fixed pivot angle between the first shaft 250 and the second shaft 266. The first slot pin 264 slides along the length of the first slot 258 during a full rotation of the first shaft 250. In some embodiments, the fixed pivot angle between the first shaft 250 and the second shaft 266 is between 27 degrees and 30 degrees. The first slot pin 264 can transmit torque when the first shaft 250 and the second shaft 266 are at this fixed pivot angle. The first slot pin 264 can slide twice the fixed pivot angle. In some embodiments, the first slot pin 264 needs to slide about twice the relative angle between the first shaft 250 and second shaft 266. Since the first shaft 250 and second shaft 266 are at the fixed pivot angle of 27 degrees to 30 degrees, the first slot pin 264 will slide or sweep from about negative 27 degrees to 30 degrees to positive 27 degrees to 30 degrees during a single rotation of the joint between the first shaft 250 and the second shaft 266. The sliding of the first slot pin 264 can allow the deployment tool 200 to transmit torque in the straight position.

In the straight position of the deployment tool 200, the second shaft 266 and the third shaft 282 can be skewed. In the straight position, the second slot pin 280 transmits torque between the second shaft 266 and the third shaft 282. In the straight position, the second slot pin 280 slides within the third slot 292 as the second shaft 266 rotates. In some embodiments, the second slot pin 280 can slide twice the fixed pivot angle in the straight position. In some embodiments, the second shaft 266 and the third shaft 282 are at an angle of 27 degrees to 30 degrees when the deployment tool 200 is in the straight position. In some embodiments, the second slot pin 280 needs to slide about twice the relative angle between the second shaft 266 and the third shaft 282. The second slot pin 280 will slide or sweep from about negative 27 degrees to 30 degrees to positive 27 degrees to 30 degrees during a single rotation of the joint between the second shaft 266 and the third shaft 282. The sliding of the second slot pin 280 can allow the deployment tool 200 to transmit torque in the straight position.

As described herein, the deployment tool 200 can have one or more pivoted positions. In the pivoted positions of the deployment tool 200, the first shaft 250 and the second shaft 266 remain at the fixed pivot angle relative to each other. In the pivoted positions, the first slot pin 264 transmits torque between the first shaft 250 and the second shaft 266. The first slot pin 264 slides within the first slot 258 as the first shaft 250 rotates. The motion of the first slot pin 264 accommodates the fixed pivot angle between the first shaft 250 and the second shaft 266. The first slot pin 264 slides along the length of the first slot 258 during a full rotation of the first shaft 250. The first slot pin 264 can slide up to twice the fixed pivot angle between the first shaft 250 and the second shaft 266. In some embodiments, the first slot pin 264 continues to slide twice the relative angle between the first shaft 250 and second shaft 266 in the pivoted positions of the deployment tool 200. Since the first shaft 250 and second shaft 266 are at the fixed pivot angle of 27 degrees to 30 degrees, the first slot pin 264 can slide or sweep from about negative 27 degrees to 30 degrees to positive 27 degrees to 30 degrees during a single rotation of the joint between the first shaft 250 and the second shaft 266 regardless of the angle of the deployment tool 200.

In a pivoted position of the deployment tool 200, the second shaft 266 and the third shaft 282 can be pivoted relative to each other. The second shaft 266 and the third shaft 282 can pivot relative to each other approximately negative 30 degrees to positive 30 degrees. This pivoting of the second shaft 266 and the third shaft 282 combined with the fixed pivot angle of 27 to 30 degrees between the first shaft 250 and the second shaft 266 allows the deployment tool 200 to achieve cumulative total deployment tool pivot angles of 0 degrees to 60 degrees. In the pivoted positions, the second slot pin 280 transmits torque between the second shaft 266 and the third shaft 282. In at least some pivoted positions, the second slot pin 280 slides within the third slot 292 as the second shaft 266 rotates. The third slot 292 accommodates the motion of the second slot pin 280 at the various pivoted positions between the second shaft 266 and the third shaft 282. The second slot pin 280 can slide along the length of the third slot 292 or a portion thereof during a full rotation of the second shaft 266. The second slot pin 280 transmits torque when the second shaft 266 and the third shaft 282 are angulated. In some embodiments, the second slot pin 280 needs to slide about twice the relative angle between the second shaft 266 and the third shaft 282. Since the second shaft 266 and the third shaft 282 can have a variable angle, the second slot pin 280 can slide or sweep from any range between negative 30 degrees and positive 30 degrees during a single rotation of the joint between the second shaft 266 and the third shaft 282. Unlike the first shaft 250 and the second shaft 266 that have a fixed angle, the second shaft 266 and the third shaft 282 are free to pivot relative to each other.

In one pivoted position, wherein the deployment tool 200 is approximately 30 degrees relative to the curved expandable interbody device 100, the second shaft 266 and the third shaft 282 can be coaxial. In this position, the second slot pin 280 transmits torque between the second shaft 266 and the third shaft 282. In this position, the longitudinal axis of the second shaft 266 can be aligned with the longitudinal axis of the third shaft 282. In some embodiments, the second slot pin 280 does not slide within the third slot 292 in this position. In some embodiments, the second slot pin 280 rotates in a plane in this position. If the second shaft 266 and third shaft 282 have a relative angle of 0 degrees, the second slot pin 280 does not slide within the third slot 292. This coupling between the second shaft 266 and the third shaft 282 will act as a straight joint in this position, and torque does not need to be transmitted at an angle.

If the second shaft 266 and the third shaft 282 have a relative angle of negative 30 degrees or positive 30 degrees, then similar with the first slot pin 264, the second slot pin 280 needs to sweep from negative 30 degrees to positive 30 degrees. If the second shaft 266 and the third shaft 282 have a relative angle of negative 15 degrees, then the second slot pin 280 needs to sweep from negative 15 degrees to positive 15 degrees. If the second shaft 266 and the third shaft 282 have a relative angle of positive 15 degrees, then the second slot pin 280 also needs to sweep from negative 15 degrees to positive 15 degrees. If the second shaft 266 and the third shaft 282 have a relative angle of 0 degrees, then the second slot pin 280 needs to sweep 0 degrees.

The combined sliding of the first slot pin 264 and the second slot pin 280 can allow the deployment tool 200 to transmit torque in the straight position and one or more pivoted positions. The second shaft 266 and the third shaft 282 can pivot relative to each other approximately negative 30 degrees to positive 30 degrees. This pivoting of the second shaft 266 and the third shaft 282, combined with the fixed angle of 27 degrees to 30 degrees between the first shaft 250 and second shaft 266 can achieve a cumulative total pivot angle of the deployment tool 200 of between 0 degrees to 60 degrees.

FIG. 25 is a rear view of the deployment tool 200. The deployment tool 200 can include a passageway toward the keyed bore 252 of the first shaft 250. The keyed bore 252 is configured to receive a keyed shaft 294 inserted into the deployment tool 200. FIG. 26 is a perspective view of the keyed shaft 294. In some embodiments, the keyed shaft 294 is removable. The keyed shaft 294 can be inserted into the deployment tool 200 to expand the curved expandable interbody device 100. The keyed shaft 294 can be a separate component from the deployment tool 200. In other embodiments, the keyed shaft 294 is located within the deployment tool 200.

The keyed shaft 294 is configured to couple with the keyed bore 252 to transmit torque. As the keyed shaft 294 is rotated, the first shaft 250 also rotates. While the first shaft 250 includes the keyed bore 252, in other embodiments, the first shaft 250 includes the keyed shaft and a keyed socket is inserted into the deployment tool 200. The keyed shaft 294 can be keyed along the entire length or a distal portion thereof. In the illustrated embodiment, the keyed shaft 294 has six flutes that slideably engages the keyed bore 252 having a fluted socket with six flutes. Other suitable shapes or geometric configurations for a keyed connection between the keyed bore 252 and the keyed shaft 294 may be used to achieve the desired results, such as triangular, hexagonal, oval, star-shaped, or other non-circular shape. The keyed shaft 294 can include a flange 296. The flange 296 can act as a depth stop of the keyed shaft 294. The keyed shaft 294 can include unitary structure. The keyed shaft 294 can have a two-piece or multiple piece construction. The keyed shaft 294 can be manufactured from a single piece of metal stock or from multiple pieces coupled together through any manufacturing technique.

In operation, the keyed shaft 294 can be placed through a passageway extending through the right side of the deployment tool 200 as shown in FIG. 25. After the curved expandable interbody device 100 is inserted and positioned within the intervertebral space between two vertebrae, the keyed shaft 294 can be used to deploy and expand the curved expandable interbody device 100 by applying a rotational force to the first shaft 250. By rotating the keyed shaft 294 at the proximal portion of the deployment tool 200, the first shaft 250 is also rotated, which in turn rotates the second shaft 266 and the third shaft 282, and thus the drive interface 184 of the screw mechanism 106 to expand the curved expandable interbody device 100.

As the driving mechanism 206 applies the rotational force, the curved expandable interbody device 100 gradually expands as described above. The curved expandable interbody device 100 can be expanded until it contacts the two adjacent vertebrae. In some embodiments, the curved expandable interbody device 100 can be used to distract the two adjacent vertebrae and open up the intervertebral space. The keyed shaft 294 can advantageously transmit sufficient torque to the screw mechanism 106 to enable distraction using the curved expandable interbody device 100. In some embodiments, the keyed shaft 294 can have a torque-limiting feature to prevent over-tightening of the screw mechanism 106. For example, the torque-limiting feature can include a spring-loaded clutch mechanism along the keyed shaft 294 that can only transmit a predetermined amount of torque before the clutch slips. The amount of torque that can be transmitted can depend on the stiffness of the clutch spring. In other embodiments, the torque-limiting feature can be a portion of the keyed shaft 294 that is configured to break at a predetermined torque. In other embodiments, the feature can be any functional torque-limiting device.

The deployment tool 200 can include any features to increase rigidity and functionality. The deployment tool 200 can include one or more sleeves disposed over the components of the deployment tool 200. The deployment tool 200 can include a passageway to receive the keyed shaft 294. The deployment tool 200 can include rails to facilitate the sliding of the left arm 218. The deployment tool 200 can include an impaction surface. In some embodiments, the deployment tool 200 can include an impaction cap. In some embodiments, the impaction cap can be a separate piece that is threadably engageable with the deployment tool 200. In some embodiments, a separate impaction cap can reduce or eliminate direct impaction force on the handle 216. The deployment tool can be configured to be struck by a mallet to facilitate placement of the curved expandable interbody device 100 between vertebrae. The deployment tool 200 can be configured to be struck by a mallet to insert the curved expandable interbody device 100 between vertebrae in the straight position. The deployment tool can be configured to be struck by a mallet to insert the curved expandable interbody device 100 between vertebrae in one or more pivoted positions. In some methods, striking the deployment tool 200 can change the trajectory of the deployment tool 200 when the deployment tool 200 is able to pivot. In some methods, striking the deployment tool 200 can cause the deployment tool to pivot to a greater angle when the deployment tool 200 is able to pivot.

The deployment tool 200 can include the locking mechanism 202, the pivoting mechanism 204, and the driving mechanism 206. The locking mechanism 202, the pivoting mechanism 204, and the driving mechanism 206 can extend through the length of the deployment tool 200. The locking mechanism 202, the pivoting mechanism 204, and the driving mechanism 206 can be independently actuated.

The locking mechanism 202, the pivoting mechanism 204, and the driving mechanism 206 can be actuated in a preferred order. In some methods, the locking mechanism 202 is actuated first to lock the deployment tool 200 to the curved expandable interbody device 100. In some methods, the pivoting mechanism 204 is actuated next to limit pivoting movement during positioning of the curved expandable interbody device 100. The pivoting mechanism 204 is actuated to the straight position. During positioning of the curved expandable interbody device 100, the pivoting mechanism 204 can be actuated to allow pivoting. The pivoting mechanism 204 is actuated to allow pivoting to facilitate further positioning of the curved expandable interbody device 100 within the disc space. In some methods, the driving mechanism 206 is actuated last to expand the curved expandable interbody device 100.

The locking mechanism 202, the pivoting mechanism 204, and the driving mechanism 206 can be located at any position along the length of the deployment tool. In some embodiments, the locking mechanism 202 and the pivoting mechanism 204 are generally on the left side of the deployment tool 200 and the driving mechanism 206 is generally in the center and right side of the deployment tool 200. The actuators 230, 240 can be located on the lateral and proximal portion on the deployment tool 200. In some embodiments, the keyed shaft 294 is inserted through the proximal end of the deployment tool 200 to actuate the driving mechanism 206. Other configurations and placements of the locking mechanism 202, the pivoting mechanism 204, and the driving mechanism 206 are contemplated.

In some embodiments, the deployment tool 200 can be coupled to the curved expandable interbody device 100 through other mechanisms. In some embodiments, the deployment tool 200 can have any mechanism configured to lock the deployment tool 200 to the curved expandable interbody device 100. In some embodiments, the deployment tool 200 can have any mechanism configured to prevent or allow pivoting of the deployment tool 200 relative to the curved expandable interbody device 100. In some embodiments, the deployment tool 200 can have any mechanism configured to rotate the screw mechanism 106.

Figure 27:
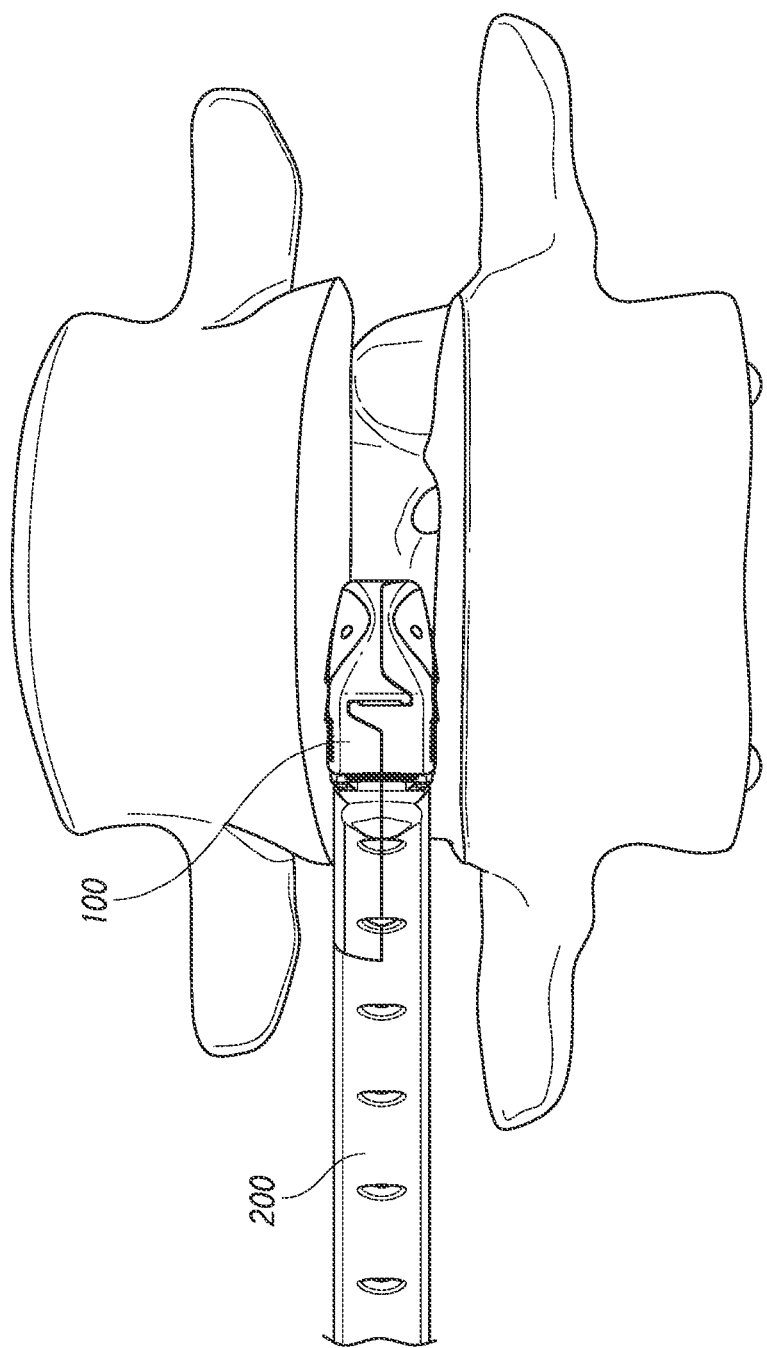
FIG. 27 is a view of the curved expandable interbody device of FIG. 1 coupled to a deployment tool in a straight position.
Figure 28:
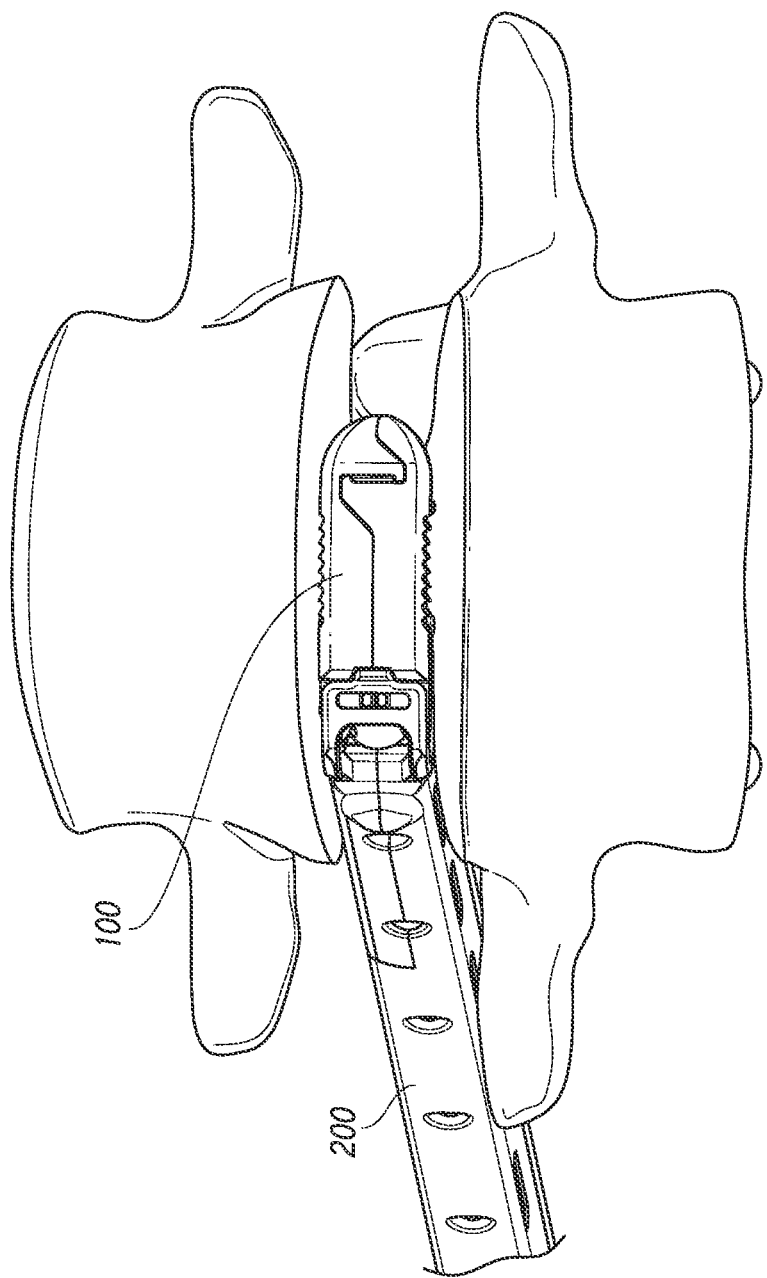
FIGS. 28 and 29 are views of the curved expandable interbody device of FIG. 1 coupled to a deployment tool in a pivoted position.
Figure 29:
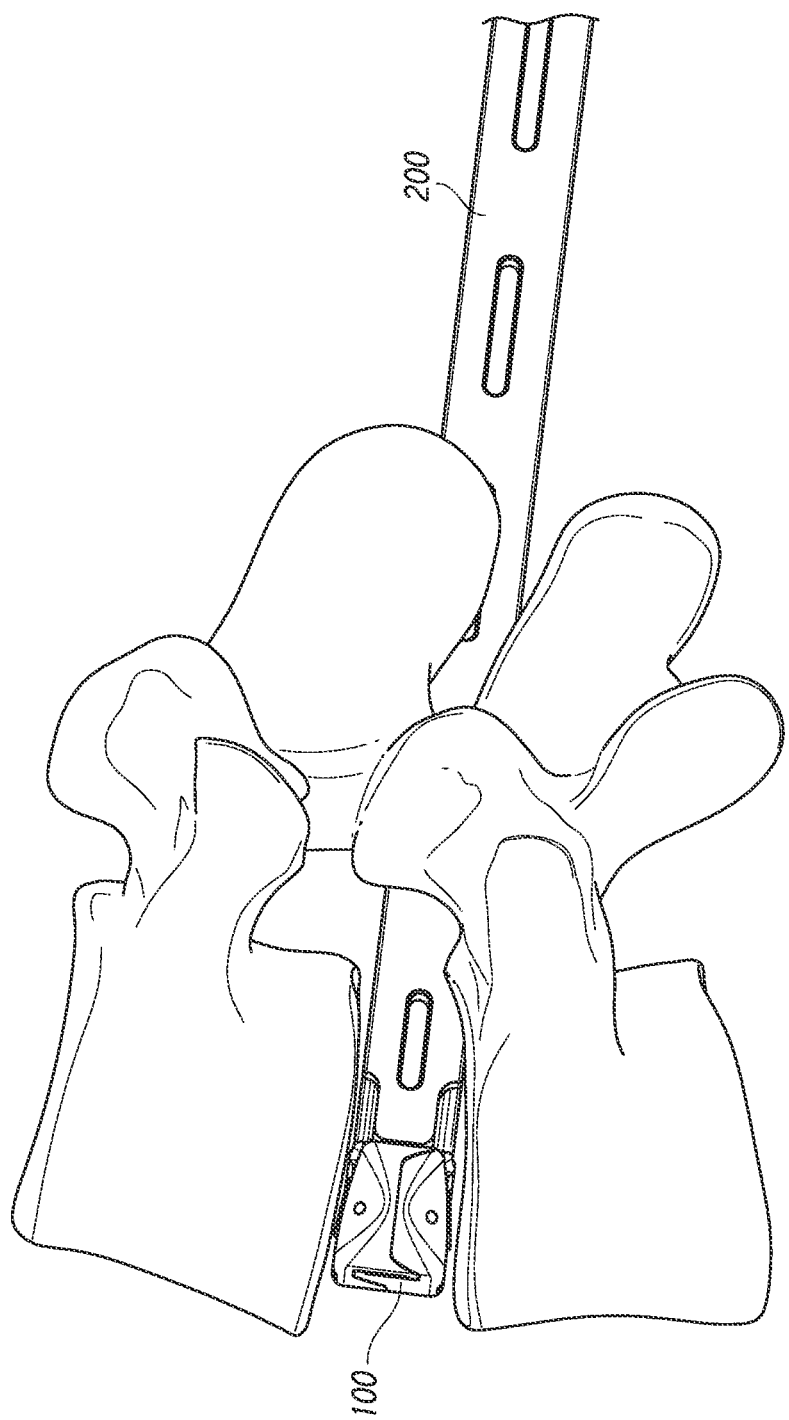

The deployment tool 200 can have a generally straight position while the deployment tool is initially inserted into the intervertebral space as shown in FIG. 27. The deployment tool 200 can be pivoted within the intervertebral space as shown in FIGS. 28-29. The deployment tool 200 can be pivoted by the user to navigate the anatomy. In some configurations, the deployment tool 200 can have a variable angle shaft such that the shape of the deployment tool 200 can be adjusted during use. For example, the deployment tool 200 can function as a hinge that adjusts the pivot angle of the deployment tool 200 for improved fitment of the deployment tool through the incision and to the target implant site. The deployment tool 200 can be stiff, bendable, or partially stiff and partially bendable. In some embodiments, a power source may be provided for hydraulic, pneumatic or other power-assisted manipulation of the deployment tool 200. In some embodiments, the keyed shaft 294 can be coupled to a power source to rotate the keyed shaft 294. In some embodiments, the locking mechanism 202, the pivoting mechanism 204, and the driving mechanism 206 are manually driven by the user.

The locking mechanism 202, the pivoting mechanism 204, and the driving mechanism 206 can have any actuation means. The locking mechanism 202, the pivoting mechanism 204, and the driving mechanism 206 can include a knob, a lever, a flat protrusion, a drive interface or other suitable mechanism for actuation. While a lever is shown for the actuator 230 and a button is shown for the actuator 240, any combination of interfaces can be utilized.

In some embodiments, the curved expandable interbody device 100 can be used to deliver fluids, medication or other materials, especially materials that can help in the integration of the curved expandable interbody device 100 with the vertebrae, such as allograft, Demineralized Bone Matrix ("DBM") packing, and/or other bone graft material. The material can fill the openings 120, 140. The curved expandable interbody device 100 can be packed with material before implantation. The curved expandable interbody device 100 can be packed with material after positioning the implant in the intervertebral space. The curved expandable interbody device 100 can be packed with material after expanding the implant. The material can fill up the empty cavity created between the upper structure 102 and lower structure 104 upon expansion, helping to provide support to the vertebrae.

The deployment tool 200 can be made of any appropriate material for the particular part. Materials can include, but are not limited to, stainless steel, surgical steel, cutlery steel, tool steel, cobalt and its alloys, nickel and its alloys, chromium and its alloys, titanium and its alloys, zirconium and its alloys, aluminum and its alloys, magnesium and its alloys, polymers, elastomers, and ceramics. Ceramics may include, but are not limited to silicon carbide, silicon oxide(s), silicon nitride, aluminum oxide, alumina, zirconia, tungsten carbide, other carbides.

The sizes of the curved expandable interbody device 100 and the deployment tool 200 are appropriate for treating the particular bone. Smaller devices can be used for smaller vertebra and larger devices for larger vertebra. In addition, while described in relation to the spine, the implant and deployment tool can be used on bones other than the vertebra and on bones for humans and non-humans.

Methods of implanting the curved expandable interbody device 100 can include selecting the implant size according to the sizing and goals of the procedure. In some embodiments, the curved expandable interbody device 100 can expand up to approximately 3 mm from its initial collapsed height. The user can select the curved expandable interbody device 100 from a plurality of implants. In some embodiments, the internal chamber of the curved expandable interbody device 100 may be packed with grafting material. Material can be packed through the openings 120, 140. Material can be packed when the curved expandable interbody device 100 is in a collapsed configuration. In some methods, the curved expandable interbody device 100 can be packed with material before coupling to the deployment tool 200. In some methods, the curved expandable interbody device 100 can be packed with material after coupling to the deployment tool 200. In some methods, the curved expandable interbody device 100 can be packed with material after placement within the intervertebral space.

The method can include coupling the curved expandable interbody device 100 to the deployment tool 200. The curved expandable interbody device 100 can have a dedicated deployment tool 200 that attaches securely to the curved expandable interbody device 100. The deployment tool 200 can provide control during insertion of the curved expandable interbody device 100. The method can include loading the curved expandable interbody device 100. The curved expandable interbody device 100 can be placed onto the distal end of the deployment tool 200. The deployment tool 200 can engage the curved expandable interbody device 100 by manipulating the locking mechanism 202. The curved expandable interbody device 100 can be secured to the deployment tool 200 by pushing the actuator 230 forward. The inner shaft 222 can be advanced between the deflection arms 224, 226 to position the tines 228 of the deflection arms 224 into the curved slots 198. The curved expandable interbody device 100 can be retained by the deployment tool 200.

The method can include preventing pivoting between the curved expandable interbody device 100 and deployment tool 200. The deployment tool 200 can be locked in a straight position by manipulating the pivoting mechanism 204. The position of the deployment tool 200 can be controlled by pressing the actuator 240 down and moving the actuator 240 forward to the straight position. The curved expandable interbody device 100 and the deployment tool 200 can be locked in a straight position by moving the pivoting mechanism 204 distally. The pivoting mechanism 204 moves the left arm 218 against the curved expandable interbody device 100. The left arm 218 can prevent pivoting as the curved expandable interbody device 100 is impacted.

An incision can be made on the patient to allow access to the implant site in the intervertebral space. The incision can be made for implanting the curved expandable interbody device 100 from any approach, including the posterior, lateral or anterior directions. The incision can be small for a minimally invasive procedure or a larger incision can be used for an open surgery. In some situations, two adjacent vertebrae can be distracted to open up the intervertebral space. In some configurations, the curved expandable interbody device 100 can be used to at least partially distract the vertebrae during the implant procedure. The incision and retraction of the soft tissues as well as a discectomy and any required decompression should be performed in accordance with procedures used in a spinal procedure. In some methods, the interbody device 100 can be used in a Lumbar Interbody Fusion (LIF) procedure.

The curved expandable interbody device 100 can be inserted into the intervertebral space. The curved expandable interbody device 100 and the deployment tool 200 can be locked for initial impaction. The curved expandable interbody device 100 and the deployment tool 200 can be in a straight position for initial impaction as shown in FIG. 27. The curved expandable interbody device 100 can be placed into the prepared site using gentle impaction, if necessary. A mallet can be included in the instrument set to aid in impacting the curved expandable interbody device 100 into the site. A user can manipulate the handle 216 of the deployment tool 200 to position the curved expandable interbody device 100 in the intervertebral space.

The deployment tool 200 can allow for pivoting motion to further assist in positioning the curved expandable interbody device 100 in the intervertebral space. The deployment tool 200 can be set into a pivoting mode by manipulating the pivoting mechanism 204. The position of the deployment tool 200 can be controlled by pressing the actuator 240 and moving the actuator 240 backward to the pivoting position. The curved expandable interbody device 100 and the deployment tool can remain locked by the locking mechanism 202 while allowing pivoting. The pivoting mechanism 204 can retract the left arm 218 relative to the curved expandable interbody device 100. The left arm 218 can be retracted to allow the deployment tool 200 to pivot relative to the curved expandable interbody device 100. The user can continue impacting the deployment tool 200 until the curved expandable interbody device 100 is manipulated into desired position within the disc space. The user can verify anterior-posterior and lateral placement with fluoroscope or other appropriate means. In some embodiments, the structures 102, 104 can have one or more markers 126, 146 to help visualization using radiation during the implantation procedure. The deployment tool 200 can be pivoted within the intervertebral space as shown in FIGS. 28-29.

The deployment tool 200 can expand the curved expandable interbody device 100. Once the curved expandable interbody device 100 is positioned between adjacent vertebrae, the driving mechanism 206 can be rotated to rotate the screw mechanism 106. The screw mechanism 106 changes length from a first length to a second length when rotated. The screw mechanism 106 expands the upper structure 102 and the lower structure 104 from a first height to a second height when rotated.

With the deployment tool 200 still locked to the curved expandable interbody device 100, the keyed shaft 294 may be placed inside the passageway of the deployment tool 200 and used to rotate the drive mechanism 206. The user can turn the keyed shaft 294 clockwise to expand the curved expandable interbody device 100. The user can monitor expansion via fluoroscopy or X-ray. The user can expand until the desired height is reached. The expansion may be stopped whenever desired between a collapsed configuration and the maximum expanded configuration. In some embodiments, the keyed shaft 294 can provide audible feedback such as a click when the limit of expansion is reached if expansion is not stopped prior to the maximum expanded configuration.

In some embodiments, materials such as fluids, medication, bone graft material, allograft and/or Demineralized Bone Matrix (DBM) can be delivered to the interior cavity of the curved expandable interbody device 100 after expansion. The material can be delivered through a delivery tube and into the proximal section of the curved expandable interbody device 100. In some embodiments, the material can be delivered through other paths to reach the cavities of the curved expandable interbody device 100 after expansion.

The deployment tool 200 can release the curved expandable interbody device 100. When the positioning and/or expansion are complete, the user can release the curved expandable interbody device 100 from the deployment tool 200 by actuating the locking mechanism 202. The user can flip the actuator 230 back into released position. The inner shaft 222 can be retracted relative to the deflection arms 224, 226 to retract the tines 228 of the deflection arms 224 from the curved slots 198. The curved expandable interbody device 100 can be released. The deployment tool 200 can be removed from the patient.

In some configurations, more than one curved expandable interbody device 100 can be implanted between the adjacent vertebrae of the patient. In such embodiments, multiple curved expandable interbody device 100 can be placed in a side-by-side configuration or any other suitable configuration, thereby creating additional support. The deployment tool 200 can be reused during a procedure to position one or more additional curved expandable interbody devices 100.

In some embodiments of the deployment tool 200, the movement of the locking mechanism 202, the pivoting mechanism 204, and the driving mechanism 206 can be effected by manual force applied by a person, such as by his or her hands, or alternatively it can be supplied or supplemented with a motor, pneumatics, hydraulics, springs, and/or magnetics. Some embodiments of the deployment tool 200 may comprise one or more actuators for actuating the mechanisms therein. Other embodiments of the deployment tool 200 can include mechanisms that include compound leverage, ratcheting, and/or multistep closing.

The method can include supplemental fixation. Supplemental fixation such as posterior pedicle screw and rod systems, anterior plate systems, and anterior screw and rod systems can be used in conjunction with the curved expandable interbody device 100. The kit can include manufacturers' recommendations for the implantation of these systems or other instructions for use. In some methods, systems that have been cleared for such uses can be implanted.

The method can include closure. The method can include post-operative care. Closing of the wound can be completed in line with normal practices for spinal procedures. In some methods, post-operative care and activity restriction can be administered and discussed with the patient in line with normal practices for spinal procedures.

In some methods, the method can include removal. In some methods, the method can include revision. In some methods, the user can determine the amount of bone removal necessary to free the curved expandable interbody device 100 if the curved expandable interbody device 100 needs to be removed. Once the curved expandable interbody device 100 is free from any surrounding bone, the deployment tool 200 may be used to re-engage and remove the curved expandable interbody device 100. The deployment tool 200 can collapse the curved expandable interbody device 100 before removal. The deployment tool 200 can be pivoted to facilitate removal. In some embodiments, the deployment tool 200 can include one or more markers to help visualization using radiation during the implantation and/or removal procedure.

Figure 30:
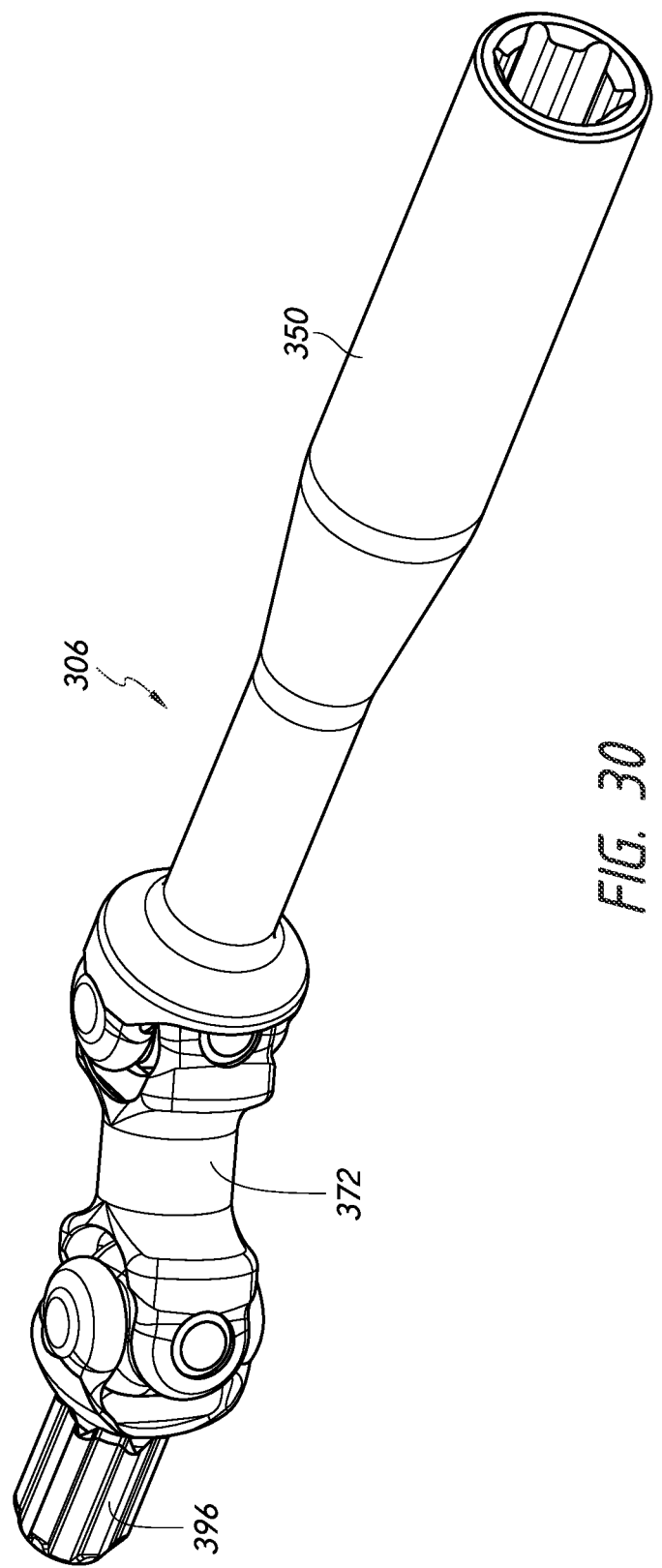
FIG. 30 is a close-up side view of a driving mechanism of a deployment tool of FIG. 13.
Figure 31:
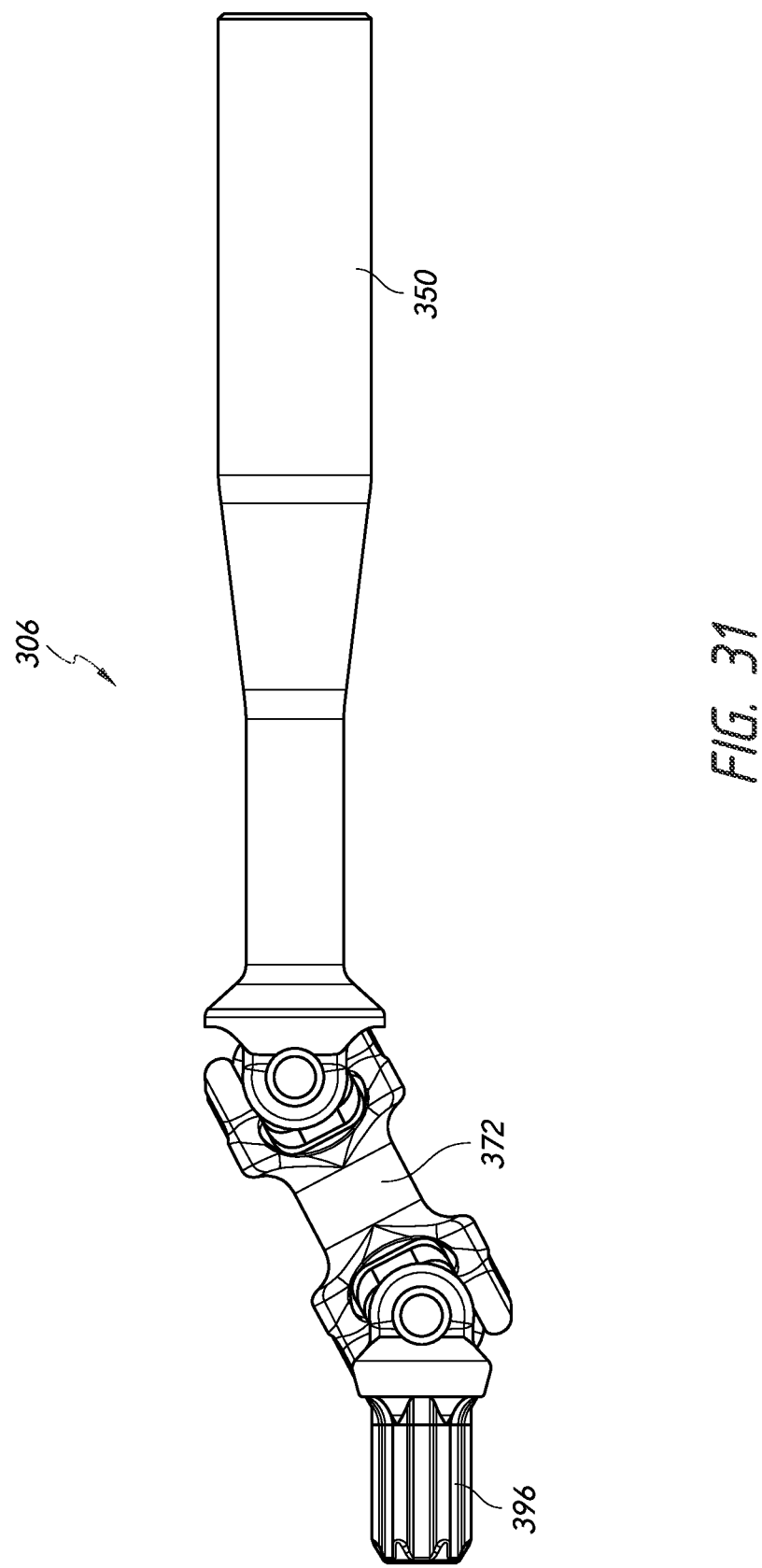
FIG. 31 is a close-up top view of the driving mechanism of the deployment tool of FIG. 13.
Figure 32:
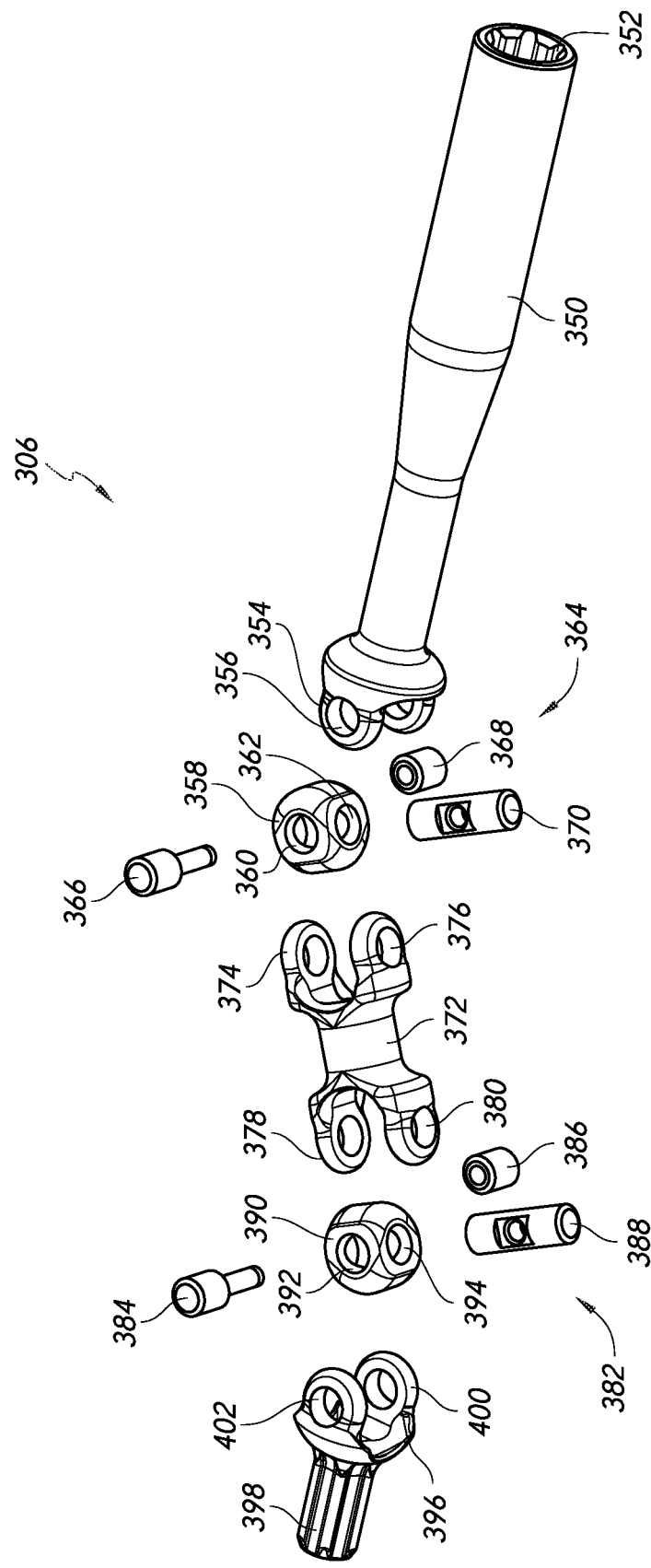
FIG. 32 is an exploded view of the driving mechanism of the deployment tool of FIG. 13.
Figure 33:
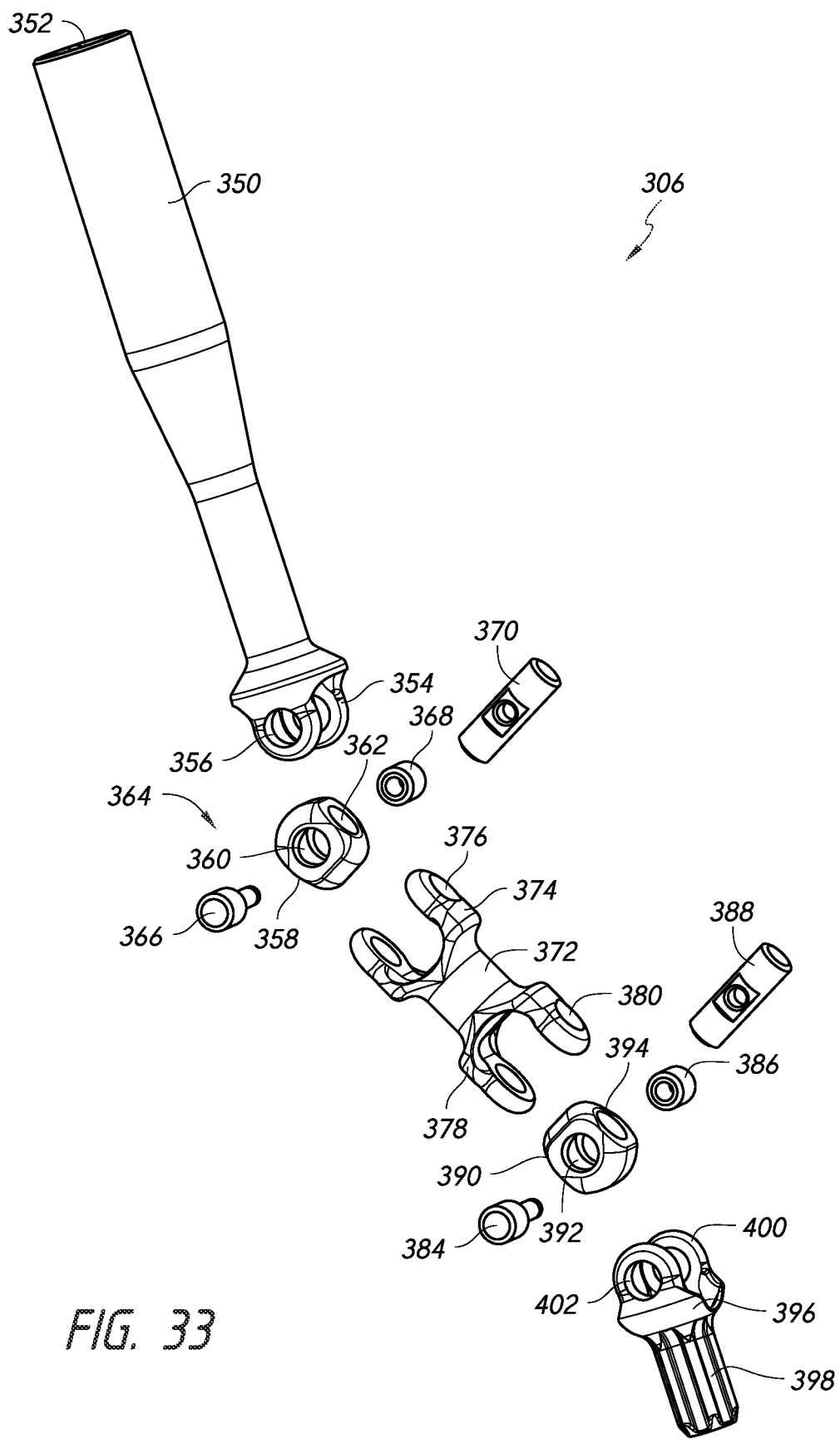
FIG. 33 is another exploded view of the driving mechanism of the deployment tool of FIG. 13.
Figure 34:
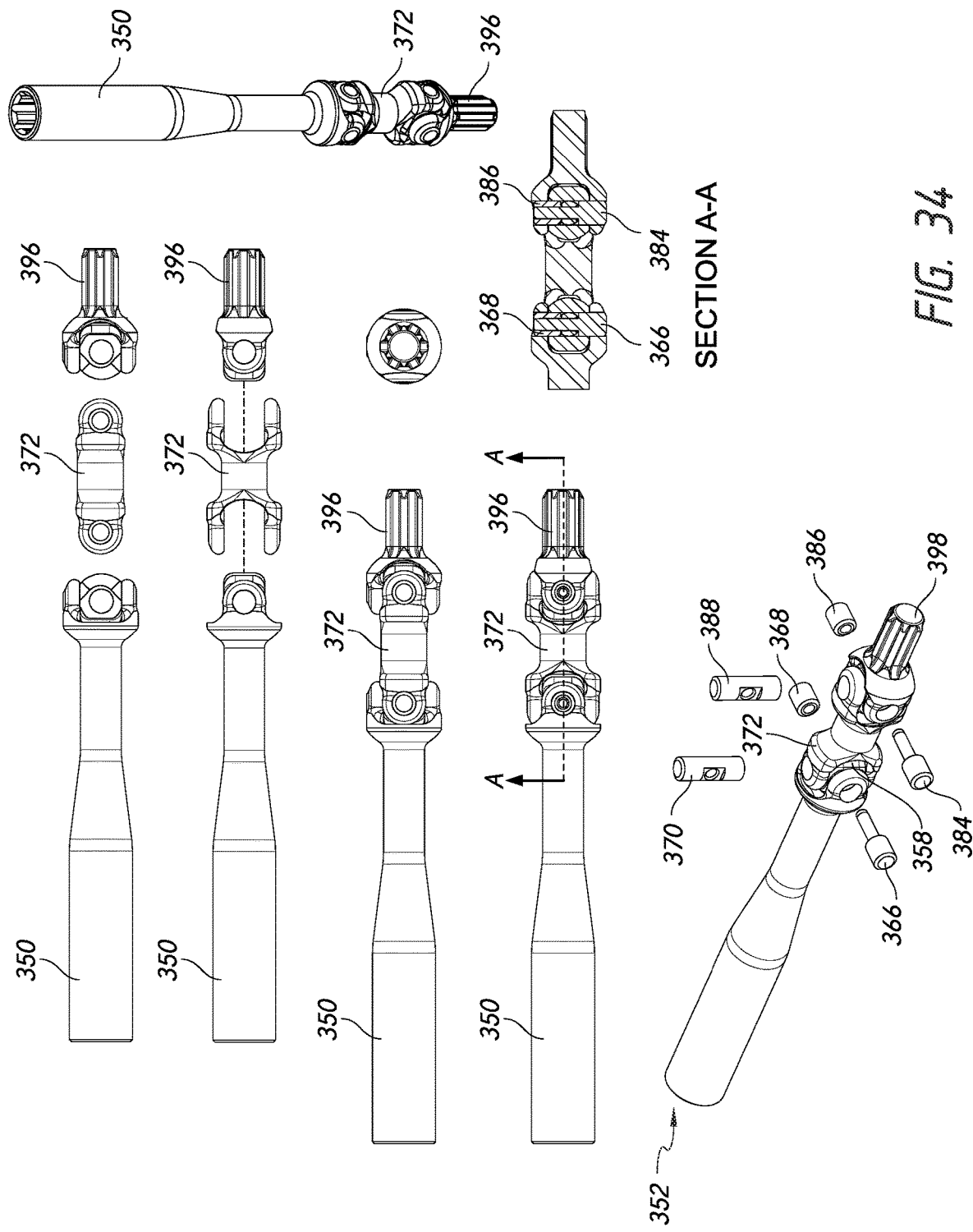
FIG. 34 is additional views of the driving mechanism of the deployment tool of FIG. 13.

FIG. 30 is a close-up side view of a driving mechanism 306 of a deployment tool 200. FIG. 31 is a close-up top view of the driving mechanism 306 of the deployment tool 200. FIGS. 32-33 are exploded views of the driving mechanism 306 of the deployment tool 200. FIG. 34 is additional views of the driving mechanism 306 of the deployment tool 200. The driving mechanism 306 can include any features of the driving mechanism 206 described herein.

Referring back to FIG. 13, the deployment tool 200 can include the elongated shaft 210. The deployment tool 200 can include the distal end 212 that is configured to interact with the curved expandable interbody device 100. The deployment tool 200 can include the proximal end 214 with the handle 216 configured to be gripped by the user. Referring back to FIGS. 16 and 17, the deployment tool 200 can include the locking mechanism 202. The locking mechanism 202 can be configured to interact with one or more curved slots 198 of the curved expandable interbody device 100. Once the deployment tool 200 is properly positioned relative to the curved expandable interbody device 100, the locking mechanism 202 can be activated to couple the deployment tool 200 to the curved expandable interbody device 100. Referring back to FIGS. 18 and 19, the deployment tool 200 can include the pivoting mechanism 204 to prevent pivoting of the deployment tool 200 relative to the curved expandable interbody device 100. The deployment tool 200 can have a straight position as shown in FIG. 14. The deployment tool 200 can have one or more pivoted positions.

FIGS. 30-34 illustrate the driving mechanism 306 with portions of the deployment tool 200 removed. The driving mechanism 306 can be an alternative embodiment to the driving mechanism 206. In some embodiments, the driving mechanism 306 can extend along a side of the deployment tool 200. The driving mechanism 306 can be along the right side of the deployment tool 200. The locking mechanism 202 and the pivoting mechanism 204 can be along the left side of the deployment tool 200. Other configurations of the mechanisms within the elongated shaft 210 are contemplated.

The driving mechanism 306 can include a first shaft 350. The first shaft 350 can be generally straight within the deployment tool 200. The first shaft 350 can include a driver interface. The first shaft 350 can include a keyed bore 352. The keyed bore 352 can extend from the proximal end of the first shaft 350. The keyed bore 352 can extend along a portion of the length of the first shaft 350. The keyed bore 352 can extend along a longitudinal axis of the first shaft 350. The first shaft 350 can include a yoke end 354. The yoke end 354 can include a pair of arms. The yoke end 354 can define a first bore 356.

The driving mechanism 306 can include a first block 358. The first block 358 can include a ball end. The first block 358 can fit into the yoke end 354. The first block 358 can fit between the pair of arms. The first block 358 can include a second bore 360. The first block 358 can include a third bore 362. The second bore 360 and the third bore 362 can be perpendicular. The first block 358 can form a portion of a universal joint. The first block 358 can be a universal joint block.

The driving mechanism 306 can include a first connector 364. The first connector 364 can include a first pin 366. The first connector 364 can include a first retainer sleeve 368. The first connector 364 can include a second pin 370. The first pin 366 and the first retainer sleeve 368 can couple to form a pivot. The first pin 366 and the first retainer sleeve 368 can be perpendicular to the second pin 370. The second pin 370 can receive a post of the first pin 366 therethrough. The post of the first pin 366 can be received by the first retainer sleeve 368. The first pin 366 and the first retainer sleeve 368 can intersect the second pin 370.

The first pin 366 and the first retainer sleeve 368 can be configured to be received in the first bore 356 of the first shaft 350. The first pin 366 and the first retainer sleeve 368 can be configured to be received in the second bore 360 of the first block 358. The first pin 366 and the first retainer sleeve 368 can be configured to couple the first block 358 and the first shaft 350. The yoke end 354 can be configured to receive the first block 358. The first block 358 can rotate relative to the yoke end 354 about the first pin 366 and the first retainer sleeve 368.

The driving mechanism 306 can include a second shaft 372. The second shaft 372 can be a linkage yoke. The second shaft 372 can be generally skewed within the deployment tool 200. The second shaft 372 can include a proximal yoke end 374. The proximal yoke end 374 can include a pair of arms. The first block 358 can fit into the proximal yoke end 374. The first block 358 can fit between the pair of arms. The proximal yoke end 374 can extend from the proximal end of the second shaft 372. The proximal yoke end 374 can receive the first block 358. The proximal yoke end 374 can extend along a portion of the length of the second shaft 372. The proximal yoke end 374 can extend along a longitudinal axis of the second shaft 372.

The proximal yoke end 374 can include fourth bore 376. The second pin 370 can be configured to be received in the fourth bore 376 of the second shaft 372. The second pin 370 can be configured to be received in the third bore 362 of the first block 358. The second pin 370 can couple the first block 358 and the second shaft 372. The second shaft 372 including the proximal yoke end 374, the first block 358, and the second pin 370 can rotate relative to the first shaft 350. In some embodiments, the first shaft 350 is fixed within the deployment tool 200. The yoke end 354 of the first shaft 350 is shaped to allow rotation of the second shaft 372 relative to the first shaft 350. The first block 358 has dual axis rotation. The first block 358 can rotate about the first pin 366 and the first retainer sleeve 368. The first block 358 can rotate about the about the axis of the second pin 370. The first connector 364 and the first block 358 can connect the rigid rods of the first shaft 350 and the second shaft 372. The axes of the first shaft 350 and the second shaft 372 can be inclined relative to each other at a fixed pivot angle. The first shaft 350 and the second shaft 372 can transmit rotary motion. The first pin 366 and the first retainer sleeve 368 act as first hinge. The second pin 370 acts as a second hinge. The first connector 370 orients the rotational hinges perpendicularly.

The first connector 364 and the first block 358 can allow a fixed pivot angle between the first shaft 350 and the second shaft 372. In some embodiments, the fixed pivot angle is an angle that the first shaft 350 and the second shaft 372 are relative to each other regardless of the orientation of the deployment tool 200 to the curved expandable interbody device 100. In some embodiments, the fixed pivot angle between the first shaft 350 and the second shaft 372 is 10 degrees, 15 degrees, 20 degrees, 21 degrees, 22 degrees, 23 degrees, 24 degrees, 25 degrees, 26 degrees, 27 degrees, 28 degrees, 29 degrees, 30 degrees, 31 degrees, 32 degrees, 33 degrees, 34 degrees, 35 degrees, 40 degrees, 45 degrees, 50 degrees, 55 degrees, 60 degrees, 65 degrees, 70 degrees, 75 degrees, 80 degrees, 85 degrees, 90 degrees, 95 degrees, 100 degrees, 105 degrees, 110 degrees, 115 degrees, 120 degrees, between 27 degrees and 30 degrees, between 20 degrees and 45 degrees, between 40 degrees and 90 degrees, or any range of two of the foregoing values. In some embodiments, the entire range of motion is between 5 degrees, 10 degrees, 15 degrees, 20 degrees, 25 degrees, 30 degrees, 35 degrees, 40 degrees, 45 degrees, 50 degrees, 55 degrees, 60 degrees, 65 degrees, 70 degrees, 75 degrees, 80 degrees, 85 degrees, 90 degrees, 95 degrees, 100 degrees, 105 degrees, 110 degrees, 115 degrees, 120 degrees, between 40 degrees and 90 degrees, between 50 degrees and 70 degrees, or any range of two of the foregoing values.

In some embodiments, the first shaft 350 and the second shaft 372 have a fixed angle therebetween. In other embodiments, the first shaft 350 and the second shaft 372 can have a variable angle therebetween. The first connector 364 and the first block 358 can maintain an angle between the first shaft 350 and the second shaft 372 when the driving mechanism 306 is disposed within the elongated shaft 210. In some embodiments, the first block 358 and first connector 364 can allow the first shaft 350 and the second shaft 372 to pivot relative to each other over a very limited range while within the deployment tool 200. In some embodiments, the first shaft 350 and the second shaft 372 do not pivot within the deployment tool 200. In some embodiments, the first shaft 350 and the second shaft 372 are held at a fixed pivot angle relative to each other in the deployment tool 200. This fixed pivot angle can be any angle. In some embodiments, the fixed pivot angle is between 27 degrees and 30 degrees. In some embodiments, the first block 358 and the first connector 364 are designed to accommodate the fixed pivot angle.

In some embodiments, the first shaft 350 and the second shaft 372 can be held by an internal pocket geometry in the deployment tool 200. The first shaft 350 and the second shaft 372 can be held by an internal pocket geometry near the distal end 212 of the deployment tool 200. This joint design can allow rotation and/or torque to be transmitted from the axis of the first shaft 350 to the axis of the second shaft 372. The first shaft 350 can function as the input drive shaft. The second shaft 372 can function as a universal joint.

The second shaft 372 can include a distal yoke end 378. The distal yoke end 378 can include a pair of arms. The distal yoke end 378 can extend from the distal end of the second shaft 372. The distal yoke end 378 can extend along a portion of the length of the second shaft 372. The distal yoke end 378 can extend along a longitudinal axis of the second shaft 372. The distal yoke end 378 can include a fifth bore 380. The fourth bore 376 and the fifth bore 380 can be parallel. The fourth bore 376 and the fifth bore 380 can be at a fixed angle relative to each other.

The driving mechanism 306 can include a second connector 382. The second connector 382 can include a third pin 384. The second connector 382 can include a third retainer sleeve 386. The second connector 382 can include a fourth pin 388. The third pin 384 and the third retainer sleeve 386 can couple to form a pivot. The third pin 384 and the third retainer sleeve 386 can be perpendicular to the fourth pin 388. The fourth pin 388 can receive a post of the third pin 384 therethrough. The post of the third pin 384 can be received by the third retainer sleeve 386. The third pin 384 and the third retainer sleeve 386 can intersect the fourth pin 388.

The driving mechanism 306 can include a second block 390. The second block 390 can include a ball end. The second block 390 can fit into the distal yoke end 378. The second block 390 can fit between the pair of arms. The second block 390 can include a sixth bore 392. The second block 390 can include a seventh bore 394. The sixth bore 392 and the seventh bore 394 can be perpendicular. The second block 390 can form a portion of a universal joint. The second block 390 can be a universal joint block.

The distal yoke end 378 can include the fifth bore 380. The fourth pin 388 can be configured to be received in the fifth bore 380 of the second shaft 372. The fourth pin 388 can be configured to be received in the seventh bore 394 of the second block 390. The fourth pin 388 can couple the second block 390 and the second shaft 372.

The driving mechanism 306 can include a third shaft 396. The third shaft 396 can be a driver tip. The third shaft 396 can be generally straight within the deployment tool 200. The third shaft 396 can include a keyed shaft 398. The keyed shaft 398 can extend from the distal end of the third shaft 396. The keyed shaft 398 can extend along a portion of the length of the third shaft 396. The keyed shaft 398 can extend along a longitudinal axis of the third shaft 396. The keyed shaft 398 can be configured to engage the drive interface 184. The screw mechanism 106 can include the drive interface 184 configured to receive the keyed shaft 396 of the driving mechanism 306 for rotating the screw mechanism 106.

The third shaft 396 can include a yoke end 400. The yoke end 400 can include a pair of arms. The yoke end 400 can define an eighth bore 402. The second block 390 can fit into the yoke end 400. The second block 390 can fit between the pair of arms. The yoke end 400 can allow pivoting motion of the second block 390.

The third pin 384 and the third retainer sleeve 386 can be configured to be received in the eighth bore 402 of the third shaft 396. The third pin 384 and the third retainer sleeve 386 can be configured to be received in the sixth bore 392 of the second block 390. The third pin 384 and the third retainer sleeve 386 can be configured to couple the second block 390 and the third shaft 396. The yoke end 400 can be configured to receive the second block 390. The second block 390 can pivot relative to the yoke end 400.

The second block 390 and the second connector 382 can couple the second shaft 372 and the third shaft 396. The second block 390 and the second connector 382 can allow the second shaft 372 and the third shaft 396 to pivot within the deployment tool 200. The second block 390 and the second connector 382 can allow the deployment tool 200 to change from a straight position to one or more pivoted positions. In some embodiments, the first shaft 350 and the second shaft 372 do not pivot within the deployment tool 200. In some embodiments, only the second shaft 372 and the third shaft 396 pivot within the deployment tool 200. The second shaft 372 and the third shaft 396 can allow for pivoting for the total range of the deployment tool 200 relative to the curved expandable interbody device 100. The second block 390 and the second connector 382 can be designed to allow for pivoting for the total range of the deployment tool 200 relative to the curved expandable interbody device 100.

The second shaft 372 including the distal yoke end 378, the second block 390, and the fourth pin 388 can rotate relative to the third shaft 396. In some embodiments, the third shaft 396 is fixed within the deployment tool 200. The yoke end 400 of the third shaft 396 is shaped to allow rotation of the second shaft 372 relative to the third shaft 396. The second block 390 has dual axis rotation. The second block 390 can rotate about the third pin 384 and the third retainer sleeve 386. The second block 390 can rotate about the about the axis of the fourth pin 388. The second connector 382 and the second block 390 can connect the rigid rods of the second shaft 372 and the third shaft 396. The axes of the second shaft 372 and the third shaft 396 can be inclined relative to each other. The second shaft 372 and the third shaft 396 can transmit rotary motion. The third pin 384 and the third retainer sleeve 386 act as a first hinge. The fourth pin 388 acts as a second hinge. The second connector 382 orients the rotational hinges perpendicularly.

In other embodiments, the first shaft 350 and the second shaft 372 pivot. The first shaft 350 and the second shaft 372 are not maintained at the fixed pivot angle. The first shaft 350, the second shaft 372, and the third shaft 396 can allow for pivoting for the total range of the deployment tool 200 relative to the curved expandable interbody device 100. The first block 358, the first connector 364, the second block 390, and the second connector 382 can be designed to allow for pivoting for the total range of the deployment tool 200 relative to the curved expandable interbody device 100.

The first shaft 350, the first block 358, the first connector 364, the second shaft 372, the second connector 382, the second block 390, and the third shaft 396 couple together to form an assembly. The first shaft 350, the first block 358, the first connector 364, the second shaft 372, the second connector 382, the second block 390, and the third shaft 396 can form a universal joint. The rotation of the first shaft 350 can cause rotation of the second shaft 372 which can cause rotation of the third shaft 396. The torque is transmitted by the first block 358 and the first connector 364 which couples the first shaft 350 and the second shaft 372. The torque is transmitted by the second block 390 and the second connector 382 which couples the second shaft 372 and the third shaft 396. The third shaft 396 can be coupled to the screw mechanism 106. The rotation of the first shaft 350 can cause rotation of the screw mechanism 106 to expand the curved expandable interbody device 100.

The first shaft 350, the first block 358, the first connector 364, the second shaft 372, the second connector 382, the second block 390, and the third shaft 396 allow the deployment tool 200 to be in any pivoted position while allowing the driving mechanism 306 to rotate the screw mechanism 106.

As the deployment tool 200 pivots, the first block 358 can rotate relative to the first shaft 350. The first block 358 rotates about the first pin 366 and the first retainer sleeve 368. The first block 358 rotates about the second pin 370. The first block 358 rotates about two perpendicular axes. During the transmission of torque and expansion of the curved expandable interbody device 100, the first shaft 350 can be fixed relative to the deployment tool. The dual axis pivoting allows torque to be transmitted from the first shaft 350 to the second shaft 372 As the deployment tool 200 pivots, the second block 390 can rotate relative to the third shaft 396. The second block 390 rotates about the third pin 384 and the third retainer sleeve 386. The second block 390 rotates about the fourth pin 388. The second block 390 rotates about two perpendicular axes. During the transmission of torque and expansion of the curved expandable interbody device 100, the third shaft 396 is coupled to the curved expandable interbody device 100. The dual axis pivoting allows torque to be transmitted from the second shaft 372 to the third shaft 396. As the deployment tool 200 pivots, the angle of the second shaft 372 changes relative to the fixed shaft 350, 396. The first shaft 350 can be fixed relative to the elongated shaft 210. The third shaft 396 can be fixed relative to the elongated shaft 210. The first block 358, the first connector 364, the second block 390, and the second connector 382 allow the second shaft 372 to reorient to accommodate the pivoted positions.

As the deployment tool 200 changes to one or more pivoted positions, the second shaft 372 must pivot relative to the third shaft 396. As the deployment tool 200 pivots, the second block 390 can rotate within the yoke end 400 of the third shaft 396. The second shaft 372 rotates relative to the third shaft 396 about two axes. The yoke end 400 of the third shaft 396 can accommodate the range of pivoted positions of the deployment tool 200 due to the dual axis rotation. The yoke end 400 of the third shaft 396 can accommodate rotation of the second block 390 up to 30 degrees, 40 degrees, 50 degrees, 60 degrees, 70 degrees, 80 degrees, 90 degrees, or any range of two of the foregoing values. In some methods of use, the first shaft 350 and the third shaft 396 can remain stationary as the deployment tool 200 assumes one or more pivoted positions. In some methods of use, the third shaft 396 remains coaxial with the longitudinal axis 108 of the curved expandable interbody device 100 regardless of the position of the deployment tool 200. In embodiments with a fixed pivot angle between the first shaft 350 and the second shaft 376, the first shaft 350 and the second shaft 376 can pivot relative to the third shaft 396 as the deployment tool 200 pivots.

The first block 358 and the second block 390 can accommodate the range of pivoted positions of the deployment tool 200. The first block 358 and the first connector 364 can maintain the fixed pivot angle between the first shaft 350 and the second shaft 372. The second block 390 and the second connector 382 can accommodate pivoting up to 30 degrees, 40 degrees, 50 degrees, 60 degrees, 70 degrees, 80 degrees, 90 degrees, or any range of two of the foregoing values. The pivoted positions can be accommodated due to the second block 390 and the second connector 382 allowing pivoting between the second shaft 372 and the third shaft 396.

As described herein, the deployment tool 200 can have a straight position. In the straight position of the deployment tool 200, the first shaft 350 and the second shaft 372 can be at the fixed pivot angle relative to each other. In the straight position, the first block 358 and the first connector 364 transmits torque between the first shaft 350 and the second shaft 372. In the straight position, the first shaft 350 rotates the first block 358 and the first connector 364 which rotates the second shaft 372. The first block 358 and the first connector 364 enables a sweep that is necessitated by the fixed pivot angle between the first shaft 350 and the second shaft 372. The first block 358 rotates relative to the first pin 366 and first retainer sleeve 368 forming a first hinge. The first block 358 rotates relative to second pin 370 forming a second hinge. The first block 358 and the first connector 364 accommodates the fixed pivot angle between the first shaft 350 and the second shaft 372 during a full rotation of the first shaft 350. In some embodiments, the fixed pivot angle between the first shaft 350 and the second shaft 372 is between 27 degrees and 30 degrees. The first block 358 and the first connector 364 can rotate twice the fixed pivot angle. Since the first shaft 350 and second shaft 372 are at the fixed pivot angle of 27 degrees to 30 degrees, the first block 358 and the first connector 364 will rotate from about negative 27 degrees to 30 degrees to positive 27 degrees to 30 degrees during a single rotation of the joint between the first shaft 350 and the second shaft 372. The universal coupling of the first block 358 and the first connector 364 can allow the deployment tool 200 to transmit torque in the straight position between the first shaft 350 and the second shaft 372.

In the straight position of the deployment tool 200, the second shaft 372 and the third shaft 396 can be skewed. In some embodiments, the angle between the second shaft 372 and the third shaft 396 in the straight position is 10 degrees, 15 degrees, 20 degrees, 21 degrees, 22 degrees, 23 degrees, 24 degrees, 25 degrees, 26 degrees, 27 degrees, 28 degrees, 29 degrees, 30 degrees, 31 degrees, 32 degrees, 33 degrees, 34 degrees, 35 degrees, 40 degrees, 45 degrees, 50 degrees, 55 degrees, 60 degrees, 65 degrees, 70 degrees, 75 degrees, 80 degrees, 85 degrees, 90 degrees, 95 degrees, 100 degrees, 105 degrees, 110 degrees, 115 degrees, 120 degrees, between 27 degrees and 30 degrees, between 20 degrees and 45 degrees, between 40 degrees and 90 degrees, or any range of two of the foregoing values. In some embodiments, the entire range of motion is between 5 degrees, 10 degrees, 15 degrees, 20 degrees, 25 degrees, 30 degrees, 35 degrees, 40 degrees, 45 degrees, 50 degrees, 55 degrees, 60 degrees, 65 degrees, 70 degrees, 75 degrees, 80 degrees, 85 degrees, 90 degrees, 95 degrees, 100 degrees, 105 degrees, 110 degrees, 115 degrees, 120 degrees, between 40 degrees and 90 degrees, between 50 degrees and 70 degrees, or any range of two of the foregoing values. The second block 390 rotates relative to the third pin 384 and third retainer sleeve 386 forming a first hinge. The second block 390 rotates relative to the fourth pin 388 forming a second hinge. The second block 390 and the second connector 382 accommodates the pivot angle between the second shaft 372 and the third shaft 396 during a full rotation of the second shaft 372. In some embodiments, the second shaft 372 and the third shaft 396 are at an angle of 27 degrees to 30 degrees when the deployment tool 200 is in the straight position. In the straight position, the second block 390 and the second connector 382 transmit torque between the second shaft 372 and the third shaft 396. The second block 390 and the second connector 382 enable a sweep that is necessitated by the pivot angle between the second shaft 372 and the third shaft 396 when the deployment tool 200 is in the straight position. The second block 390 and the second connector 382 accommodates this pivot angle between the second shaft 372 and the third shaft 396 during a full rotation of the second shaft 372. In some embodiments, the pivot angle between the second shaft 372 and the third shaft 396 is between 27 degrees and 30 degrees when the deployment tool 200 is in the straight position. The second block 390 and the second connector 382 can rotate twice the relative angle between the second shaft 372 and the third shaft 396. Since the second shaft 372 and the third shaft 396 are at the relative angle of 27 degrees to 30 degrees, the second block 390 and the second connector 382 will rotate from about negative 27 degrees to 30 degrees to positive 27 degrees to 30 degrees during a single rotation of the joint between the second shaft 372 and the third shaft 392 when the deployment tool 200 is in the straight position. The sliding of the second block 390 and the second connector 382 can allow the deployment tool 200 to transmit torque in the straight position between the second shaft 372 and the third shaft 396.

As described herein, the deployment tool 200 can have one or more pivoted positions. In the pivoted positions of the deployment tool 200, the first shaft 350 and the second shaft 372 remain at the fixed pivot angle relative to each other. In some embodiments, the fixed pivot angle between the first shaft 350 and the second shaft 372 is 10 degrees, 15 degrees, 20 degrees, 21 degrees, 22 degrees, 23 degrees, 24 degrees, 25 degrees, 26 degrees, 27 degrees, 28 degrees, 29 degrees, 30 degrees, 31 degrees, 32 degrees, 33 degrees, 34 degrees, 35 degrees, 40 degrees, 45 degrees, 50 degrees, 55 degrees, 60 degrees, 65 degrees, 70 degrees, 75 degrees, 80 degrees, 85 degrees, 90 degrees, 95 degrees, 100 degrees, 105 degrees, 110 degrees, 115 degrees, 120 degrees, between 27 degrees and 30 degrees, between 20 degrees and 45 degrees, between 40 degrees and 90 degrees, or any range of two of the foregoing values. In the pivoted positions, the first block 358 and the first connector 364 transmits torque between the first shaft 350 and the second shaft 372. The first block 358 and the first connector 364 rotate as the first shaft 350 rotates. The motion of the first block 358 and the first connector 364 accommodates the fixed pivot angle between the first shaft 350 and the second shaft 372 in one or more pivoted positions. The first block 358 and the first connector 364 can rotate up to twice the fixed pivot angle between the first shaft 350 and the second shaft 366 in both the straight positions and in the one or more pivoted positions of the deployment tool 200. Since the first shaft 250 and second shaft 266 are at the fixed pivot angle of 27 degrees to 30 degrees, the first block 358 and the first connector 364 can rotate from about negative 27 degrees to 30 degrees to positive 27 degrees to 30 degrees during a single rotation of the joint between the first shaft 350 and the second shaft 372 regardless of the angle of the deployment tool 200.

In a pivoted position of the deployment tool 200, the second shaft 372 can be at a different pivot angle relative to the third shaft 396. In some embodiments, the angle between the second shaft 372 and the third shaft 396 in the pivoted position is negative 45 degrees, negative 40 degrees, negative 35 degrees, negative 30 degrees, negative 25 degrees, negative 20 degrees, negative 15 degrees, negative 10 degrees, negative 5 degrees, 0 degrees, 5 degrees, 10 degrees, 15 degrees, 20 degrees, 25 degrees, 30 degrees, 31 degrees, 35 degrees, 40 degrees, 45 degrees, 50 degrees, 55 degrees, 60 degrees, 65 degrees, 70 degrees, 75 degrees, 80 degrees, 85 degrees, 90 degrees, 95 degrees, 100 degrees, 105 degrees, 110 degrees, 115 degrees, 120 degrees, between 27 degrees and 30 degrees, between 20 degrees and 45 degrees, between 40 degrees and 90 degrees, between negative 30 degrees and 30 degrees, between negative 45 degrees and 45 degrees, between negative 20 degrees and 20 degrees, between 0 degrees and 30 degrees, or any range of two of the foregoing values. The second shaft 372 and the third shaft 396 can pivot relative to each other approximately negative 30 degrees to positive 30 degrees.

This pivoting of the second shaft 372 and the third shaft 396 combined with the fixed pivot angle of 27 to 30 degrees between the first shaft 350 and the second shaft 372 allows the deployment tool 200 to achieve cumulative total deployment tool pivot angles of 0 degrees to 60 degrees. In the pivoted positions, the second block 390 and the second connector 382 transmits torque between the second shaft 272 and the third shaft 296. In at least some pivoted positions, the second shaft 372 becomes skewed relative to the third shaft 396. The second block 390 and the second connector 382 transmits torque when the second shaft 372 and the third shaft 396 are angulated. In some embodiments, the second block 390 and the second connector 382 need to rotate about twice the relative angle between the second shaft 372 and the third shaft 396. Since the second shaft 372 and the third shaft 396 can have a variable angle, the second block 390 and the second connector 382 can rotate from any range between negative 30 degrees and positive 30 degrees during a single rotation of the joint between the second shaft 372 and the third shaft 396. Unlike the first shaft 350 and the second shaft 372 that have a fixed pivot angle, the second shaft 372 and the third shaft 396 do not have a fixed pivot angle. The second shaft 372 and the third shaft 396 can have a variable angle depending on the angulation of the deployment tool 200.

In one pivoted position, wherein the deployment tool 200 is approximately 30 degrees relative to the curved expandable interbody device 100, the second shaft 372 and the third shaft 396 can be coaxial. In this position, the longitudinal axis of the second shaft 372 can be aligned with the longitudinal axis of the third shaft 396.

If the second shaft 372 and the third shaft 396 have a relative angle of negative 30 degrees or positive 30 degrees, then the second block 390 and the second connector 382 need to rotate from negative 30 degrees to positive 30 degrees. If the second shaft 372 and the third shaft 396 have a relative angle of negative 15 degrees, then the second block 390 and the second connector 382 need to rotate from negative 15 degrees to positive 15 degrees. If the second shaft 372 and the third shaft 396 have a relative angle of positive 15 degrees, then the second block 390 and the second connector 382 also need to rotate from negative 15 degrees to positive 15 degrees. If the second shaft 372 and the third shaft 396 have a relative angle of 0 degrees, then the second block 390 and the second connector 382 need to rotate 0 degrees.

The combined rotating of the first block 358 and the second block 390 can allow the deployment tool 200 to transmit torque in the straight position and one or more pivoted positions. The second shaft 372 and the third shaft 396 can pivot relative to each other approximately negative 30 degrees to positive 30 degrees. This pivoting of the second shaft 372 and the third shaft 396, combined with the fixed angle of 27 degrees to 30 degrees between the first shaft 350 and second shaft 372 can achieve a cumulative total pivot angle of the deployment tool 200 of between 0 degrees to 60 degrees.

The combined rotating of the second block 390 can facilitate engagement of the third shaft 396 with the curved expandable interbody device 100. The second block 390 rotates relative to the third pin 384 and third retainer sleeve 386 forming a first hinge. The second block 390 rotates relative to fourth pin 388 forming a second hinge. The second block 390 and the second connector 382 can allow polyaxial movement of the third shaft 396. This polyaxial movement of the third shaft 396 can facilitate coupling the deployment tool 200 to the curved expandable interbody device 100.

Referring back to FIG. 25, the deployment tool 200 can include a passageway toward the keyed bore 352 of the first shaft 350. The keyed bore 352 is configured to receive the keyed shaft 294 inserted into the deployment tool 200. The keyed shaft 294 can be inserted into the deployment tool 200 to expand the curved expandable interbody device 100. As the keyed shaft 294 is rotated, the first shaft 350 also rotates.

By rotating the keyed shaft 294 at the proximal portion of the deployment tool 200, the first shaft 350 is also rotated, which in turn rotates the second shaft 372 and the third shaft 396, and thus the drive interface 184 of the screw mechanism 106 to expand the curved expandable interbody device 100.

As the driving mechanism 306 applies the rotational force, the curved expandable interbody device 100 gradually expands as described herein. The keyed shaft 294 can advantageously transmit sufficient torque to the screw mechanism 106 to enable distraction using the curved expandable interbody device 100.

The deployment tool 200 can include the locking mechanism 202, the pivoting mechanism 204, and the driving mechanism 306. The locking mechanism 202, the pivoting mechanism 204, and the driving mechanism 306 can be independently actuated. The locking mechanism 202, the pivoting mechanism 204, and the driving mechanism 306 can be actuated in a preferred order. In some methods, the locking mechanism 202 is actuated first to lock the deployment tool 200 to the curved expandable interbody device 100. In some methods, the pivoting mechanism 204 is actuated next to limit pivoting movement during positioning of the curved expandable interbody device 100. In some methods, the driving mechanism 306 is actuated last to expand the curved expandable interbody device 100. The driving mechanism 206 can include any features of the driving mechanism 306 described herein.

Although certain embodiments, features, and examples have been described herein, it will be understood by those skilled in the art that many aspects of the methods and devices illustrated and described in the present disclosure may be differently combined and/or modified to form still further embodiments. For example, any one component of the device illustrated and described above can be used alone or with other components without departing from the spirit of the present disclosure. Additionally, it will be recognized that the methods described herein may be practiced in different sequences, and/or with additional devices as desired. Such alternative embodiments and/or uses of the methods and devices described above and obvious modifications and equivalents thereof are intended to be included within the scope of the present disclosure. Thus, it is intended that the scope of the present disclosure should not be limited by the particular embodiments described above, but should be determined only by a fair reading of the claims that follow.

What is claimed is:

1. A curved expandable interbody device for placement between vertebrae comprising:
    an upper structure configured to abut a superior vertebra, wherein the upper structure comprises an upper surface, a first side surface, and a second side surface, wherein the first side surface is concave, wherein the second side surface is convex;
    a lower structure configured to abut an inferior vertebra, wherein the lower structure comprises a lower surface, a third side surface, and a fourth side surface, wherein the third side surface is concave, wherein the fourth side surface is convex; and
    a screw mechanism between the upper structure and the lower structure, the screw mechanism comprising a proximal portion, a distal portion, and a coupler, wherein the coupler comprises a central portion at least partially between the proximal portion and the distal portion, wherein the coupler further comprises a proximal interface comprising a first arm, a second arm, an upper connector forming a curved arc between the first arm and the second arm, and a lower connector forming a curved arc between the first arm and the second arm,
    wherein the proximal portion and the distal portion are configured to rotate as a unit to change a distance between the proximal portion and the distal portion from a first length to a second length, and
    wherein the first side surface of the upper structure, the third side surface of the lower structure, and the first arm of the coupler form a smooth concave side having the same radius of curvature, wherein the second side surface of the upper structure, the fourth side surface of the lower structure, and the second arm of the coupler form a smooth convex side having the same radius of curvature.

2. The curved expandable interbody device of claim 1, wherein the proximal portion comprises a frustoconical surface configured to wedge between the upper structure and the lower structure, and wherein the distal portion comprises a frustoconical surface configured to wedge between the upper structure and the lower structure to change a distance between the upper structure and the lower structure from a first height to a second height.

3. The curved expandable interbody device of claim 1, wherein the proximal portion comprises first threads wound in a first direction configured to engage a proximal threaded hole in the coupler, and wherein the distal portion comprises second threads wound in a second direction, opposite the first direction, configured to engage a distal threaded hole in the coupler.

4. The curved expandable interbody device of claim 3, wherein the first threads and the second threads have an equal pitch, such that when the screw mechanism is actuated, a proximal end of the curved expandable interbody device changes height at a same rate as a distal end of the interbody device.

5. The curved expandable interbody device of claim 3, wherein the curved expandable interbody device is configured to expand up to 4 mm from an initial collapsed height.

6. The curved expandable interbody device of claim 1, wherein one or more of the upper structure and the lower structure further comprise a plurality of protrusions.

7. The curved expandable interbody device of claim 1, wherein one or more of the upper structure and the lower structure comprise vertebrae engagement surfaces with a porous or roughened surface.

8. The curved expandable interbody device of claim 7, wherein the vertebrae engagement surfaces comprise a titanium coating.

9. The curved expandable interbody device of claim 1, wherein the proximal portion comprises a drive interface configured to be engaged by a deployment tool to rotate the proximal portion and the distal portion.

10. The curved expandable interbody device of claim 1, wherein the distal portion comprises a keyed shaft configured to slideably engage with a matching keyed bore on the proximal portion.

11. The curved expandable interbody device of claim 1, wherein the coupler further comprises at least one anti-rotational feature configured to engage the upper structure or the lower structure to prevent the coupler from rotating when the proximal portion and the distal portion are rotated.

12. A system comprising:
    the curved expandable interbody device of claim 1; and
    a deployment tool.

13. The system of claim 12, wherein the upper structure and the upper connector form an upper curved slot therebetween and the lower structure and the lower connector form a lower curved slot therebetween, wherein the upper curved slot and the lower curved slot are configured to be engaged by the deployment tool to lock the deployment tool to the curved expandable interbody device.

14. The system of claim 12, wherein the upper structure and the upper connector form an upper curved slot therebetween and the lower structure and the lower connector form a lower curved slot therebetween, wherein the upper and lower curved slot are configured to allow pivoting of the deployment tool relative to the curved expandable interbody device.

15. The system of claim 12, wherein the upper structure and the upper connector form an upper curved slot therebetween and the lower structure and the lower connector form a lower curved slot therebetween, wherein the upper and lower curved slot are configured to allow pivoting of the deployment tool in the direction of the smooth concave side of the curved expandable interbody device.

16. The system of claim 12, wherein the deployment tool comprises tines configured to engage an upper curved slot and a lower curved slot, wherein the tines are configured to slide within the upper curved slot and the lower curved slot.

17. The system of claim 12, wherein the deployment tool comprises an arm configured to fit between the upper connector and the lower connector of the coupler.

18. A method comprising:
coupling a deployment tool to the curved expandable interbody device of claim 1;
positioning the curved expandable interbody device between the superior vertebra and the inferior vertebra;
pivoting the deployment tool and the curved expandable interbody device relative to each other to further position the curved expandable interbody device between the superior vertebra and the inferior vertebra; and
rotating the screw mechanism to expand the curved expandable interbody device.

19. The method of claim 18, wherein coupling the deployment tool to the curved expandable interbody device comprises coupling the deployment tool in a locked, straight position relative to the curved expandable interbody device.

20. The method of claim 18, wherein pivoting the deployment tool relative to the curved expandable interbody device comprises pivoting the deployment tool to a pivoted position of a plurality of pivoted positions.

\* \* \* \* \*